(12) United States Patent
Crispim et al.

(10) Patent No.: US 12,275,803 B2
(45) Date of Patent: Apr. 15, 2025

(54) FUNCTIONALIZATION OF BIOPOLYMERS WITH GROWTH FACTOR-BINDING PEPTIDES

(71) Applicant: Universiteit Twente, Enschede (NL)

(72) Inventors: João Francisco Ribeiro Pereira Simões Crispim, Eindhoven (NL); Pascal Jonkheijm, Manderveen (NL); Daniël Bart Frederik Saris, Rochester, MN (US)

(73) Assignee: Universiteit Twente, Enschede (NL)

( * ) Notice: Subject to any disclaimer, the term of this patent is extended or adjusted under 35 U.S.C. 154(b) by 908 days.

(21) Appl. No.: 16/465,524

(22) PCT Filed: Nov. 30, 2017

(86) PCT No.: PCT/NL2017/050800
§ 371 (c)(1),
(2) Date: May 30, 2019

(87) PCT Pub. No.: WO2018/101826
PCT Pub. Date: Jun. 7, 2018

(65) Prior Publication Data
US 2020/0095341 A1   Mar. 26, 2020

(30) Foreign Application Priority Data
Nov. 30, 2016 (NL) .................................. 2017900

(51) Int. Cl.
| | | |
|---|---|---|
| *C07K 17/08* | (2006.01) | |
| *A61K 47/59* | (2017.01) | |
| *C07K 14/47* | (2006.01) | |
| *C07K 16/22* | (2006.01) | |

(52) U.S. Cl.
CPC ............ *C07K 17/08* (2013.01); *A61K 47/593* (2017.08); *C07K 14/47* (2013.01); *C07K 16/22* (2013.01)

(58) Field of Classification Search
CPC ........ C07K 17/08; C07K 14/47; C07K 16/22; A61K 47/593
See application file for complete search history.

(56) References Cited

U.S. PATENT DOCUMENTS

| 8,138,140 B2 | 3/2012 | Stupp et al. | |
|---|---|---|---|
| 9,290,579 B2 * | 3/2016 | Vepari ..................... | C12N 11/10 |
| 2003/0216524 A1 * | 11/2003 | Bide ..................... | C08G 63/916 |
| | | | 525/418 |
| 2005/0209145 A1 * | 9/2005 | Stupp ................... | C07K 14/475 |
| | | | 514/8.1 |
| 2009/0098175 A1 * | 4/2009 | Buehrer ................. | A61L 27/227 |
| | | | 530/324 |
| 2010/0266557 A1 * | 10/2010 | Shah ................... | A61K 38/1841 |
| | | | 514/21.7 |
| 2017/0056544 A1 * | 3/2017 | Pokorski ................. | A61L 15/44 |

FOREIGN PATENT DOCUMENTS

| WO | WO-2005056039 A1 * | 6/2005 | ............. A61K 38/18 |
|---|---|---|---|
| WO | WO-2008105797 A2 * | 9/2008 | ............. C07K 16/40 |
| WO | 2011/049449 A1 | 4/2011 | |
| WO | WO-2011063152 A1 * | 5/2011 | ............. A61K 38/10 |

OTHER PUBLICATIONS

Svensson, Osteoarthritis and Cartilage (2001) 9, Supplement A, S23-S28 (Year: 2001).*
Smith Callahan et al., Acta Biomaterialia 9 (2013) 7420-7428 (Year: 2013).*
Lutz, J. Polym. Sci. Part A: Polym. Chem.: vol. 46 (2008), 3459-3470 (Year: 2008).*
Siow, Plasma Process. Polym.2006,3, 392-418 (Year: 2006).*
Ulery et al., Journal of Polymer Science Part B: Polymer Physics2011, 49, 832-864 (Year: 2011).*
Madler et al., J. Mass. Spectrom. 2009, 44, 694-706 (Year: 2009).*
Belisle et al., J Mater Sci (2011) 46:6154-6157 (Year: 2011).*
Protein Man blog, Sep. 26, 2017, downloaded from the internet Apr. 13, 2023, 5 pages (Year: 2017).*
Wikipedia pages for "carbonyl group", downloaded from the internet Mar. 14, 2024 (Year: 2024).*
Hokamura et al., Bioscience, Biotechnology, and Biochemistry, 2015, vol. 79, No. 8, 1369â1377 (Year: 2015).*
Maestro and Sanz, Microbial Biotechnology, 2017, 10, 1323-1337 (Year: 2017).*
Albans et al., Journal of Chemical Ecology, vol. 6, No. 3, 1980 (Year: 1980).*
Arabi et al., Surface Innovations, Jan. 2013, 7 pages (Year: 2013).*
Coad et al. "Controlled covalent surface immobilisation of proteins and peptides using plasma methods" Surface &-Coatings Technology 233 (2013) pp. 169-177.

* cited by examiner

*Primary Examiner* — Melissa L Fisher
*Assistant Examiner* — Joseph Fischer
(74) *Attorney, Agent, or Firm* — TraskBritt

(57) ABSTRACT

The disclosure relates to a biopolymer that is functionalized with a peptide, preferably a growth factor-binding peptide. The disclosure further relates to a device comprising a functionalized biopolymer, to methods for treatment of a tissue pathology in a subject using a device according to the disclosure, to methods for coupling peptides to carbonyl groups of a biopolymer, and to a use of oxygen plasma for coupling a peptide to carbonyl groups of a biopolymer.

14 Claims, 26 Drawing Sheets
Specification includes a Sequence Listing.

FUNCTIONALIZATION OF BIOPOLYMERS WITH GROWTH FACTOR-BINDING PEPTIDES

CROSS-REFERENCE TO RELATED APPLICATIONS

This application is a national phase entry under 35 U.S.C. § 371 of International Patent Application PCT/NL2017/050800, filed Nov. 30, 2017, designating the United States of America and published in English as International Patent Publication WO 2018/101826 A1 on Jun. 7, 20189, which claims the benefit under Article 8 of the Patent Cooperation Treaty to Dutch Patent Application Serial No. 2017900, filed Nov. 30, 2016.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

The disclosure relates to functionalized biopolymers that can be used for tissue engineering. The functionalized biopolymers provide growth factor binding peptides that capture endogenous growth factors after implantation into a tissue.

BACKGROUND

Owing to an aging population and involvement in physical activities, musculoskeletal injuries are among the most common injures worldwide. From about 33 million injuries reported in the US per year, approximately 33% involve T/L (James et al., 2008, J. Hand. Surg. Am. 33:102-12). The most frequently reported injury is that of the anterior cruciate ligament (ACL) tear or rupture, which accounts for more than 80,000 cases per year in the US alone, with an estimated cost of US$1.0 billion (Griffin et al., 2000, J. Am. Acad. Orthop. Surg. 8:141-50). Due to improvements in quality of life and the increasing participation of the population in physical activities, the incidence of these injuries is likely to rise, affecting patient quality of life and increasing healthcare costs. Injuries to these tissues are always associated with pain, swelling and disability, with the extent of the damage dictating recovery time (Chen et al., 2008, Curr. Rev. Musculoskelet. Med. 1:108-113; Medicine 2016; Knee Ligament Repair, available from hopkinsmedicine.org/healthlibrary/test_procedures/orthopaedic/knee_ligament_repair_92,p0767 5).

When tears or ruptures of the tissues occur, surgical intervention is usually needed. The main goal of this surgical treatment is to stabilize and restore normal movement to the joint (Baumhauer and O'Brien, 2002, J. Athl. Train. 37:458-462). Due to the nature of these tissues and their inherent poor healing capacity, surgical intervention is also needed to direct the natural healing process. However, even with the available treatments, complete healing of the damaged tissue is difficult to achieve, which can ultimately lead to scarring, restrictions to the range of motion, stiffness/weakness of the joint, improper healing and re-injury (Krans, 2016, ACL Reconstruction, available from healthline.com/health/acl-reconstruction#Overview1). After surgery, a long recovery period is required of between 9 to 12 months, during which the patient's movement and quality of life are affected and the pre-injury properties of the T/L are likely not yet fully restored (Voleti et al., 2012, Annu. Rev. Biomed. Eng., 14:47-71).

Consequently, there is a need to improve the current treatments and make the overall surgical and rehabilitation process more efficient, shorter and friendlier to the patient, not only for treatment of tendons and ligaments, but for treatment of a tissue injury in general.

BRIEF SUMMARY

For this, the disclosure provides a biopolymer that is functionalized with a peptide. The peptide preferably is a growth factor-binding peptide. The biopolymer preferably comprises one or more carbonyl groups, preferably one or more ketone groups, more preferably one or more carboxylic acid groups, that are functionalized with one or more peptides, preferably produced by a method of the disclosure.

The term "biopolymer," as is used herein, refers to a natural or synthetic material that can be used to replace part of a living system or to function in living tissue. A preferred functionalized biopolymer comprises a peptide that is coupled to a carbonyl group of the non-functionalized biopolymer, preferably to a non-functionalized biopolymer comprising aldehyde, ketone, ester, carboxylate ester, and/or amide groups. A preferred non-functionalized biopolymer is a polyester.

A tissue that may be treated with a functionalized biopolymer according to the disclosure preferably is bone, cartilage, tendon, ligament, nerve, skin, vascular, cardiac, pericardial, muscle, ocular, periodontal, breast, pancreatic, esophageal, stomach, kidney, hepatic, mammary, adrenal, urological, and intestinal tissue. Hence, the tissue that is to be regenerated or treated may be selected form the group consisting of bone, cartilage, tendon, ligament, nerve, skin, vascular, cardiac, pericardial, muscle, ocular, periodontal, breast, pancreatic, esophageal, stomach, kidney, hepatic, mammary, adrenal, urological, and intestinal tissue. The tissue preferably is selected from the group consisting of bone, cartilage, tendon and ligament.

Mammals in need of regenerating tissue comprise mammals wherein injury to tissue has occurred. Surgical intervention is often required to repair the damage. Such surgical repairs can include suturing or otherwise repairing the damaged tissue with known medical devices, augmenting the damaged tissue with other tissue, using an implant, a graft or any combination of these techniques. According to this disclosure, tissue may be regenerated in a mammal by implanting a device comprising a functionalized biopolymer of the invention. The injured tissue of a mammal, preferably human, is preferably selected from the group consisting of articular cartilage defects, meniscal defects, discus intervertebralis defects, bone defects, vertebral body fractures, skin wounds, fascial defects, tendon ruptures, ligament ruptures, nerve injuries, spinal cord injuries, blood vessel defects, ear substitution, nasal cartilage defects, muscle defects, heart muscle defects, muscle degeneration, adipose defects, tooth injuries, bladder wall defects, gastric wall defects, intestinal wall defects, pancreatic island transplantation, and eye injuries.

Preferred biopolymers can have a natural origin, such as collagen, chitosan, dextran, hyaluronic acid, heparin, heparin, polysaccharide such as alginate (or alginic acid), hyaluronic acid, agarose etc.; polynucleotide, polypeptide, starch, and/or combinations thereof. The biopolymer is preferably not a peptide or polypeptide. Synthetic biopolymers include poly lactic acid, poly-L-lactic acid, polyglycolic acid, polyglycolic lactic acid, poly(amidoamine), poly (caprolactone), polyalkyleneoxide-polyalkylene-terephtalate block copolymer, poly-N-isopropylacrylamide, polyurethane, poly-acrylate, polyesters, polystyrene, polycarbonate, polyethyleneterephtalate (PET) polybutyleneterephtalate (PBT), polyethyleneoxide (PEO), polyethersulfone (PES), polytetra-fluoroethylen (PTFE), polytrimethylenecaprolactone (PTMC), polyanhydride, polylactic acid (PLA), poly-4-hydroxybutyrate, poly(ortho) ester and polyphosphazene and/or combinations thereof. The biopolymer is preferably a polyester, preferably a polyethyleneterephtalate. The biopolymer preferably is biocompatible. Biocompatible in this context means that the biopolymer is typically not harmful to the patient and that the polymer typically does not elicit a pathological response of the body against the biopolymer.

The term "functionalized," as is used herein, relates to modification of the biopolymer to provide one or more peptides on the surface of the biopolymer. The term is used as an equivalent to the term "coupled to."

The disclosure provides a biopolymer comprising a peptide, preferably a growth-factor binding peptide. The peptide is preferably a peptide that can exhibit a function when present in the body of a subject. One such function is preferably a growth-factor binding function. In this context, the disclosure further provides a biopolymer that is functionalized with a peptide.

The term "peptide," as is used herein, refers to chains of amino acid residues linked by peptide bonds. The number of amino acid residues preferably is between 5 and 1000 amino acid residues, more preferably between 5 and 100 amino acid residues, more preferably between 5-75; more preferably 5-50; more preferably 5-25 and more preferably 5-15 amino acid residues.

Numerical ranges indicated herein include the individual numbers indicated. For example, a range of 5-15, or between 5 and 15; includes the numbers 5 and 15.

In one embodiment, the biopolymer is functionalized with a peptide. The peptide contains carbon atoms and nitrogen atoms and other atoms. The peptide preferably comprises a ratio of nitrogen to carbon atoms of 0.10-0.5; preferably 0.15-0.4; preferably 0.2-0.33. The percentage of nitrogen atoms derived from the peptide to carbon atoms derived from the biopolymer is preferably 0.2%-20%; preferably 0.5%-15%; preferably 0.5% to 12%; preferably 1%-10%; preferably 2%-9%. These ratios and percentages are particularly useful for biopolymer films. The thickness of the film is preferably not more than 3 mm. In case of devices with impenetrable surfaces with a thickness of more than 3 mm, the ratios and percentages are indicated for the top 3 mm. Ratios and percentages of penetrable surfaces wherein individual elements on average have a thickness of 3 mm or less are as mentioned herein above. When the individual elements are thicker, the ratios and percentages are for the top 3 mm.

The peptide is preferably linked to the biopolymer through binding of the N-terminal amine group. Other free amine groups of the peptide (if any) such as provided by the side chain of an amino acid such as arginine or lysine can be protected from reacting and physical linkage to the biopolymer prior to the linkage of the peptide to the biopolymer. Linkage via the N-terminal amino group provides additional control over the linkage of the peptide to the biopolymer and thereby linkage of growth-factor to the biopolymer.

In one embodiment, the peptide is provided with a lysine that flanks a binding region of the peptide. This flanking lysine is preferably subsequently used to couple the peptide to the biopolymer. It is preferred that the amino group in the side chain of the terminal lysine is used for the linkage. The lysine is preferably at the N-terminus of the peptide. In one embodiment, the peptide is provided with a terminal lysine. This terminal lysine is preferably subsequently used to couple the peptide to the biopolymer. It is preferred that the amino group in the side chain of the terminal lysine is used for the linkage. The lysine is preferably at the N-terminus of the peptide. It is preferred that the N-terminal amino group of the peptide (of the peptide backbone) is protected from reacting with the biopolymer. It is preferred that the peptide does not contain lysine residues other than the one near the terminus. If amino acid residues with primary amino groups in the side chains are present in the peptide other than the lysine near the terminus, than it is preferred that such primary amino groups are protected. The primary amino group of the side chain of the lysine residue is free for reaction with the biopolymer when the peptide is linked to the biopolymer. In this case the biopolymer preferably comprises the cross-linker. The peptide is preferably linked to the biopolymer via the amino group of the side chain of a lysine. The lysine is preferably a lysine at the end of the peptide. Preferably a terminal lysine, preferably an N-terminal lysine.

A peptide can bind two or more growth factors. Such peptides a peptide can have two or more regions for binding to accommodate this binding of two or more growth factors. In such case the terminal lysine can be at the terminus of the entire peptide or at an internal position flanking a binding region. Such peptides can have the organization: "binding region"-peptide linker-"binding region." The peptide linker can be one or more amino acids of which at least one is a lysine. The organization can also be peptide linker-"binding region"-"binding region." Other arrangement are within the skill of the artisan.

The term "growth factor," as is used herein, refers to a molecule that elicits a biological response to improve tissue regeneration, tissue growth and/or organ function. Preferred growth factors are morphogens. The term "morphogen," as used herein refers to a substance governing the pattern of tissue development and, preferably, the positions of the various specialized cell types within a tissue. A morphogen spreads from a localized source and forms a concentration gradient across a developing tissue. The growth factor may be selected from the group consisting of platelet-derived growth factor (PDGF) AA, PDGF BB, insulin-like growth factors, fibroblast growth factors (FGF), β-endothelial cell growth factor; transforming growth factors (TGF), such as TGFbeta1 (TGFB1), TGFB2, TGFB3, TGFB5; bone morphogenic protein (BMP) 1, BMP2, BMP 3, BMP 4, BMP 7, vascular endothelial growth factor (VEGF), placenta growth factor; epidermal growth factor (EGF), amphiregulin, betacellulin, heparin binding EGF, interleukins (IL)-1, IL-2, IL-3, IL-4, IL-5, IL-6, IL-7, IL-8, IL-9, IL-10, IL-11, IL-12, IL-13, IL-14, IL-15-18, colony stimulating factor (CSF)-G, CSF-GM, CSF-M, erythropoietin, nerve growth factor (NGF), ciliary neurotropic factor, stem cell factor, and hepatocyte growth factor. The term "growth factor," as used herein, includes naturally occurring growth factor receptor antagonists such as angiopoietin-2 and fetuin.

A preferred growth factor belongs to the TGF beta superfamily, including the TGF beta subfamily, the decapentaplegic Vg-related (DVR) related subfamily, and the activin and inhibin subfamily. A preferred growth factor of the TGF beta superfamily is selected from the group consisting of anti-Müllerian hormone, artemin, BMP2, BMP3, BMP4, BMP5, BMP6, BMP7, BMP8A, BMP8B, BMP10, BMP15, growth differentiation factor-1 (GDF1), GDF10, GDF11, GDF15, GDF2, GDF3, GDF3A, GDF5, GDF6, GDF7, GDF8, GDF9, glial cell-derived neurotrophic factor, inhibin alpha, inhibin beta A, inhibin beta B, inhibin beta C, inhibin beta E, left-right determination factor 1, left-right determination factor 2, myostatin, NODAL, neurturin, persephin, TGFB1, TGFB2, TGFB3 and TGFB5.

The term "growth factor binding peptide," as is used herein, refers to a peptide that is able to bind with high affinity to a growth factor, preferably a human growth factor. The binding peptide preferably binds to a growth factor while allowing the growth factor to elicit its biological function to improve tissue regeneration, tissue growth and/or organ function. The binding peptide preferably binds specific to a growth factor. The term "specific," or grammatical variations thereof, refers to the number of different types of growth factors, or their epitopes, to which a particular peptide can bind. The specificity of a peptide can be determined based on affinity. The affinity of a peptide for its target is a quality defined by a dissociation constant (KD). Preferably, KD is less than $10^{-5}$, preferably less than $10^{-7}$, even more preferably, less than $10^{-9}$, and most preferably less than $10^{-10}$. Methods of determining affinity are known in the art, for example, as described in Gilson and Zhou, 2007 (Gilson and Zhou, 2007, Annual Review of Biophysics and Biomolecular Structure 36:21-42).

A growth factor binding peptide preferably binds to a mammalian growth factor, more preferably a human growth factor.

The functionalization of a biomaterial with a growth factor binding peptide allows the capture and presentation of endogenous growth factors to the injured tissue. An endogenous growth factor is non-covalently immobilized on a functionalized biopolymer using a growth factor binding peptide. The immobilized growth factor preferably remains bioactive. The use of such functionalized biopolymers overcomes a need for administration of high amounts of growth factors into an injured tissue for treatment of a tissue pathology or for tissue engineering, preferably to repair a tissue injury. The absence of a need to administer high amounts of growth factors allows spatial control over the presentation of growth factors on implanted devices and will result in less side effects.

A preferred functionalized biopolymer, preferably a polyester, more preferably poly(caprolactone), comprises an amide group by coupling of a ketone or carboxylic acid to a peptide, preferably a growth factor-binding peptide, through an amine in the side group of a N-terminal lysine that is present in the growth factor-binding peptide.

In a preferred biopolymer according to the disclosure, the peptide is present on the biopolymer in a concentration-gradient. The concentration-gradient allows the creation of a zone of high amounts of immobilized growth factor on one side of the biopolymer, and a low concentration area on another side of the polymer. For example, high amounts of immobilized endogenous hVEGF on the outer side of a Collagen Meniscus Implant (CMI) comprising a functionalized biopolymer will match the outer and vascularized area of the meniscus, while a low concentration area on the inner side of the CMI corresponds to the inner, avascular area of the meniscus, with a gradient of immobilized hVEGF between these two areas. The gradient slope can be predetermined by controlling parameters such as peptide concentration or the time for which the biopolymer was allowed to be in contact with the peptide solution during functionalization of the biopolymer (see herein below).

The disclosure further provides a device comprising a biopolymer of the disclosure. The device, preferably an implantable device, may consist partially or completely of functionalized biopolymer composition according to the disclosure. For example, the device, preferably implantable device, may have a core or matrix of any suitable material, which core of matrix is coated with a functionalized biopolymer according to the disclosure. In another example, a core of a functionalized biopolymer according to the disclosure may be coated with any suitable material, for instance, a calcium phosphate material.

A preferred implantable device provides a scaffold for tissue engineering, more preferably a three-dimensional (3D) scaffold for tissue engineering. Scaffolds for tissue engineering can be designed according to specific needs and requirements using standard technology. Typically, the size and shape of the scaffold is a function of the tissue into which the scaffold is to be implanted. Other important and well known parameters include porosity, mechanical properties, pore size and interconnectivity of the pores. Ideally, the size of the scaffold is easy to adjust, either by cutting with a scalpel or by adding smaller pieces together. Furthermore, the filling of the tissue lesion should in the long term result in a normal tissue architecture. Also, the implanted scaffold should not have adverse effect on the newly generated tissue. It is furthermore desirable that the implant is completely remodeled resulting in a scarless regeneration of injured or defected tissue.

A preferred device according to the disclosure should be able to accommodate cells that will aid in the repair of the damaged tissue. In order for cells to be cultured inside and on the scaffold the three-dimensional scaffold should comprise cavities suitable in size in which cells should be able to live, multiply, differentiate and form tissue. In the following such cavities will be referred to as pores. The cell scaffold therefore typically has pores. The presence of pores may also allow for the population of the scaffold by cells originating from surrounding tissues by invasion. Thus, in general the size of the pores will range from about one to ten times the diameter of the cells that are to be accommodated in the scaffold. The size of the pores is thus adapted to the type cell to be accommodated within the three dimensional scaffold considering which type of tissue is to be regenerated or repaired. It is important for the pores to be of a sufficiently large size (sufficient pore volume) so as to allow cells (i.e., living cells) to maintain their shape within the structure. Also, the pores preferably are interconnected and the interconnections are preferably of sufficient size. In relation to access to nutrients and efficient removal of waste products following cellular metabolism a sufficient pore volume is needed. The pores of the cell scaffold preferably have a pore size in the range of from about micron to 1000 micron, such as 50 micron to 1000 micron, for example, 100 micron to 900 micron, such as 200 micron to 600 micron.

Preferred devices include, for example, intervertebral disc replacement devices, spinal fixation systems, facet arthroplasty devices, artificial hips, bone screws, bone plates and rods, prosthetic knee replacements, arterial stents, pacemakers, heart valves, artificial hearts, artificial sphincters, devices comprising sterile non-absorbable implantable tapes made from polyester, such as POLY-TAPE®; a 3-D supportive device comprising a bilayer collagen matrix for adherence of autologous cultured chondrocytes such as Chondro-Gide; an anchor for repair of ligament or tendon injuries such as a Teno Fix tendon-repair device, Tiger Tape and FIBER-TAPE®; and a collagen I-based meniscus implant device such as a Collagen Meniscus Implant (CMI).

A device according to the disclosure preferably enhances attachment of cells and subsequent activation of cells such as fibroblast attachment, their proliferation and production of extracellular matrix; enhances vascularization around the device; provides support for new tissue growth; allows cell-cell communication and access to nutrients, growth factors, and pharmaceutically active agents; prevents cellular activity in case tissue growth is undesirable such as in surgically induced adhesions; guide an appropriate tissue response, meaning that a particular cellular response may be enhanced while others are inhibited; inhibits specific attachment and/or activation of cells, for example, attachment of thrombocytes to a vascular graft; and/or prevents a biological response such as the generation of antibodies against an implanted device.

A preferred device of the disclosure comprises a polyester, preferably poly(caprolactone) biopolymer, that is coupled to a growth factor binding peptide, preferably a TGFB-binding peptide. A preferred TGFB-binding peptide comprises the amino acid sequence N-terminal-LPLGNSH (SEQ ID NO:1), preferably GLPLGNSH (SEQ ID NO:2), more preferably KGLPLGNSH (SEQ ID NO:3). The peptide preferably is coupled to ketone groups of poly(caprolactone) through the amine in the side group of the N-terminal lysine (K). A device comprising a biopolymer that is coupled to a TGFB-binding peptide, preferably a TGFB1 and/or TGFB3 binding peptide, will result in enhanced cell migration, collagen production, cell proliferation and cell-matrix interactions, especially of the musculoskeletal system.

A further preferred device of the disclosure comprises a polyester, preferably poly(caprolactone) biopolymer, that is coupled to a growth factor binding peptide, preferably a VEGF-binding peptide. A preferred VEGF-binding peptide comprises the amino acid sequence N-terminal-SWWAPFH (SEQ ID NO:4), preferably GSWWAPFH (SEQ ID NO:5), more preferably KGSWWAPFH (SEQ ID NO:6). The peptide preferably is coupled to ketone groups of poly(caprolactone) through an amine in the side group of the N-terminal lysine (K). A device comprising a biopolymer that is coupled to VEGF-binding peptide will result in a higher cellularity and in the appearance of blood vessel-like structures around the implanted device.

Yet another preferred device of the disclosure comprises a polyester, preferably poly(caprolactone) biopolymer, that is coupled to a growth factor binding peptide, preferably a BMP-binding peptide, preferably a BMP2 binding peptide. A preferred BMP2-binding peptide comprises the amino acid sequence N-terminal-YPVHPST (SEQ ID NO:7), preferably GYPVHPST (SEQ ID NO:8), more preferably KGYPVHPST (SEQ ID NO:9). The peptide preferably is coupled to ketone groups of poly(caprolactone) through the amine in the side group of the N-terminal lysine (K). A device comprising a biopolymer that is coupled to a BMP-binding peptide, preferably a BMP2 binding peptide, will support osteogenic differentiation and results in a higher recruitment of inflammatory cells, vascularization and matrix deposition.

A preferred device of the disclosure comprises a polyester, preferably poly(ethyleneterephthalate) biopolymer, that is coupled to a growth factor binding peptide, preferably a TGFB-binding peptide. A preferred TGFB-binding peptide comprises the amino acid sequence N-terminal-LPLGNSH (SEQ ID NO:1), preferably GLPLGNSH (SEQ ID NO:2), more preferably KGLPLGNSH (SEQ ID NO:3). The peptide preferably is coupled to ester groups of poly(ethyleneterephthalate) through the amine in the side group of the N-terminal lysine (K). A device comprising a biopolymer that is coupled to a TGFB-binding peptide, preferably a TGFB1 and/or TGFB3 binding peptide, will result in enhanced cell migration, collagen production, cell proliferation and cell-matrix interactions, especially of the musculoskeletal system.

A further preferred device of the disclosure comprises a polyester, preferably poly(ethyleneterephthalate) biopolymer, that is coupled to a growth factor binding peptide, preferably a VEGF-binding peptide. A preferred VEGF-binding peptide comprises the amino acid sequence N-terminal-SWWAPFH (SEQ ID NO:4), preferably GSWWAPFH (SEQ ID NO:5), more preferably KGSWWAPFH (SEQ ID NO:6). The peptide preferably is coupled to ester groups of poly(ethyleneterephthalate) through an amine in the side group of the N-terminal lysine (K). A device comprising a biopolymer that is coupled to VEGF-binding peptide will result in a higher cellularity and in the appearance of blood vessel-like structures around the implanted device.

Yet another preferred device of the disclosure comprises a polyester, preferably poly(ethyleneterephthalate) biopolymer, that is coupled to a growth factor binding peptide, preferably a BMP-binding peptide, preferably a BMP2 binding peptide. A preferred BMP2-binding peptide comprises the amino acid sequence N-terminal-YPVHPST (SEQ ID NO:7), preferably GYPVHPST (SEQ ID NO:8), more preferably KGYPVHPST (SEQ ID NO:9). The peptide preferably is coupled to ester groups of poly(ethyleneterephthalate) through the amine in the side group of the N-terminal lysine (K). A device comprising a biopolymer that is coupled to a BMP-binding peptide, preferably a BMP2 binding peptide, will support osteogenic differentiation and results in a higher recruitment of inflammatory cells, vascularization and matrix deposition.

A device according to the disclosure preferably is designed and manufactured according to Current Good Manufacturing Practice. The device, when used under the conditions and for the purposes intended, will neither compromise the clinical condition or the safety of patients, nor the safety and health of users, provided that any risks which may be associated with their use constitute acceptable risks when weighed against the benefits to the patient and are compatible with a high level of protection of health and safety. Risk analysis, risk evaluation and risk control for risk management in medical device design, development, manufacturing as well as for monitoring the safety and performance of the device after sale, are preferably performed as indicated in ISO 14971:2007.

The disclosure further provides a device according to the disclosure for use as a medicament.

A preferred device according to the disclosure is for use in the treatment of a tissue pathology or for use in tissue engineering, preferably a tissue injury. A most preferred device is an orthopedic medical device. A preferred injured tissue is an injured tendon and/or an injured ligament.

The disclosure further provides a method for treatment of a tissue pathology in a subject, the method comprising (a) providing a device according to the disclosure; (b) introducing the device into tissue of the subject; (c) allowing the device to capture circulating growth factors from the subject.

The disclosure further provides a method for coupling peptides to carbonyl groups of a biopolymer, the method comprising (a) reacting the biopolymer with oxygen plasma;

(b) treating the reacted biopolymer with alkaline, and (c) coupling a peptide to the treated biopolymer using a cross-linker.

The biopolymer, preferably a polyester, is preferably dried prior to reacting the biopolymer with oxygen plasma. The reaction with oxygen plasma preferably is performed at an oxygen pressure of 0.5-2.0 bar, such as, about 1 bar (bar absolute), at a vacuum pressure of 100-500 mbar (absolute), preferably 150-250 mbar; at a current of 20-50 A, such as 35-45 A; and with a treatment time of 30 seconds to 15 minutes, for example, from 1 to 10 minutes, preferably about 5 minutes.

The subsequent reaction of the reacted biopolymer with alkaline preferably is carried out at a pH>9.0. The alkaline, for example, an aqueous 1 M NaOH solution, is incubated with the alkaline for 0.2 to 5 hours, preferably 0.5 to 2 hours, preferably about one hour.

Following one or more rinses, preferably with water, preferably sterile water, the treated biopolymer is preferably dried and incubated with a cross-linker. Preferred reaction conditions include 50 mM of a cross-linker in a slightly acidic buffer, preferably between pH 6 and pH 4, preferably about pH=5, for 0.2 to 5 hours, preferably 0.5 to 2 hours, preferably about one hour. The buffer preferably is or comprises between 10 mM and 1 M, preferably between 20 and 100 mM, 3-(N-morpholino)propanesulfonic acid (MOPS) and/or 2-(N-morpholino)ethanesulfonic acid (MES). A most preferred buffer system is or comprises MES at pH 5.0.

The cross-linker activates the carbonyl groups on the biopolymer after incubation with oxygen plasma and alkaline. A preferred cross-linker is reactive with amines, such as aldehydes, glycidyls, isocyanates, imidates, vinylsulfones, and succinimidyls such as carbodiimides. A more preferred cross-linker is a carbodiimide, preferably 1-ethyl-3-(3-dimethylaminopropyl)carbodiimide (EDC) and/or N-hydroxysuccinimide (NHS). A most preferred cross-linker is a combination of EDC and NHS at about a 1:1 molar ratio.

Following one or more rinses, preferably with water, preferably sterile water, the activated biopolymer is dried and incubated with a peptide. The peptide preferably is present at a concentration of between 0.001 mM and 0.5 M, preferably at 0.01 mM and 0.05 M, more preferably at about 1 mM, in a buffered saline solution such as phosphate-buffered saline. The incubation time of activated biopolymer and a peptide is between 10 minutes and 15 hours, preferably between 1 hour and 10 hours, more preferably about 4 hours.

In a preferred embodiment, the treated biopolymer is provided with a gradient of a peptide, preferably a growth factor binding peptide, by applying different concentrations of the peptide to different sides of the treated biopolymer, and/or by allowing different incubation times for incubating the treated biopolymer with the peptide. For example, a longer incubation period of a certain region of the treated biopolymer with the TGF-β1-binding peptide solution results in a higher surface concentration of the peptide. In a preferred embodiment, the treated biopolymer is submerged in a solution comprising the peptide by dipping the biopolymer in a solution comprising the peptide, whereby a part of the biopolymer that is closest to the peptide solution will be in contact with the peptide for a longer period of time, when compared to a part of the biopolymer that is more remote from the peptide solution. This will result in a higher concentration of the peptide on the part of the biopolymer that is closest to the peptide solution, compared to the part of the biopolymer that is more remote from the peptide solution, thus the peptide is present on the biopolymer in a concentration-gradient.

A preferred biopolymer is a natural or synthetic material that can be used to replace part of a living system or to function in living tissue. The biopolymer comprises at least one carbonyl group, preferably at least one ketone group. The at least one carbonyl group, preferably at least one ketone group or carboxylic acid group is preferably present in each subunit of the polymer. Preferred biopolymers are as describes herein above. A most preferred biopolymer is or comprises a polyester, preferably selected from the group consisting of poly lactic acid, poly-L-lactic acid, polyglycolic acid, polyglycolic lactic acid, poly(amidoamine), poly (caprolactone), polyalkyleneoxide-polyalkylene-terephtalate block copolymer, alginate, poly-N-isopropylacrylamide, preferably poly(caprolactone).

The N-terminus of a peptide that is coupled to a biopolymer preferably lacks a free amino-group, preferably by acetylation. It is further preferred that an amino acid residue comprising an amine group in the side-chain, such as a lysine, histidine or asparagine, most preferably a lysine, is present near the N-terminus of the peptide, most preferred at the N-terminus of the peptide. In a preferred embodiment, the most N-terminal amino acid residue is an amino acid residue comprising an amine group in the side-chain, such as a lysine, histidine or asparagine, most preferably a lysine.

It is further preferred that one or more subterminal amino acid residues are positioned between the N-terminal lysine, histidine or asparagine, and the peptide, preferably the growth factor-binding peptide. The one or more subterminal amino acid residues preferably comprise at least one glycine residue, such as one glycine residue, two glycine residues, three glycine residues, four glycine residues, five glycine residues, or ten glycine residues.

For example, a TGFB1-binding peptide comprising the amino acid sequence LPLGNSH (SEQ ID NO:1), preferably is synthesized as KGLPLGNSH (SEQ ID NO:3), KGGLPLGNSH (SEQ ID NO:10), KGGGLPLGNSH (SEQ ID NO:11) or KGGGGLPLGNSH (SEQ ID NO:12). This peptide is coupled to an oxygen plasma-activated biopolymer through the amine group in the side-chain of the N-terminal lysine (K).

As a further example, a BMP2-binding peptide comprising the amino acid sequence YPVHPST (SEQ ID NO:7), preferably is synthesized as KGYPVHPST (SEQ ID NO:9), KGGYPVHPST (SEQ ID NO:13), KGGGYPVHPST (SEQ ID NO:11), or KGGGGYPVHPST (SEQ ID NO:15). This peptide is coupled to an oxygen plasma-activated biopolymer through the amine group in the side-chain of the N-terminal lysine (K).

Similarly, a VEGF-binding peptide comprising the amino acid sequence SWWAPFH (SEQ ID NO:4), preferably is synthesized as KGSWWAPFH (SEQ ID NO:6), KGGSWWAPFH (SEQ ID NO:16), KGGGSWWAPFH (SEQ ID NO:17) or KGGGGSWWAPFH (SEQ ID NO:18). This peptide is coupled to an oxygen plasma-activated biopolymer through the amine group in the side-chain of the N-terminal lysine (K).

Further growth factor binding peptides are known in the art, for example, as described in U.S. Pat. No. 8,138,140, which is hereby incorporated by reference. Preferred growth factor binding peptides comprise the amino acid sequence KVPPANT (SEQ ID NO:19), KQALTQT (SEQ ID NO:20), WPALFTH (SEQ ID NO:21), PGPTVQG (SEQ ID NO:22), LHYPFMT (SEQ ID NO:23), QQTQAQH (SEQ ID NO:24), PIQPDER (SEQ ID NO:25), PFDPPVR (SEQ ID NO:26), DVSPAYH (SEQ ID NO:27), LRNYSHS (SEQ ID NO:28), VYRHLPT (SEQ ID NO:29), RVSTWDT (SEQ ID NO:30), PAPRWIH (SEQ ID NO:31), RTTSPTA (SEQ ID NO:32), GKYPPTS (SEQ ID NO:33), AWKSVTA (SEQ ID NO:34), and LPSPIQK (SEQ ID NO:35). The peptide preferably is synthesized with lysine, histidine or asparagine, most preferably a lysine, as N-terminal amino acid residue and one or more subterminal amino acid residues between the N-terminal lysine, histidine or asparagine, and the peptide. The one or more subterminal amino acid residues preferably comprise at least one glycine residue, such as one glycine residue, two glycine residues, three glycine residues, four glycine residues, five glycine residues, or ten glycine residues.

Control, nonbinding peptides, may be synthesized, preferably comprising randomized amino acid sequences. For example, a control peptide for the TGFB1-binding peptide comprising the amino acid sequence KGLPLGNSH (SEQ ID NO:3) has the amino acid sequence KGHNLGLPS (SEQ ID NO:36).

Methods to synthesize a peptide, preferably a growth factor binding peptide, as described are known in the art. Synthesis of the peptide may be performed using standard Fmoc-solid phase peptide synthesis in a Syro II MultiSyn-Tech automated peptide synthesizer. For example, a growth factor binding peptide is prepared on Fmoc-Rink 4-methyl-benzhydrylamine (MBHA) resin (MultiSynTech GmBH, 50 mg scale, substitution 0.52 mmol/g), using 0.26 M 2-(1H-benzotriazol-1-yl)-1,1,3,3-tetramethyluronium hexauoro-phosphate (HBTU), 0.52 M of N,N-diisopropylethylamine (DIPEA), 2 M of piperidine and 0.29 M of each amino acid.

The N-termini of a final peptide sequence is preferably acetylated in 16% acetic anhydride, 30% DIPEA and 54% NMP for one hour at room temperature. A peptide may be cleaved from the resin and amino acid side groups deprotected using 95% trifluoroacetic acid, 2.5% triisopropylsilane and 2.5% ultrapure (MILLI-Q®) water. The peptides are preferably collected by precipitation in cold diethyl ether and the organic solvent is removed in a rotatory evaporator. The peptides are preferably re-dissolved in MILLI-Q® water and lyophilized overnight. If required, the resulting products can be purified using standard preparative HPLC methods.

The disclosure further provides the use of oxygen plasma for coupling a peptide to one or more carbonyl groups of a biopolymer, preferably one or more ketone groups or carboxylic acid groups of a biopolymer. Oxygen plasma is used for surface activation with carbonyl groups, preferably aldehyde, ketone, ester, carboxylic acid, carboxylate ester, and/or amide groups, most preferably ketone groups, of a non-functionalized biopolymer, such that an amino group of a peptide can be coupled to the activated carbonyl groups, preferably activated ketone groups, preferably by use of a cross-linker. The treatment with oxygen plasma is preferably followed by a treatment with base/alkaline to introduce/expose/generate carboxyl groups, prior to coupling of the cross-linker as detailed elsewhere herein.

The biopolymer preferably is of a natural origin, such as collagen, chitosan, dextran, hyaluronic acid, heparin, heparin, polysaccharide such as alginate (or alginic acid), hyaluronic acid, agarose etc., polynucleotide, polypeptide, starch, and/or combinations thereof. Synthetic biopolymers include poly lactic acid, poly-L-lactic acid, polyglycolic acid, polyglycolic lactic acid, poly(amidoamine), poly (caprolactone), polyalkyleneoxide-polyalkylene-terephtalate block copolymer, poly-N-isopropylacrylamide, polyurethane, poly-acrylate, polyesters, polystyrene, polycarbonate, polyethyleneterephtalate (PET), polybutyleneterephtalate (PBT), polyethyleneoxide (PEO), polyethersulfone (PES), polytetra-fluoroethylen (PTFE), polytrimethylenecaprolactone (PTMC), polyanhydride, polylactic acid (PLA), poly (ortho)ester and polyphosphazene and/or combinations thereof.

DETAILED DESCRIPTION

Examples

Figure 1:
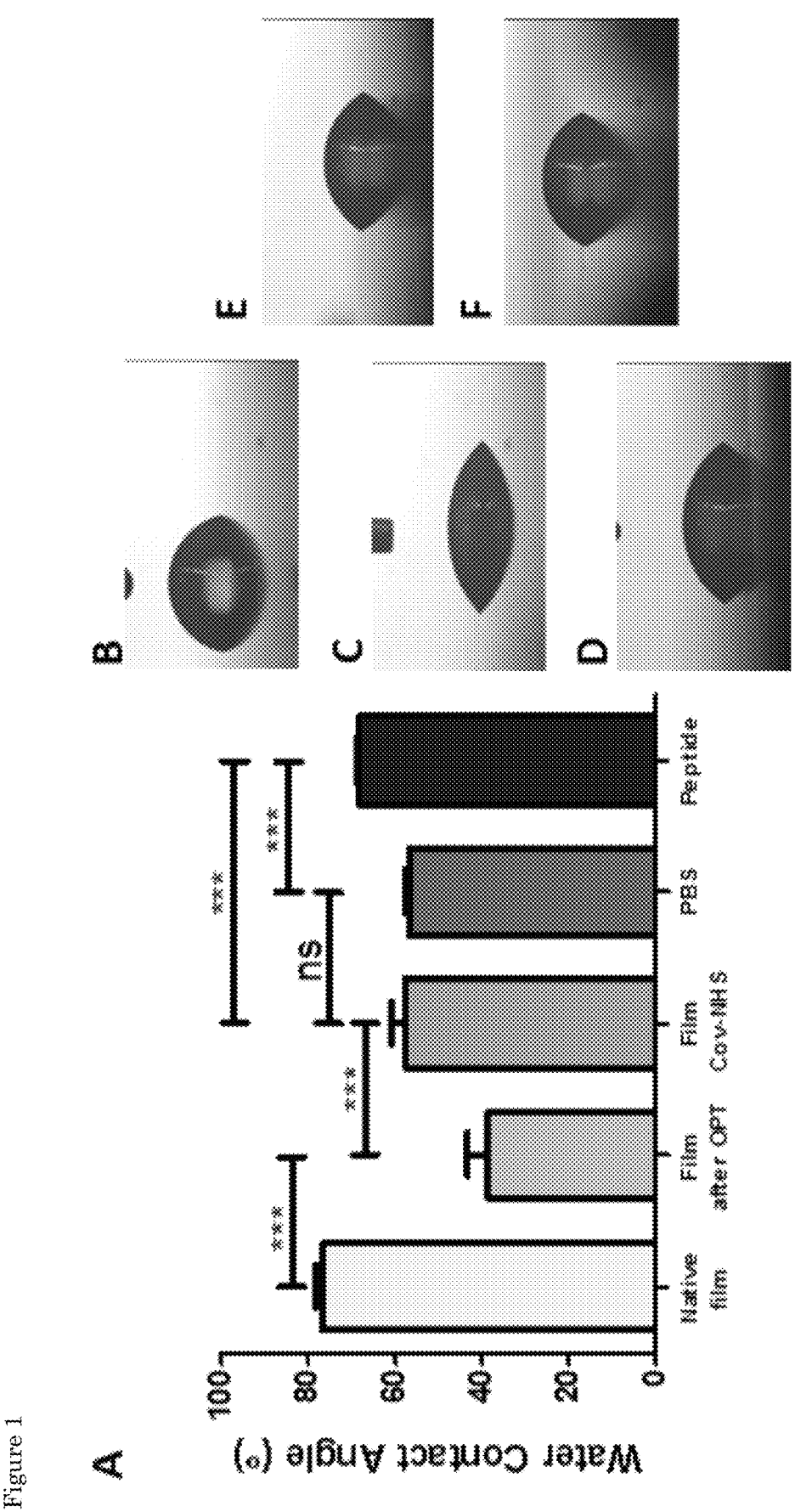
FIG. 1. (A) Water contact angle measurements of the films during the chemical functionalization procedure. (B) Native films are the PCL films without any chemical modification; (C) films after OPT are the native PCL films exposed for 5 minutes to oxygen plasma; (D) Films Cov-NHS are the films with amine reactive esters after 1 hour incubation with NHS/EDC; (E) PBS are the films with reactive amine esters incubated during 4 hours with PBS; (F) Peptide are the films with reactive amine esters incubated during 4 with a 1 mM of peptide in PBS. *** $p<0.0001$ (two-tailed unpaired t-test). The data represent the mean±SD of 2 measurements per sample (n=3).

Example 1: TGF-β1 Activation in Hamstring Cells Through GFs Binding Peptides on Polymers

Materials and Methods

Peptide Synthesis and Purification

The synthesis of the peptides sequences was performed using standard Fmoc-solid phase peptide synthesis in a Syro II MultiSynTech automated peptide synthetizer. The TGFB1 binding and scrambled peptide with sequences KGLPLGNSH (SEQ ID NO:3) and KGHNLGLPS (SEQ ID NO:36), respectively, were prepared on Fmoc-Rink 4-methylbenzhydrylamine (MBHA) resin (Multisyntech GmbH, 50 mg scale, substitution 0.52 mmol/g), using 0.26 M of N,N,N',N'-Tetramethyl-O-(1H-benzotriazol-1-yl)uronium hexafluorophosphate (HBTU), 0.52 M of N,N-Diisopropylethylamine (DIPEA), 2 M of piperidine and 0.29 M of each amino acid. The N-termini of the final peptide sequences were acetylated manually in 15.6% acetic anhydride, 29.9% DIPEA and 54.5% 1-Methyl-2-pyrrolidinone (NMP) for one hour at room temperature. The peptides were cleaved from the resin and amino acid side groups were deprotected using 95% trifluoroacetic acid, 2.5% triisopropylsilane and 2.5% MILLI-Q® water. The peptides were then collected by precipitation in cold diethyl ether and the organic solvents were removed in a rotatory evaporator. The peptides were redissolved in MILLI-Q® water and lyophilized overnight. The resulting products were purified using standard preparative HPLC methods. MS (ESI): m/z=964.1 [M+H]+ (calculated 963.1 for C42H70N14O12) for KGLPLGNSH (SEQ ID NO:3). MS (ESI): m/z=964.6 [M+H]+ (calculated 963.1 for C42H70N14O12) for KGHNLGLPS (SEQ ID NO: 36).

Preparation of Peptide Displaying PCL Films

A 12.5% (w/v) solution of PCL in chloroform was prepared and homogenized by sonication. When the solution was completely homogeneous, PCL films were prepared by casting in a petri dish, presilanized with an PFDTS anti-sticky layer (1H,1H,2H,2H-Perfluorodecyltrichlorosilane, 97%, ABCR GmbH). Upon solvent evaporation, the polymer was melted and allowed to solidify again. The polymer was then cut in circular films with a diameter of 21 mm in order to fit inside the wells of a 12-well plate. The individual circular films were extensively washed with demi-water and MILLI-Q® water and dried with a N2 stream. The dried films were exposed to oxygen plasma for 5 minutes (at an oxygen pressure of 1.0 bar, a vacuum pressure of 200 mbar and a current of 40 A) and subsequently immersed in a 1 M NaOH solution for one hour with gentle agitation. PCL films were then washed and dried as mentioned above, and incubated with a solution of 50 mM 1:1 NHS/EDC in MES buffer for one hour with agitation. PCL films were washed and dried again as mentioned before and incubated with 1 mM of the peptide in phosphate buffered saline (PBS) during 4 hours with agitation. Films were then washed extensively with PBS and sterilized by incubating the films overnight in a solution of 10% penicillin/streptomycin (Life Technologies) in PBS prior to cell seeding.

Water Contact Angle Measurements

The wettability of the PCL films was determined by a drop contact angle system (Kruss Contact Angle Measuring System G10). The contact angle was measured and calculated using Drop Analysis software. All reported contact angles are the average of n=6 measurements. MILLI-Q® water was used to measure the contact angle of the films.

TGFB1 Binding and Immunofluorescence

The PCL films were incubated with 1 microg/mL of hTGFB1 (Peprotech) in 4 mM hydrochloric acid (HCl) containing 1 mg/mL (bovine serum albumin) BSA for one hour with gentle agitation. The films were then washed three times with 1 mM phosphate buffered saline TWEEN®20 (PBST) for ten minutes each time and then with PBS alone for another ten minutes. Next the films were blocked for one hour with PBS containing 1% (w/v) BSA and subsequently washed as described before. Afterwards, the films were incubated with a 5 microg/mL solution of the primary antibody (mouse monoclonal anti-human TGFB1, R&D systems) in blocking solution during one hour with agitation. The films were washed as mentioned above and then incubated with a 4 microg/mL solution of the secondary antibody (goat anti-mouse ALEXA FLUOR® 546, Invitrogen) in PBS containing 1% w/v BSA for one hour with gentle agitation. Before using for fluorescence microscopy the films were washed three times with 1 mM PBST for ten minutes each washing, rinsed three times with PBS and dried under a N2 stream. For cell experiments, the sterile films were washed three times with PBS and incubated with hTGFB1 in sterile 4 mM HCl containing 1 mg/mL BSA during one hour with gentle agitation. Subsequently, the films were extensively washed with TBST (0.1%) and PBS to remove any traces of the washing buffer prior to cell seeding.

In Vitro Quantification of Bound TGFB1

Bound hTGFB1 was quantified by incubating the films with 1 microg/mL of TGFB1 in 4 mM HCl containing 1 mg/mL BSA during one hour with gentle agitation. The supernatant was collected and the films were washed for thirty minutes with TBST (0.1% (v/v)). The buffer was then collected and mixed with the supernatant previously collected. The collected solutions were analyzed for unbounded hTGFB1 by an anti-human TGFB1 ELISA kit (Abcam AB100647), according to the manufacturer's instructions. The amount of immobilized hTGFB1 was calculated based on the difference between the incubation solution and the unbounded hTGFB1 quantified by the ELISA kit.

Cell Culture

Mink Lung Epithelium Cells (MLEC—a kind gift from Daniel's Rifkin lab) were expanded in Dulbecco's modified eagle medium (DMEM, Life Technologies, Gaithersburf, MD) supplemented with 10% Fetal Bovine Serum (FBS, Life Technologies), 100 U/mL penicillin (Life Technologies), 100 microg/mL streptomycin (Life Technologies) and 2 mM L-glutamine (Life Technologies). Cells were grown at 37° C. in a humid atmosphere with 5% CO2. The medium was refreshed twice per week and cells were used for further subculturing or cryopreservation on reaching near confluence. This cell line, firstly described by Rifkin et al. (1994), expresses luciferase under the control of a TGF target gene (Plasminogen activator inhibitor 1, PAI-1 promoter) (Abe et al., 1994, Analytical Biochemistry 216:276-284). Hamstring cells (HT22, P3-4) were isolated using outgrowth procedure as previously described (Ghebes et al., 2015, Journal of Tissue Engineering and Regenerative Medicine doi: 10.1002/term.2009), cultured in alpha-minimal essential medium (alphaMEM, Life Technologies) with 10% FBS (Gibco, Life Technologies), 100 U/mL penicillin, 100 microg/ml streptomycin and 0.2 mM L-ascorbic acid-2-phosphate magnesium salt (ascorbic acid, Life Technologies). Cells were grown at 37° C. in a humid atmosphere with 5% CO2. The medium was refreshed twice per week, and cells were used for further subculturing or cryopreservation on reaching near confluence. Experiments with hamstring cells were performed with cells until passage 4.

Luciferase Assay

MLECs were seeded at 64000 cells/cm$^2$ and allowed to attach overnight at 37° C. in a 5% CO2 incubator. The medium was then replaced by DMEM without FBS and cells incubated for an additional period of 24 hours. Cells were lysed and the luciferase quantified according to the manufacturer's protocol (Promega, E4530). Luciferase values were normalized for DNA content quantified by CyQuant Cell proliferation assay (Invitrogen).

Smad Translocation Assay

To assess the cellular localization of Smad2/3 complex, hamstring cells were seeded at 10000 cells/cm$^2$ and incubated for 24 hours at 37° C. in a 5% CO2 incubator. Samples were washed with PBS and cells fixed with 4% (w/v) paraformaldehyde/PBS for 15 minutes at room temperature. Samples were washed with PBS and incubated with a filtered solution of 0.3% (w/v) Sudan Black in 70% ethanol for 30 minutes with gentle agitation. Films were washed three times with PBS for 5 minutes per washing and the cell membrane was permeabilized with 0.1% Triton X-100/PBS for 15 minutes. After rinsing three times with PBS, films were blocked with a solution of 2% (w/v) BSA in 0.1% TRITON® X-100 in PBS at room temperature for one hour with gentle agitation. Monoclonal mouse anti-Smad2/3 (clone 18, BD Bioscience, 1:200) was incubated overnight at 4° C. in blocking solution with gentle agitation. The secondary antibody goat anti-mouse ALEXA FLUOR® 594 (DAKO, 1:200) was incubated at room temperature for one hour in blocking solution. Nucleic acids were stained with DAPI (Life Technologies, 1:100) for 15 minutes at room temperature. Samples were washed three times with 0.1% TRITON® X-100/PBS for 5 minutes, rinsed with PBS and dried with a N2 stream before mounting.

Gene Expression Analysis

For gene expression analysis hamstring cells were seeded on films at 5000 cells/cm$^2$ and cultured for 3, 7 and 14 days in culturing medium. Upon which RNA was isolated using trizol combined with a NUCLEOSPIN® RNA II kit (Bioke). 1 μg of RNA was used for synthesize cDNA using SensiFast kit (Bioline). iQ SYBR Green Supermix (Bio-rad) was used for quantitative polymerase chain reaction (qPCR) on a MJ Mini™ thermal cycler (Bio-rad). Gene expression was normalized for the housekeeping gene B2M. The primer sequences used are as follows: collagen I forward: 5'-GTC ACC CAC CGA CCA AGA AAC C-3' (SEQ ID NO:37), reverse: 5'-AAG TCC AGG CTG TCC AGG GAT G-3' (SEQ ID NO:38); collagen III forward: 5'-GCC AAC GTC CAC ACC AAA TT-3' (SEQ ID NO:39), reverse: 5'-AAC ACG CAA GGC TGT GAG ACT-3' (SEQ ID NO:40); sox9 forward: 5'-ATC CGG TGG TCC TTC TTG TG-3' (SEQ ID NO:41), reverse: 5'-TGG GCA AGC TCT GGA GAC TTC-3' (SEQ ID NO:42); aggrecan forward: 5'-AGG CAG CGT GAT CCT TAC C-3' (SEQ ID NO:43), reverse: 5'-GGC CTC TCC AGT CTC ATT CTC-3' (SEQ ID NO:44); B2M forward: 5'-ACA AAG TCA CAT GGT TCA CA-3' (SEQ ID NO:45), reverse: 5'-GAC TTG TCT TTC AGC AAG GA-3' (SEQ ID NO:46).

Collagen Quantification

For the analysis of the amount of collagen produced, hamstring cells were seeded on films at 5000 cells/cm$^2$ and cultured for 7 and 14 days in culture medium. Hydroxyproline quantification was used as a direct method for the determination of the collagen content on the samples. Cells were washed with PBS, lysed with 12 N HCl and scratched from the films. The lysate was transferred to a pressure tight Teflon capped vial and hydrolyzed at 120° C. for three hours. After hydrolyzation the amount of hydroxyproline was quantified using Hydroxyproline Colorimetric Assay Kit (Biovision) according to manufacturer's instructions.

Subcutaneous Implantation Rat Model

All the animal experiments were approved by the animal research ethics committee of The Chinese University of Hong Kong. Eight 12-week-old Sprague Dawley male rats were used in this study. The rats were anesthetized by intraperitoneal injection of 10% ketamine/2% xylazine (Kethalar, 0.3 ml: 0.2 ml) and sedation maintained by intramuscular injection of 10% ketamine (Sigma Chemical CO, St. Louis, MO). Subcutaneous implantation of PCL was performed. In brief, once the animals were anesthetized, shaved and washed. Two incisions were made and native PCL and PCL functionalized with a TGFB1 binding peptide were inserted into the pockets and fixed to the fascia. Skin wound was then closed with suture. At day 3 and day 7 post implantation, animals were sacrificed and samples were harvested. Samples from the subcutaneous rat model were harvested at day 7 post implantation and rinsed with PBS. Harvested samples were fixed with 10% buffered formalin for 10 minutes and further permeabilized with PBST for 15 minutes. Samples were then washed with PBS and blocked with 1% (w/v) BSA for 1 hour in a shaker. Next, the samples were washed three times with PBST during 10 minutes each washing and incubated with a dilution of 1:100 of the primary antibody (rabbit polyclonal anti TGF-fÁ1, Santa Cruz Biotechnology) overnight at 4° C. After primary antibody incubation, samples were washed with PBST and incubated with a dilution of 1:100 of the secondary antibody (goat anti rabbit IgG-PE, Santa Cruz Biotechnology) during one hour at room temperature. Samples were washed with PBST before imaging.

Histology

At day 3 and day 7 post implantation, PCL implants and its surrounding tissues were harvested and rinsed with PBS. Harvested samples were fixed with 10% buffered formalin overnight and embedded in paraffin. Five micron-thick paraffin sections along transverse plane were collected. Hematoxylin and Eosin (H&E) stained sections were examined under light microscopy (Leica Microsystems, Wetzlar, Germany) and scored.

Statistical Analysis

The data were analyzed using Student's paired t-test, one-way analysis of variance followed by a Tukey's multiple comparison test ($p<0.05$) or two-way analysis of variance, and values represent the mean and standard deviation of three independent measurements.

Results

Production of PCL Films Presenting TGFB1 Binding Peptides

In order to immobilize hTGFB1 on the PCL film, a previously reported TGFB1 binding peptide sequence LPLGNSH (SEQ ID NO:1) was synthesized and equipped with an extra lysine and a glycine at the N-termini. The extra glycine functions as a spacer between the film and the active sequence involved in the affinity to hTGFB1 whereas the extra lysine provides an amine group to covalently immobilize the peptide to the film. The N-termini of the peptide was acetylated and consequently the covalent immobilization of the peptide to the film was solely achieved through the free amine from the side group of lysine. To covalently bind the peptide to the film, the native PCL films were firstly treated with oxygen plasma to introduce carboxylic acid groups on the surface. Next, the carboxylic acids were activated with EDC/NHS treatment leading to the formation of amine reactive esters that were used for the covalent immobilization of the TGFB1 binding via the free amine present in the side chain of the lysine amino acid. Surface wettability was used to keep track of the chemical modifications during the immobilization procedure (FIG. 1). After exposing the native PCL films to oxygen plasma for 5 minutes the hydrophobicity of the surface decreased to $38\pm2°$ ($p<0.0001$) whereas NHS/EDC treatment led to an increase of $19\pm2°$ ($p<0.0001$). Films with the amine reactive ester were then incubated with a PBS solution alone or with 1 mM of the TGFB1 binding peptide in PBS. As expected, when the films with the NHS-activated acids were incubated with PBS no significant change in the water contact angle was observed. In contrast, when the films were incubated with a solution of PBS containing the TGFB1 binding peptide, a further increase of $11\pm1°$ ($p<0.0001$) in contact angle of the surface was observed which indicates that the peptide was attached to the films.

TGF-β1 Immobilization on the Functionalized PCL Films

Figure 2:
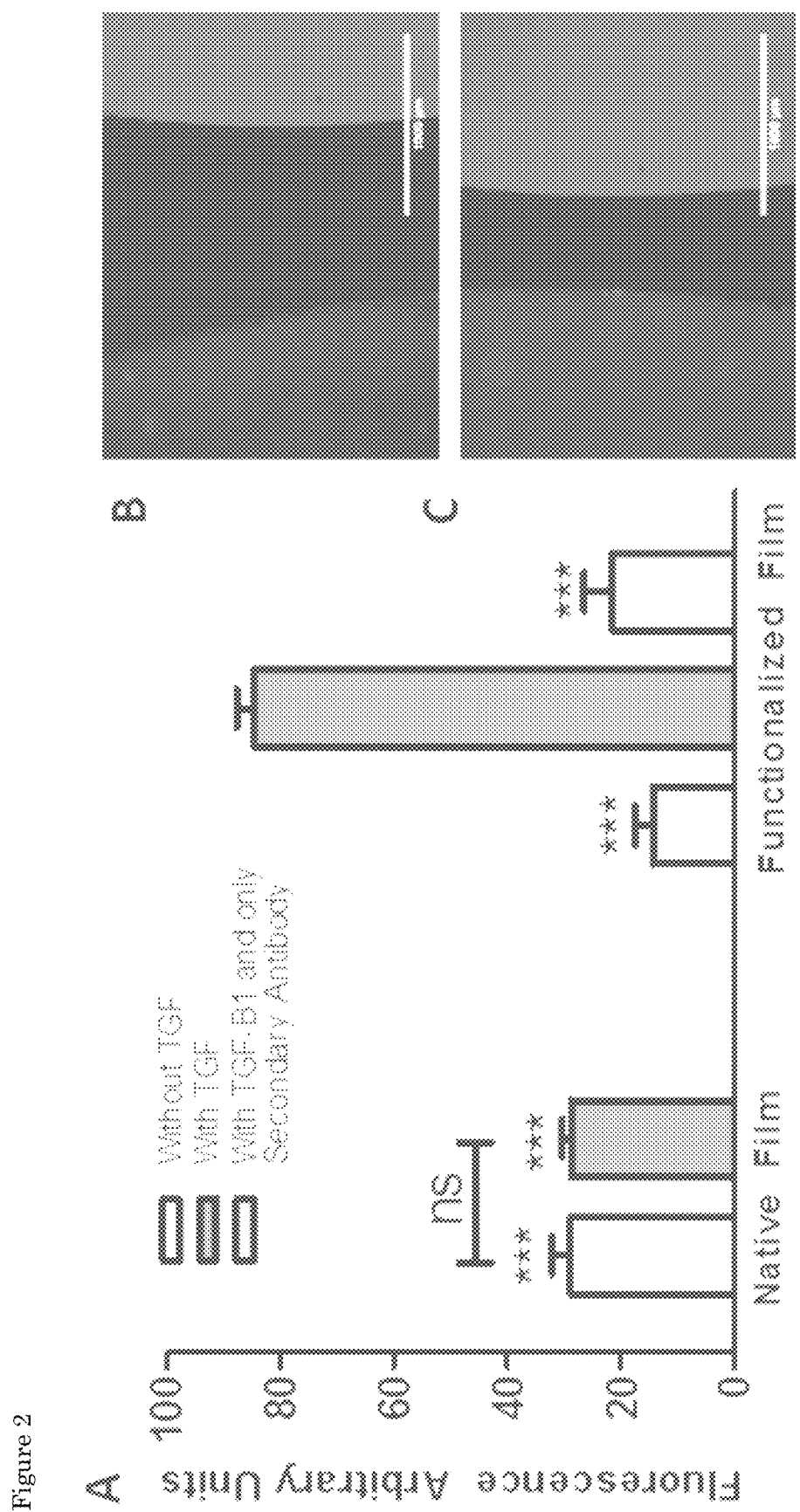
FIG. 2. (A) Fluorescence quantification of the immuno-chemistry assay against hTGFB1 immobilized on the films. The data represents mean±SD of 3 measurements per sample (n=2). *** $p<0.0001$ (two-tailed unpaired t-test) with functionalized films incubated with hTGFB1 and immunochemistry performed with primary and secondary antibody. (B) Fluorescence image of the functionalized film without hTGFB1 incubation (left) vs functionalized film with hTGFB1 incubation (right) (bar: 1000 μm). (C) Fluorescence image of the native film with hTGFB1 incubation (left) vs functionalized film with hTGFB1 incubation (right) (bar: 1000 μm).

To confirm the attachment of the peptide to the films and the subsequent binding of the GF to the functionalized films, immunostaining was performed on both native and functionalized films incubated either with or without hTGFB1. The results showed a statistically significant increase in functionalized films incubated with the hTGFB1 (FIG. 2, Panel A; $p<0.0001$). In addition, the immunostaining demonstrated a homogenous distribution of the GF within the film (FIG. 2, Panels B and C). Besides showing a specific interaction of hTGFB1 with the peptide, the absence of unspecific interaction of the primary or secondary antibody with the functionalized film was also demonstrated. Given the fact that incubating the native PCL film with hTGFB1 did not lead to a significant increase in the fluorescence intensity, it was concluded that no unspecific interactions occurred between hTGFB1 and native films. To summarize, the fluorescence signal reported for the functionalized films is the results of a specific binding of hTGFB1 to the TGFB1 binding peptide attached to the films.

Figure 3:
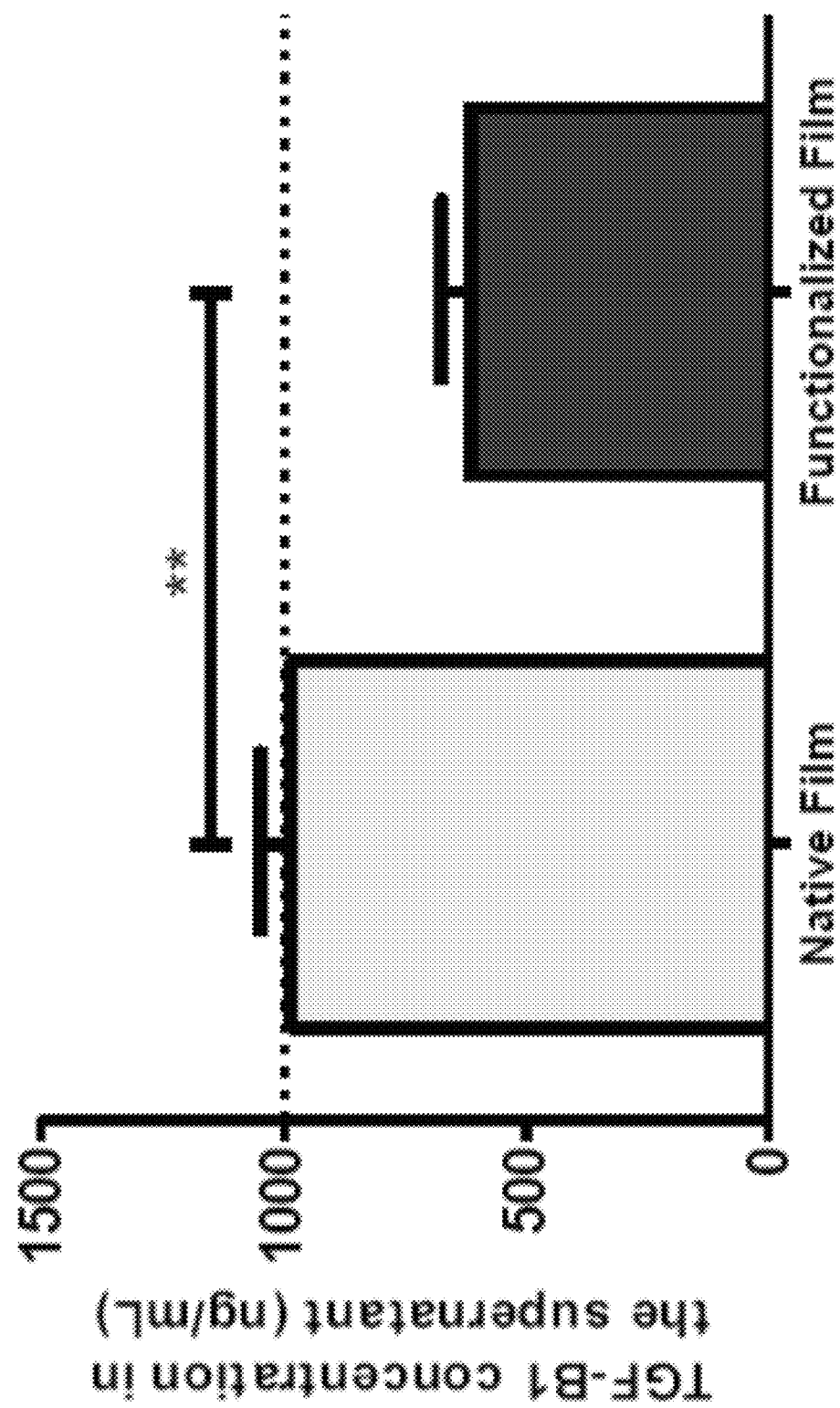
FIG. 3. Quantification of the amount of immobilized hTGFB1 by the TGFB1 binding peptide was analyzed by an ELISA assay against hTGFB1. ** $p<0.005$ (two-tailed unpaired t-test) between native film and functionalized film. Dashed line represents the hTGFB1 concentration of the incubation solution. The data is represented as mean±SD of 2 measurements per sample (n=3).

To estimate the amount of hTGFB1 bound to the TGF-β1 binding peptide functionalized film, an ELISA assay against hTGFB1 was performed (FIG. 3). The results show that no GF remains on the native film after one-hour incubation, which is in agreement with the results from the immunostaining (FIG. 2). On the other hand, 37% of the initial amount of hTGFB1 (1 microg/mL) remained on the films functionalized with the TGFB1 binding peptide giving a surface concentration of $123\pm16$ ng/cm2 of hTGFB1 ($p<0.005$). The ELISA assay further confirms the results obtained in the immunostaining indicating that it is possible to specifically immobilize hTGFB1 on the film functionalized with a TGFB1 binding peptide sequence.

Bioactivity of the Immobilized TGFB1 in a TGFB1 Reporter Cell Line

Figure 4:
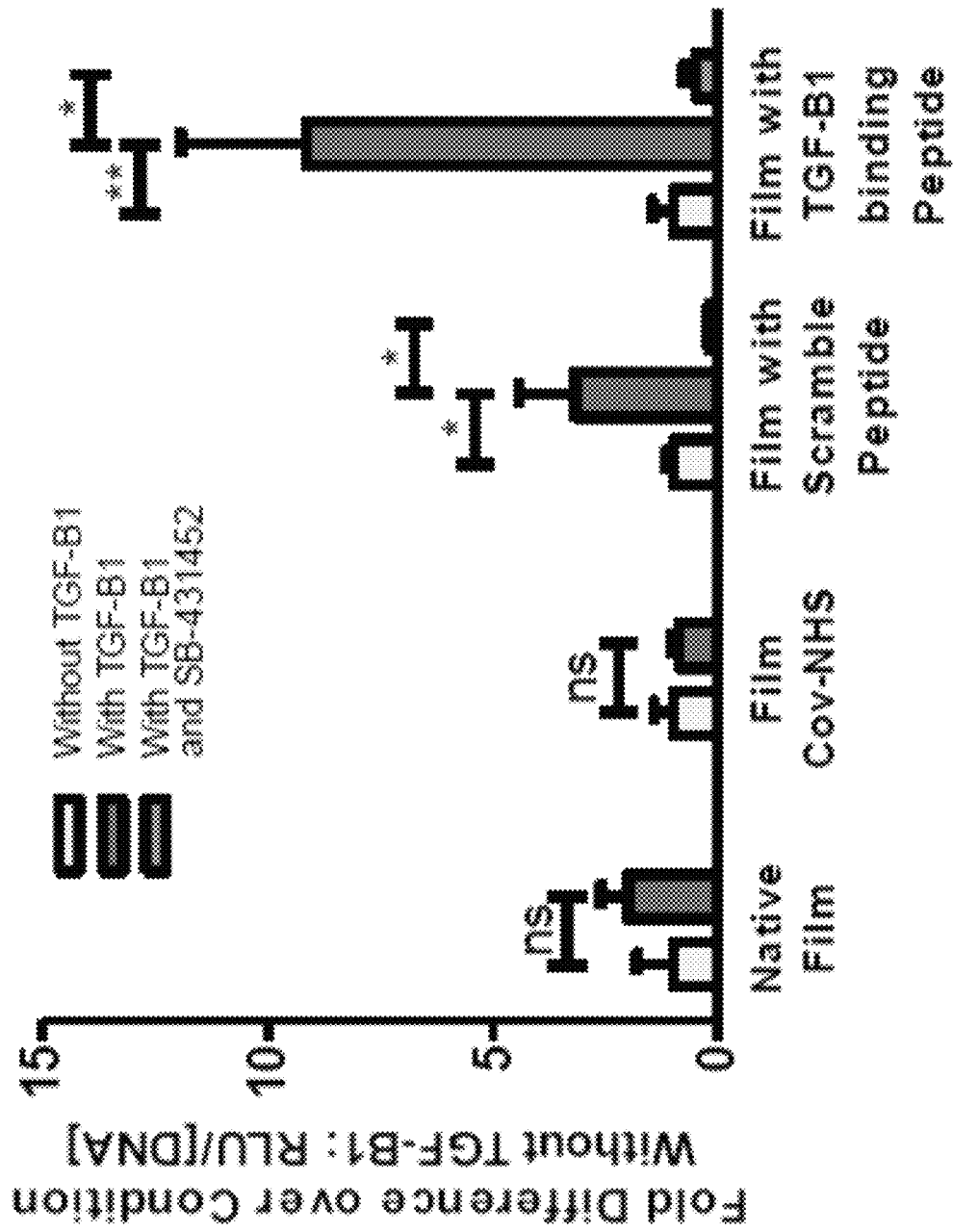
FIG. 4. Effect of immobilized hTGFB1 on the expression of luciferase by a TGFB1 reporter cell line. Luciferase values were corrected for the amount of DNA and normalized to the condition without incubation of hTGFB1 prior to cell seeding. * $p<0.05$ and ** $p<0.01$ (two-tailed unpaired t-test). The data is represented as mean±SD of 2 measurements per sample (n=3).

A TGFB1 reporter cell line was used in order to assess if the immobilized GF retained its bioactivity. The films were first incubated with a solution containing 0 or 50 ng of hTGFB1, the cells seeded in the absence or presence of 10 M of a specific TGF-β1 inhibitor (2-(5-benzo[1,3]dioxol-5-yl-2-tert-butyl-3H-imidazol-4-yl)-6-methylpyridine hydrochloride; SB-431452; GlaxoSmithKline) and the amount luciferase quantified and normalized to the amount of DNA (FIG. 4). When both native and Cov-NHS films were incubated with hTGFB1 before cell seeding no increase in the luciferase activity was observed when compared with the values obtained for the same films without hTGFB1 incubation. However, when the films functionalized with a TGFB1 binding peptide were incubated with hTGFB1 before cell seeding a $9\pm3$ fold increase in luciferase activity was observed ($p<0.01$). To demonstrate that the interaction of the GF was specifically mediated by the TGF-binding peptide, a scrambled peptide sequence was included as a control. When these films were incubated with hTGFB1 before cell seeding an increase of $3\pm1$ in luciferase activity was also observed ($p<0.05$). The inclusion of a TGFB1 inhibitor completely suppressed the luciferase activity observed ($p<0.05$).

Figure 5:
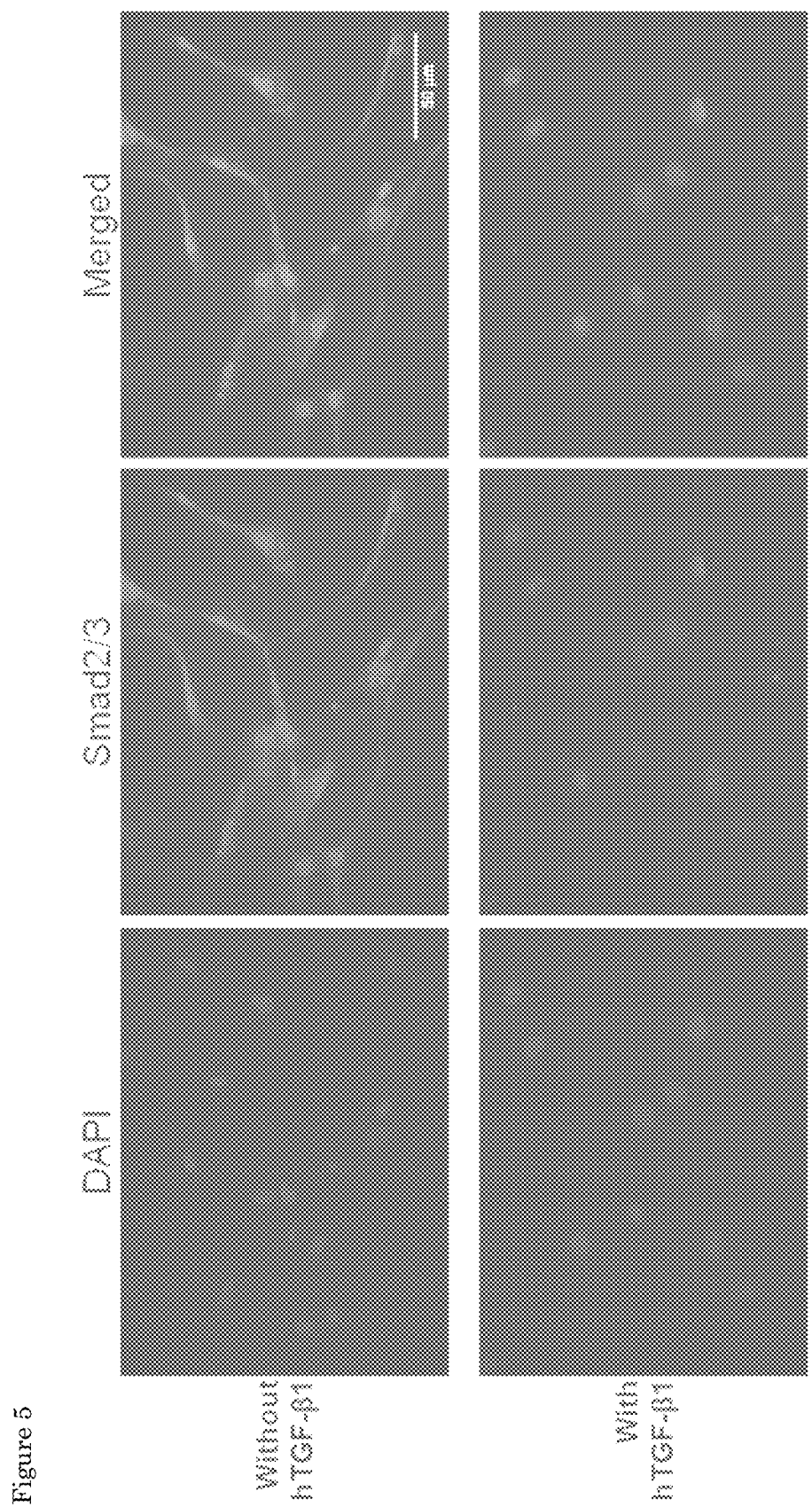
FIG. 5. Immobilized hTGFB1 induces translocation of Smad2/3 into the nucleus in human-derived hamstring cells. (Scale bar: 50 μm).

Immobilized hTGFB1 Activates the TGF Pathway Via Smad2 3 in Human Hamstring Cells The bioactivity of the immobilized hTGFB1 was evaluated in human hamstring-derived cells, which were isolated from the hamstring graft—the most commonly used graft for ACL reconstruction. To that end, the intracellular localization of the SMAD2/3 complex, a key player in the TGFB1 signaling pathway, was monitored (FIG. 5). Upon phosphorylation, this complex binds to SMAD4 and translocates from the cytoplasm into the nucleus activating the transcription of TGF-β1 target genes (Nakao et al., 1997, The EMBO Journal 16:5353-5362). When the cells were seeded on functionalized films without pre-incubation with hTGFB1 the SMAD2/3 complex was found both in the cytoplasm and in nucleus. In contrast, when they were seeded on the functionalized films previously incubated with hTGFB1, the SMAD2/3 complex was mostly detected in the nucleus clearly demonstrating a TGFb1-mediated translocation mechanism.

Immobilized hTGFB1 Specifically Activates TGFB1 Target Genes

Figure 6:
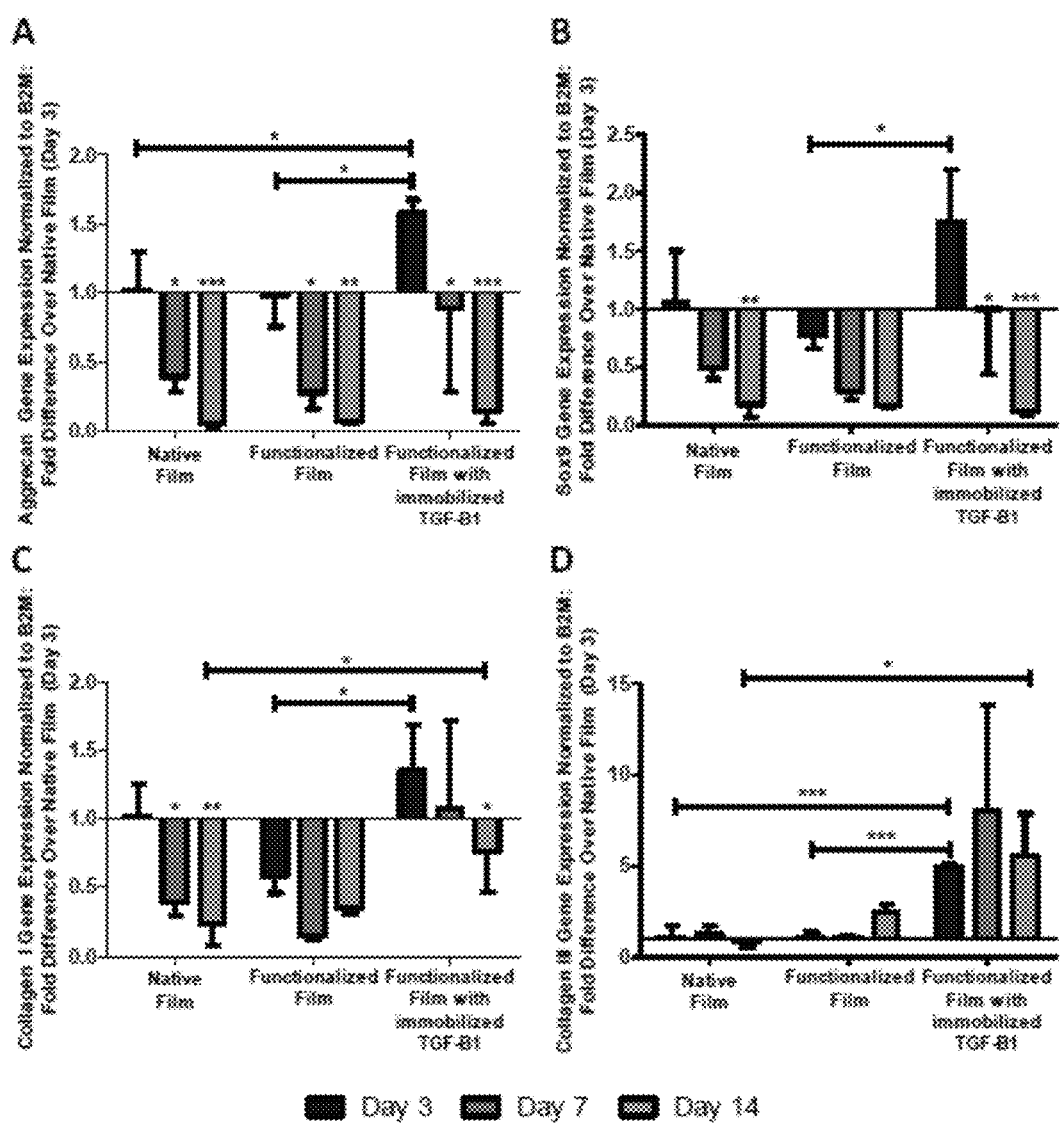
FIG. 6. Immobilized hTGFB1 induces expression of TGFB1 target genes in human-derived hamstring cells. qPCR analysis of (A) Aggrecan (B) Sox9 (C) Collagen type I (D) Collagen type III. * $p<0.05$;  $p<0.01$; * $p<0.0001$ with two-way Anova for analysis of gene expression across time and one way Anova with Tukey's post-hoc test for analysis of gene expression between all conditions at a particular time point. The data is represented as mean±SD of triplicates.

In tissue healing, various components of the extracellular matrix (ECM), such as collagens and proteoglycans, are responsible to restore tissue homeostasis. Given that the immobilized hTGFB1 promotes SMAD2/3 translocation to the nucleus, the expression of TGFB1 target genes in human-derived hamstring cells was evaluated. The expression of collagen type I and III, which are the major components of tendon and ligaments, aggrecan (Acan), which is a component of ECM and Sox9 a chondrogenic differentiation marker were studied by qPCR (FIG. 6). The results show that the expression of collagen type I, Acan and Sox9 is similar in time. A statistically significant upregulation was observed at day 3 for the three genes on the functionalized films with immobilized hTGFB1. For later time points (day 7 and 14) a downregulation was observed in the expression of these genes for all conditions tested. In the case of collagen type III an upregulation was observed in the case of functionalized films with immobilized hTGFB1, which, in contrast to the previously mentioned genes, was maintained in time. This data shows that the immobilized hTGFB1 is regulating the transcription of TGF-β1-target genes as previously reported (Wilson et al., 2009, Tissue Engineering: Part A 15:1513-1522; Furumatsua et al., 2009, The Int. J. Biochem. & Cell Biol. 41:1198-1204; Reed et al., 2005, J. Cell Physiol. 158:169-179; Kenyon et al., 2003, Thorax 58:772-777). Interestingly, in the case of collagen type III, this activation is sustained without having to add exogenous hTGFB1 to the cells.

Effects of Immobilized hTGFB1 on Endogenous Collagen Production

Figure 7:
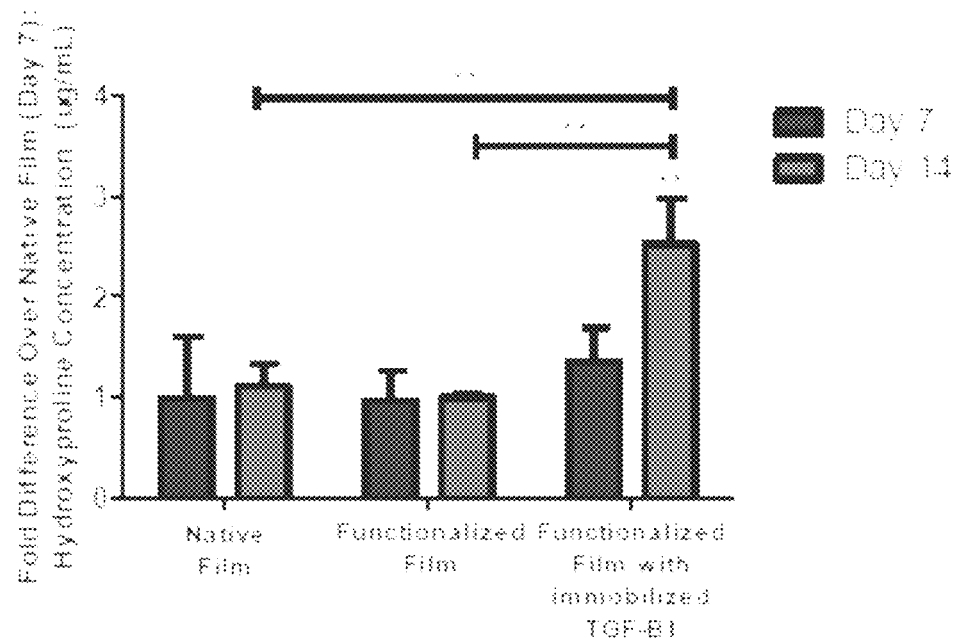
FIG. 7. Immobilized hTGFB1 induces synthesis of collagen in human-derived hamstring cells. ** $p<0.01$ with two-way Anova for analysis of collagen production across time and one way Anova with Tukey's post-hoc test for analysis of collagen production between all conditions at a particular time point. The data is represented as mean±SD of triplicates.

In order to check whether the upregulation observed for collagen at the gene level was effectively leading to an upregulation of the protein, the total amount of hydroxyproline was quantified as a direct measure of collagen protein (FIG. 7).

No differences were observed in the amount of collagen between day 7 and day 14 for the films where no immobilized hTGFB1 was present. In contrast, when the cells were seeded on functionalized films with immobilized hTGFB1 a 2.5±0.4 fold increase was observed after 14 days for the amount of collagen (p<0.01). This data shows that the upregulation seen at the RNA level for collagen genes is accompanied by an upregulation in the amount of collagen protein.

Figure 8:
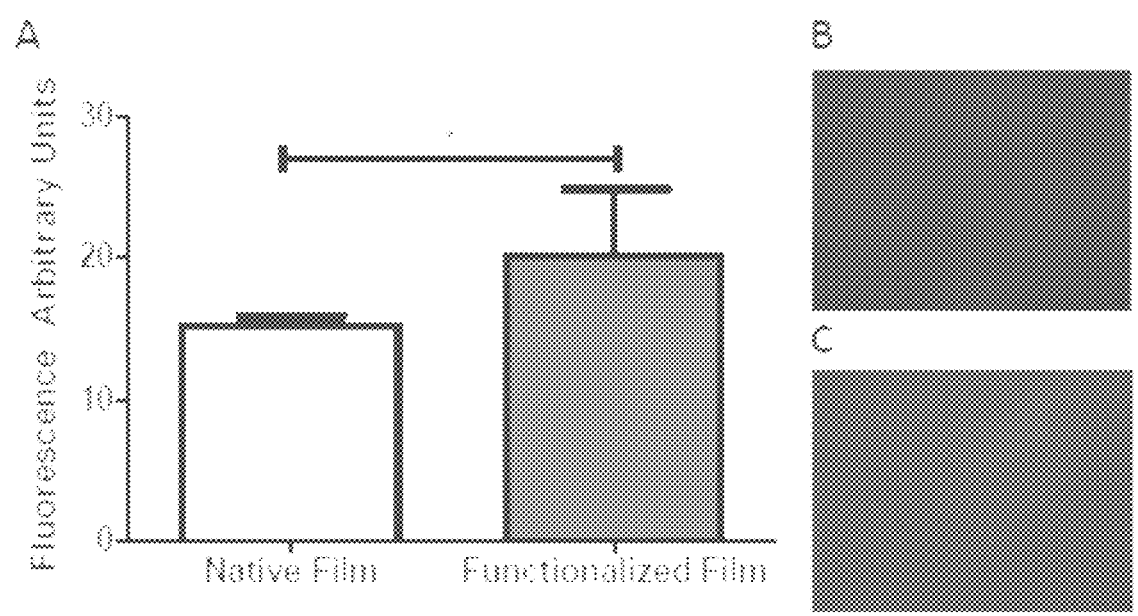
FIG. 8. (A) Fluorescence quantification of the immunochemistry assay against TGFBβ1 immobilized on implanted films. The data represents mean±SD of 5 measurements per sample (n=3). * p<0.05 (two tailed unpaired t-test). (B) Fluorescence image of the native film implanted subcutaneously on rat. (C) Fluorescence image of the film functionalized with TGF-β1 binding peptide implanted subcutaneously on rat.
Figure 9:
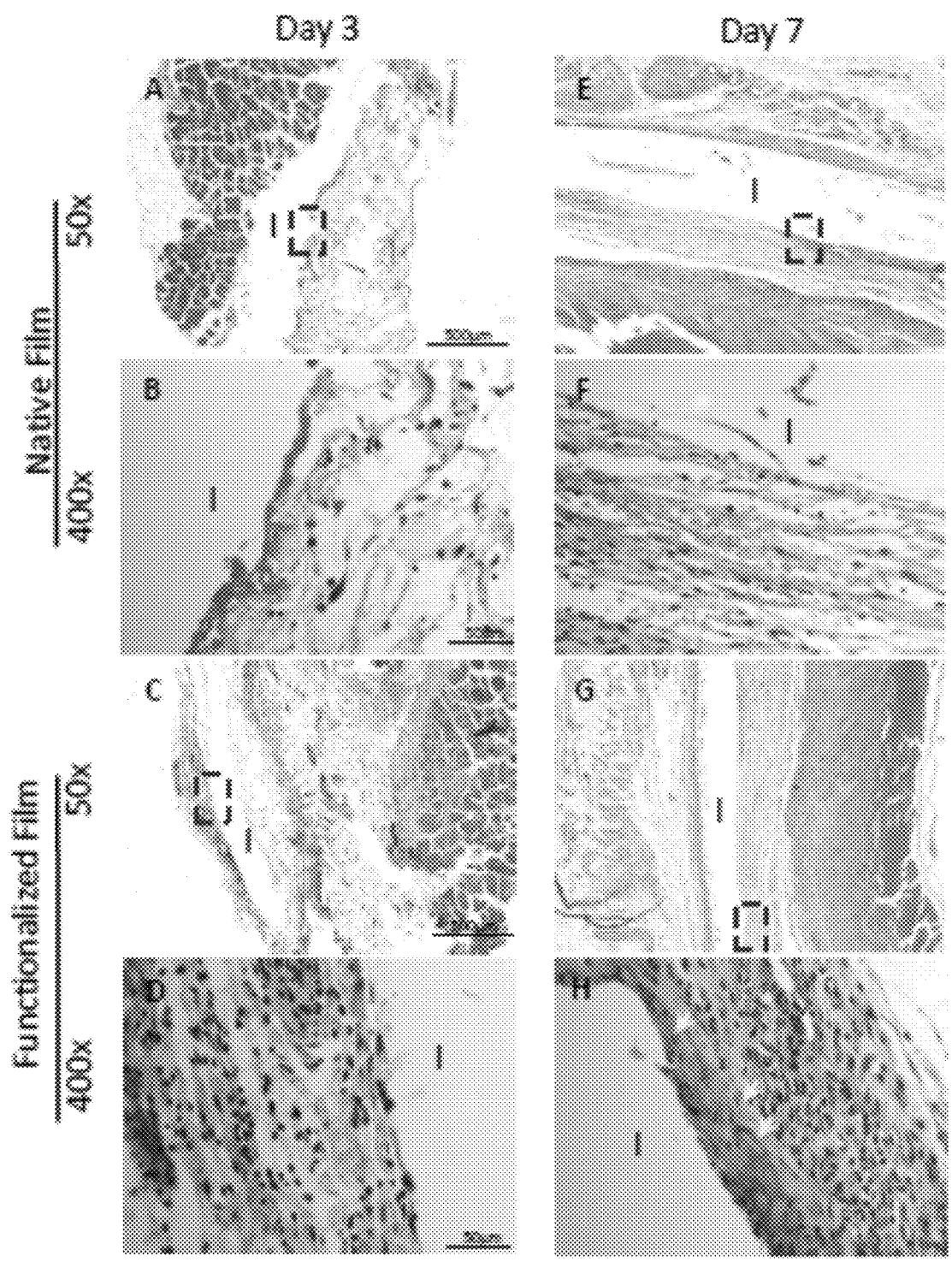
FIG. 9. Histological evaluation of samples sections after 3 (A-D) and 7 (E-H) days of implantation. Haematoxylin and eosin staining on native films (A, B, E and F) and functionalized films (C, G, D and H). Implant (I), blood vessels (v), fibroblast like cells (arrows), magnified area (dashed box).

TGF-β1 Binding Peptide Captures Native Circulating TGFB1 Leading to its Accumulation on the Implanted Functionalized Polymer We hypothesized that once implanted in vivo, the TGFB1 binding peptide could capture and accumulate the native circulating TGFB1 that is released during the inflammatory stage and induce a more pronounced tissue response around the implant. Both native and functionalized PCL films were subcutaneously implanted in the back of mice facing the fascia. Each animal, with a total of three animals per time point, was implanted with both native and functionalized film. At day 3 and day 7 after implantation, samples were harvested and used for immunofluorescence against TGFB1 and histology. Only the samples from day 7 were used for immunofluorescence against TGFB1. Immunostaining against TGFB1 showed a higher fluorescence signal in the films functionalized with the TGFB1 binding peptide when compared with the native films after 7 days of implantation in all the three animals (FIG. 8). This accumulation of the native TGFB1 in the films functionalized with the TGFB1 binding peptide led to a higher cellularity around the implant (mostly inflammatory cells) at day 3 when compared with the native films (FIG. 9, A-D). At day 7 there was also much more inflammatory and fibroblast-like cells (indicated with arrows) around the functionalized films when compared with the control (FIG. 9, E-H). Additionally, more blood vessels (indicated with v) were found around the functionalized PCL implant after 7 days (FIG. 9, H). Overall these results show that the TGF-β1 captured by the peptide led to a more pronounced inflammatory response ultimately leading to more recruitment of inflammatory cells, fibrogenic response and vascularization around the implant.

Conclusions

Here, a strategy is described to immobilize hTGFB1 in PCL through the interaction with a TGFB1 binding peptide. The immobilized hTGFB1 presented to the cells was shown to be bioactive and capable of activating the TGF-β pathway in primary human-derived hamstring cells. This is the first time that a method for the immobilization and delivery of hTGFB1 for tendon/ligament healing was described. In vitro studies showed that the immobilized hTGFB1 induced the expression of collagen type I and III in human-derived hamstring cells without having an effect in chondrogenic related genes (Sox9 and Aggrecan). In vivo studies showed that there was a higher accumulation of native TGFB1 on the films functionalized with a TGFB1 binding peptide which led to a more pronounced recruitment of inflammatory cells, fibrotic response and neovascularization around the implant. This highlights the potential of using this peptide sequence in the design of improved medical devices by adding the capacity of capturing the patient's native TGFB1 to the device and therefore locally enhance the effect that this GFs has in tissue repair.

Example 2: Immobilization of hBMP-2 on Polymers Directs Cell Fate

Materials and Methods

Materials

N,N,N',N'-Tetramethyl-O-(1H-benzotriazol-1-yl)uronium hexafluorophosphate (HBTU) was obtained from MultiSynTech. Chloroform and 1-methyl-2-pyrrolidinone (NMP) were purchased from WR Chemicals. NaOH was obtained from Riedel-de Haen. All other reagents or products were purchased from Sigma-Aldrich unless noted otherwise.

Peptide Synthesis and Purification

The peptide sequences were synthetized using Fmoc-solid phase peptide synthesis on a Syro II MultiSynTech automated peptide synthesizer. The BMP-2-binding and scrambled peptides with sequences KGYPVHPST (SEQ ID NO:9) and KGTPVHYPS (SEQ ID NO:47), respectively, were prepared on Fmoc-Rink 4-methylbenzhydrylamine (MBHA) resin (MultiSynTech GmBH, 50 mg scale, substitution 0.52 mmol/g), using 0.26 M of HBTU, 0.52 M of N,N-diisopropylethylamine (DIPEA), 2 M of piperidine and 0.29 M of each amino acid. The N-termini of the final peptide sequences were manually acetylated in 16% (v/v) acetic anhydride, 30% (v/v) DIPEA and 54% (v/v) NMP for one hour at room temperature. The peptides were cleaved from the resin and amino acid side groups were deprotected using 95% (v/v) trifluoroacetic acid, 2.5% (v/v) triisopropylsilane and 2.5% (v/v) MILLI-Q® water. The peptides were then collected by precipitation in cold diethyl ether and the organic solvents were removed in a rotatory evaporator. The peptides were redissolved in MILLI-Q® water and lyophilized overnight. The resulting products were purified using standard preparative HPLC methods. MS (ESI): m/z=1026.3 [M+H]+ (calculated 1026.1 for C47H71N13O13) for KGYPVHPST (SEQ ID NO:9). MS (ESI): m/z=1026.8 [M+H]+ (calculated 1026.1 for C47H71N13O13) for KGTPVHYPS (SEQ ID NO: 47).

Preparation of PCL Films Displaying BMP-2-Binding Peptides

A 12.5% (w/v) solution of PCL in chloroform was prepared and homogenized by sonication. The homogenized solution was cast in a petri dish, pre-silanized with a PFDTS (1H,1H,2H,2H-perfluorodecyltrichlorosilane, >97%, ABCR GmbH) anti-sticky layer, and the solvent allowed to evaporate overnight. The polymer was melted, allowed to again solidify and was then cut into circular films with a diameter of 21 mm in order to fit inside the wells of a 12-well plate. The individual circular films were extensively washed with demi-water and MILLI-Q® water and dried with a N2 stream. The dried films were exposed to oxygen plasma for 5 minutes (at an oxygen pressure of 1.0 bar, a vacuum pressure of 200 mbar and a current of 40 A) and subsequently immersed in a 1 M NaOH solution for one hour with gentle agitation. PCL films were then washed and dried as mentioned above, and incubated with a solution of 50 mM 1:1 NHS/EDC in MES buffer for one hour with agitation. PCL films were washed and dried again as mentioned above and incubated with 1 mM of the peptide in phosphate buffered saline (PBS) for 4 hours with agitation. Films were then extensively washed with PBS and sterilized by incubating the films overnight in a solution of 10% penicillin/streptomycin (Life Technologies) in PBS prior to cell seeding.

Water Contact Angle Measurements

The wettability of the PCL films was determined by a drop contact angle system (Kruss Contact Angle Measuring System G10). The contact angle was measured and calculated using Drop Analysis software. All reported contact angles are the average of n=6 measurements. MILLI-Q® water was used to measure the contact angle of the films.

BMP-2-Binding and Immunofluorescence

The PCL films were incubated with 1 µg/mL of hBMP-2 (PeproTech) in PBS for one hour with gentle agitation. The films were then washed three times for 10 minutes with 1 mM PBS TWEEN®20 (PBST) and then with PBS for a further 10 minutes. Next, the films were blocked for one hour with PBS containing 1% (w/v) bovine serum albumin (BSA) and subsequently washed as described above. Afterwards, the films were incubated with a 2 µg/mL solution of the primary antibody (rabbit polyclonal anti-human BMP-2, PeproTech) in the blocking solution for one hour with agitation. The films were washed as mentioned above and then incubated with an 8 µg/mL solution of the secondary antibody (goat anti-rabbit Alexa Fluor 594, Invitrogen) in PBS containing 1% w/v BSA for one hour with gentle agitation. Prior to fluorescence microscopy, the films were washed three times for 10 minutes with 1 mM PBST, rinsed three times with PBS and dried under a N2 stream.

For cell experiments, the sterile films were washed three times with PBS and incubated with concentrated hBMP-2 in PBS for one hour with gentle agitation. Subsequently, the films were extensively washed with TBST (0.5%) and PBS to remove any traces of the washing buffer prior to cell seeding.

Cell Culture

C2C12 Luc (a kind gift from Daniel Rifkin's lab) and C2C12 were expanded in Dulbecco's Modified Eagle Medium (DMEM, Life Technologies, Gaithersburg, MD) supplemented with 20% Fetal Bovine Serum (FBS, Life Technologies), 100 U/mL penicillin (Life Technologies), 100 µg/mL streptomycin (Life Technologies) and 2 mM L-glutamine (Life Technologies). Cells were grown at 37° C. in a humid atmosphere with 5% CO2. The medium was refreshed twice per week and cells were used for further subculturing or cryopreservation on reaching near confluence. C2C12 Luc express luciferase under the control of a ID1 promoter—a BMP-2 target gene (Zilberberg et al., 2007, BMC Cell Biol. 8(41). DOI: 10.1186/1471-2121-8-41).

Luciferase Assay

C2C12 Luc were seeded on films at 16,000 cells/cm2 in DMEM medium supplemented with 10% FBS and allowed to attach overnight at 37° C. in a 5% CO2 incubator. The cells were lysed the following day and the luciferase quantified according to the manufacturer's protocol (Promega, E4530). Luciferase values were normalized for DNA content quantified by CyQUANT cell proliferation assay (Invitrogen).

ALP Quantification and Staining

For the analysis of the amount of ALP produced, C2C12 cells were seeded on films at 20,000 cells/cm2 and allowed to attach overnight. Next day the amount of FBS was reduced to 2% and the cells cultured during 7 days with medium refreshes every 3 days. After 7 days the cells were lysed and the amount of ALP quantified using the CDP-star Universal Alkaline Phosphatase Detection Kit (Sigma-Aldrich) according to the manufacturer's instructions. The values for ALP were normalized to the amount of DNA, which was quantified with the CyQUANT cell proliferation assay (Invitrogen). Staining against ALP was performed with Fast Violet B Salt (Sigma-Aldrich) dye.

Subcutaneous Implantation Rat Model

All of the animal experiments were approved by the animal research ethics committee of the Chinese University of Hong Kong. Eight 12-week-old Sprague Dawley male rats were used in this study. The rats were anesthetized by intraperitoneal injection of 10% ketamine/2% xylazine (Kethalar, 0.3 ml: 0.2 ml); sedation was maintained by intramuscular injection of 10% ketamine (Sigma Chemical CO, St. Louis, MO). Subcutaneous implantation of PCL was performed. In brief, once the animals were anesthetized, shaved and washed, two incisions were made and native PCL and PCL functionalized with a BMP-2-binding peptide were inserted into the pockets and fixed to the fascia. The skin wound was then closed using sutures. At day 3 and day 7 post implantation, the animals were sacrificed and samples were harvested. Samples from the subcutaneous rat model were harvested at day 7 post implantation and rinsed with PBS. Harvested samples were fixed with 10% buffered formalin for 10 minutes and further permeabilized with PBST for 15 minutes. Samples were then washed with PBS and blocked with 1% (w/v) BSA for 1 hour in a shaker. Next, the samples were washed three times for 10 minutes with PBST and incubated with a dilution of 1:100 of the primary antibody (rabbit polyclonal anti BMP-2, Abcam) overnight at 4° C. After primary antibody incubation, samples were washed with PBST and incubated with a dilution of 1:100 of the secondary antibody (goat anti rabbit IgG-PE, Santa Cruz Biotechnology) for one hour at room temperature. Samples were washed with PBST prior to imaging.

Histology

At day 3 and day 7 post implantation, PCL implants and the surrounding tissues were harvested and rinsed with PBS. Harvested samples were fixed with 10% buffered formalin overnight and embedded in paraffin. Subsequently, 5 µm-thick paraffin sections along the transverse plane were collected. Haematoxylin and eosin (H&E) stained sections were examined under light microscopy (Leica Microsystems, Wetzlar, Germany).

Statistical Analysis

The data were analyzed using a Student's paired t-test, a one-way analysis of variance followed by a Tukey's multiple comparison test ($p<0.05$), or a two-way analysis of variance. The values represent the mean and standard deviation of three independent measurements.

Results

Functionalization of PCL with BMP-2-Binding Peptides

Figure 10:
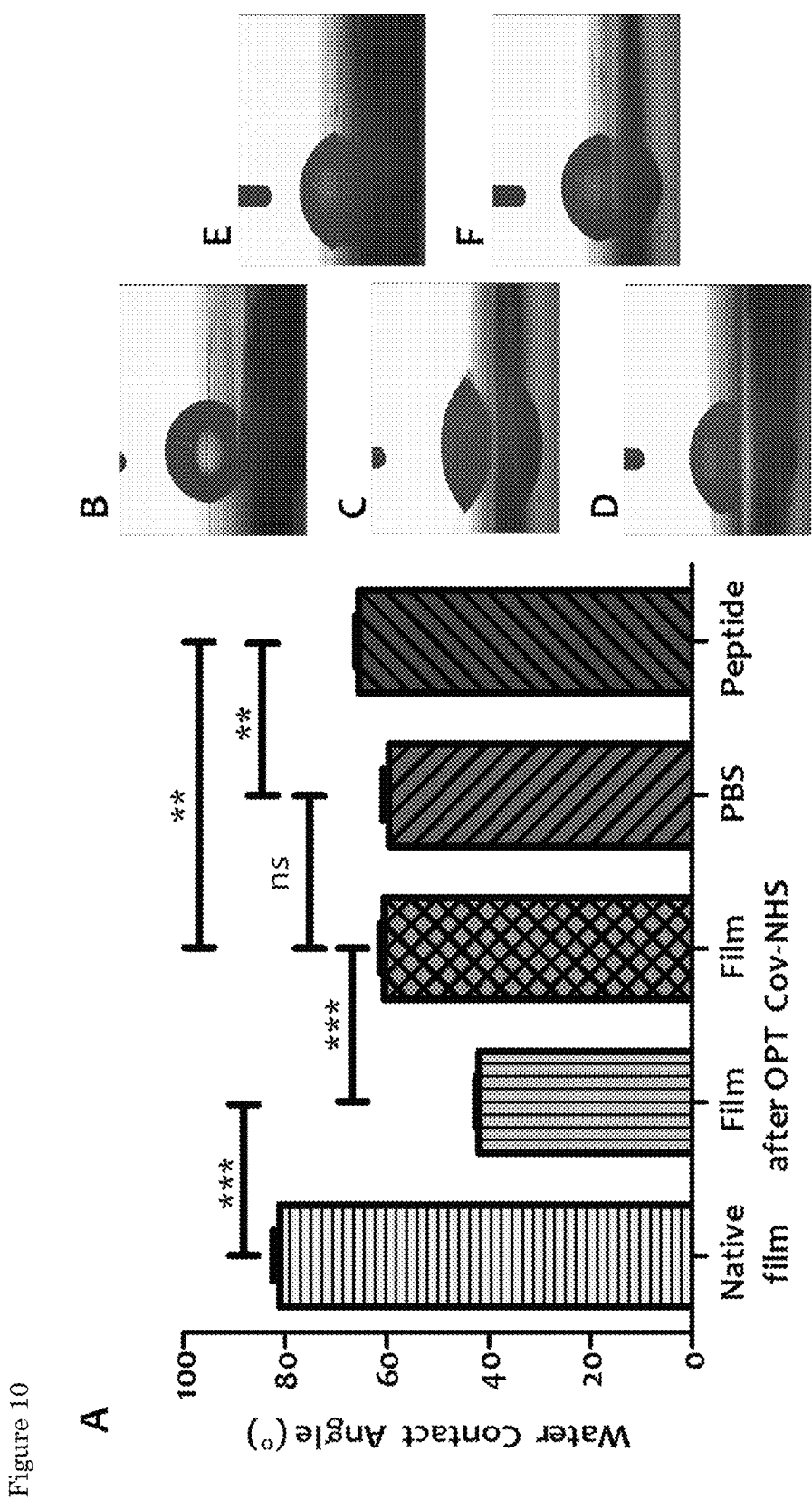
FIG. 10. A) Water contact angle measurements with respective representative pictures of the films during the chemical functionalization procedure; (B) "Native films" are the PCL films without any chemical modification; (C) "Film after OPT" refers to the native PCL films exposed for 5 minutes to oxygen plasma; (D) "Films Cov-NHS" are the films with amine reactive esters after 1 hour incubation with NHS/EDC; (E) "PBS" indicates the films with reactive amine esters incubated for 4 hours with PBS; (F) "Peptide" refers to the films with reactive amine esters incubated for 4 hours with a 1 mM peptide in PBS. *** p<0.0001 (two-tailed unpaired t-test). The data represent the mean±SD of two measurements per sample (n=6).

The BMP-2-binding sequence, YPVHPST, was synthesized with an extra glycine and lysine at the N-termini. The chemical modifications of the surface of the films were confirmed by following the changes in the water contact angle (FIG. 10). Treatment of the native PCL films with oxygen plasma led to a decrease in the water contact angle of 39±10 ($p<0.0001$) due to the introduction of oxygen-containing groups to the surface. An increase of 19±2° ($p<0.0001$) was observed after incubating the oxygen plasma activated films with NHS/EDC. Incubation of the amine reactive esters with 1 mM of the BMP-2-binding peptide in PBS resulted in an increase of the water contact angle of 5±1° ($p<0.01$). In contrast, incubation with only PBS did not lead to a significant change in the water contact angle of the films with the amine reactive esters.

BMP-2 Immobilization on the Functionalized PCL Films

An immunostaining against hBMP-2 was performed in order to confirm the binding of the GF to the functionalized films. These results showed that the fluorescence intensity was higher on functionalized films incubated with hBMP-2 compared to non-functionalized controls (Data not shown; $p<0.0001$). From these results, it was concluded that the reported signal is not due to nonspecific interaction of the primary or secondary antibody with the functionalized films. Incubation of the native film with hBMP-2 also led to a significant increase in the fluorescence signal when compared with the native film without hBMP-2 incubation. This can be explained by the fact that part of the hBMP-2 nonspecifically binds onto the native films. In summary, functionalization of the films with a BMP-2-binding peptide led to a higher surface concentration of hBMP-2 due to its affinity for the BMP-2-binding peptide, resulting in the highest fluorescence signal.

Immobilized hBMP-2 Retains its Bioactivity

Figure 11:
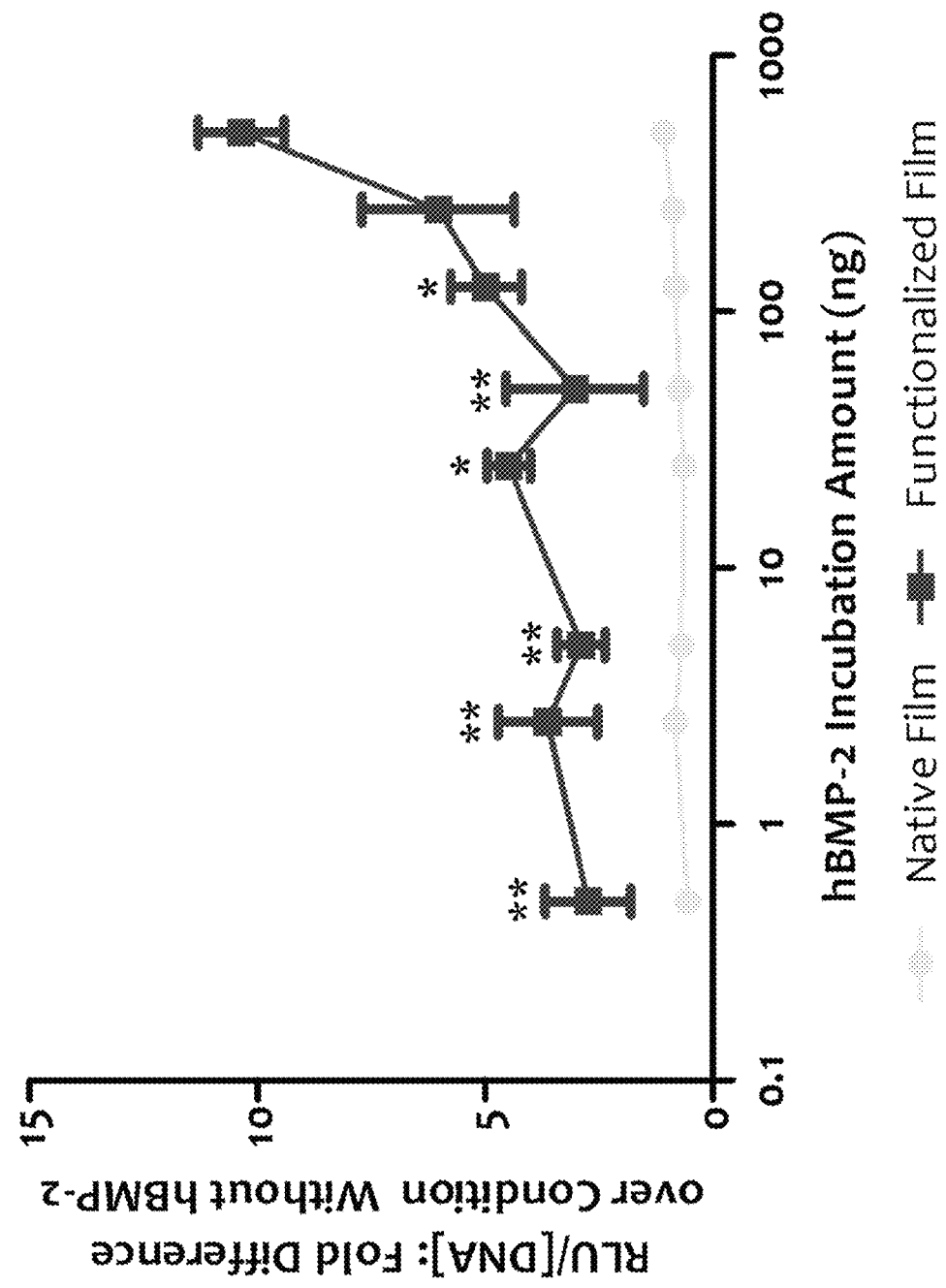
FIG. 11. Dose-response curve of immobilized hBMP-2 on the expression of luciferase by a BMP-2 reporter cell line. Luciferase values were corrected for the amount of DNA and normalized to the condition without incubation of BMP-2 prior to cell seeding. * p<0.05 and ** p<0.01 with a one-way ANOVA with Tukey's post-hoc test for analysis between a given hBMP-2 incubation amount and the incubation amount of 500 ng in the condition of the functionalized films. The data are represented as mean±SD of three samples.

A BMP-2 reporter cell line was used in order to confirm that the immobilized hBMP-2 retained its bioactivity. Both native and functionalized films were incubated with different amounts of hBMP-2 prior to cell seeding, and on the following day the luciferase was quantified and normalized to the amount of DNA (FIG. 11). The results showed that in the native films, regardless of the concentration of hBMP-2 used, no upregulation of luciferase was observed when compared to the native films without hBMP-2 incubation. In contrast, when the functionalized films were incubated with hBMP-2 before cell seeding, the hBMP-2 immobilized by the peptide retained its bioactivity, since it induced a significant increase in the amount of luciferase produced for all of the concentrations tested when compared with the condition where the functionalized films where not incubated with hBMP-2. The amounts of hBMP-2 were tested in the range of 0.5 to 250 ng, and this led to similar levels of luciferase as those produced in the functionalized films. The maximum value of luciferase produced in response to the immobilized hBMP-2 was observed when the functionalized films were incubated with 500 ng of hBMP-2. The reported value of 10.4±1.6 for this concentration was statistically significant when compared with all the other amounts tested, except for the case of 250 ng. The amount of 500 ng was used for further experiments.

Next, a further experiment was performed with the BMP-2 reporter cell line, where the cells were cultured on top of native films, films covalently modified until the NHS/EDC step, films with a scrambled peptide and films with a BMP-2-binding peptide. The films were incubated with a solution containing 500 ng of hBMP-2, the cells seeded in the absence or presence of 2 ng/mL of a specific BMP-2 inhibitor (Noggin) and the amount of luciferase quantified and normalized to the amount of DNA (Data not shown). The results showed that the incubation of films functionalized with a scrambled peptide with hBMP-2 prior to cell seeding did not lead to an increase in the amount of luciferase produced when compared with the same films without hBMP-2 incubation. In contrast, the presence of a BMP-2-binding peptide on the films allowed the immobilization of the hBMP-2, which induced a 5.3±2.0-fold increase in the amount of luciferase produced ($p<0.05$). Culture of the cells in the presence of a BMP-2 inhibitor completely suppressed the luciferase activity observed in response to the immobilized hBMP-2 ($p<0.01$).

Synthesis of ALP in Response to Immobilized hBMP-2

Figure 12:
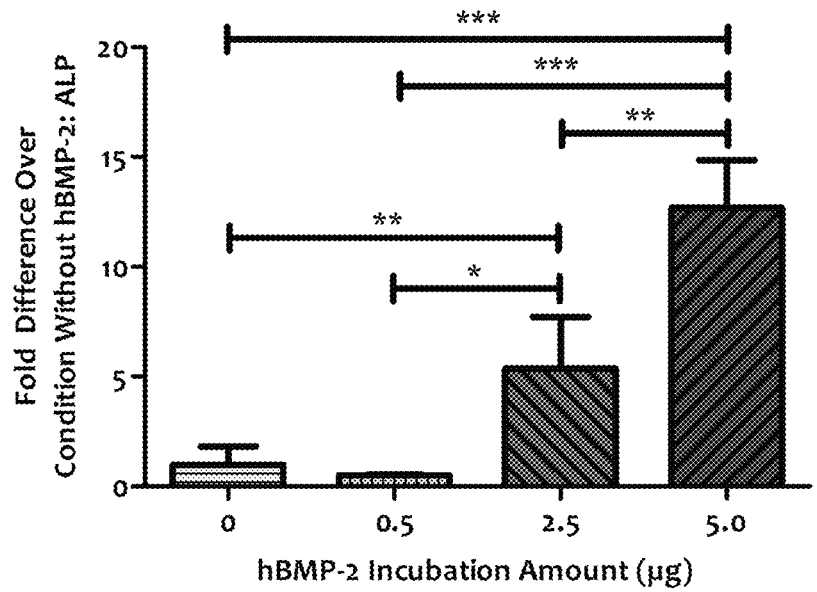
FIG. 12. Effect of immobilized hBMP-2 on the expression of luciferase by a BMP-2 reporter cell line. Luciferase values were corrected for the amount of DNA and normalized to the condition without incubation of hBMP-2 prior to cell seeding. * p<0.05,  p<0.01 and * p<0.0001 with a one-way ANOVA with Tukey's post-hoc test for analysis between all concentrations. The data are represented as mean±SD of two measurements per sample (n=3).

BMP-2 is known to direct the differentiation of C2C12 myoblasts into osteoblasts (Katagiri et al., 1994, J. Cell. Biol. 127:1755-66). In order to identify the amount of immobilized hBMP-2 needed to transdifferentiate the C2C12 into the osteogenic lineage, a dose response study of immobilized hBMP-2 was performed (FIG. 12). Films functionalized with a BMP-2-binding peptide were incubated with 0, 0.5, 2.5 and 5.0 µg of hBMP-2 and the amount of ALP synthesized was quantified after 7 days of culture. The results showed that incubation of the films with 500 ng, as used in previous experiments, was insufficient to induce the osteogenic differentiation of C2C12. Based on this, the concentration of hBMP-2 (2.5 and 5.0 µg) used for the pre-incubation was increased and, when doing so, a significant increase was shown in the amount of ALP produced when compared to the controls, reaching a maximum of a 12.7±2.2-fold increase for 5.0 µg. This amount of BMP was then used for further experiments.

Figure 13:
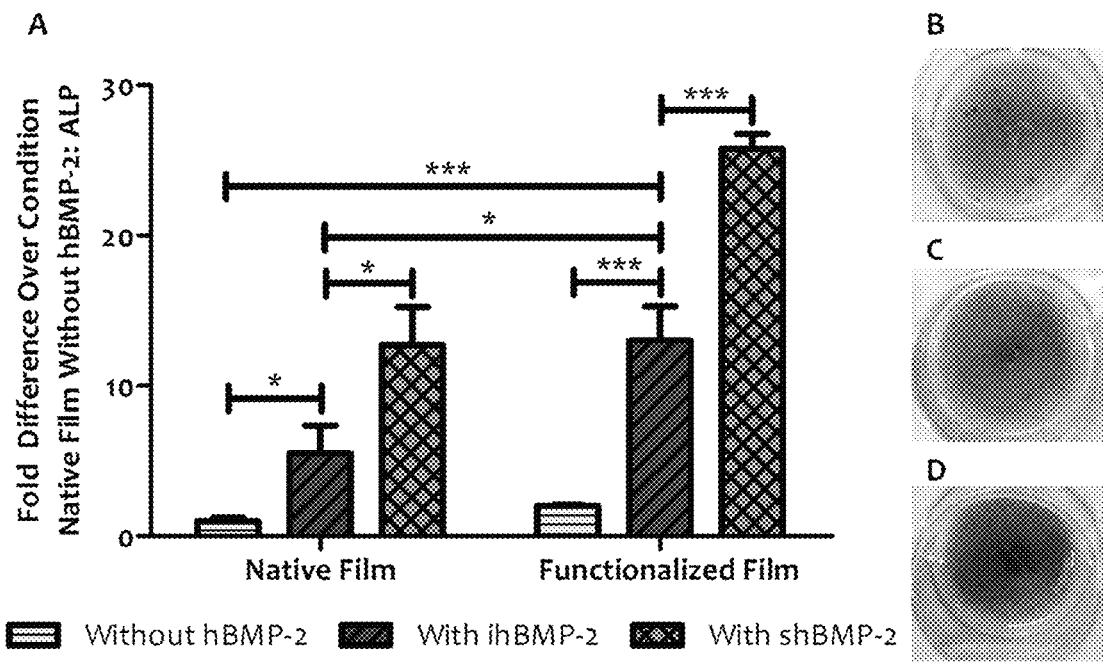
FIG. 13. (A) Quantification of ALP synthetized in response to immobilized hBMP-2 (ihBMP-2) and soluble hBMP-2 (shBMP-2) in native and functionalized films. * p<0.05,  p<0.01, * p<0.0001 (two-tailed unpaired t-test). The data represent the mean SD of two measurements per sample (n=3). (B) ALP staining in functionalized films without hBMP-2, (C) in functionalized films with ihBMP-2 and (D) functionalized films with shBMP-2.

Next, C2C12 were cultured on top of native films and films functionalized with a BMP-2-binding peptide that were incubated with 5.0 µg (ihBMP2) or without hBMP-2 before the cell seeding. In the case of the films without hBMP-2 incubation before cell seeding, the C2C12 were either cultured in the presence of 200 ng/mL (shBMP-2) or in the absence of soluble hBMP-2. Each time the medium was refreshed, new soluble hBMP-2 was added only for that condition, and ALP was quantified after 7 days (FIG. 13). These results showed that the incubation of both native and functionalized films with hBMP-2 prior to cell seeding led to an increase in the amount of ALP synthesized. However, the ALP production in response to the hBMP-2 immobilized by the BMP-2-binding peptides was 2.4 higher when compared with the response to the hBMP-2 nonspecifically adsorbed in the native films. Treatment with soluble hBMP-2 led to an even more pronounced response when compared with the condition in which the same films were incubated with hBMP-2 before cell seeding. Interestingly, there was no significant difference between the treatment with soluble hBMP-2 in the native films and the immobilized hBMP-2 in the functionalized films. Staining against ALP corroborated the results obtained from the ALP quantification.

Figure 14:
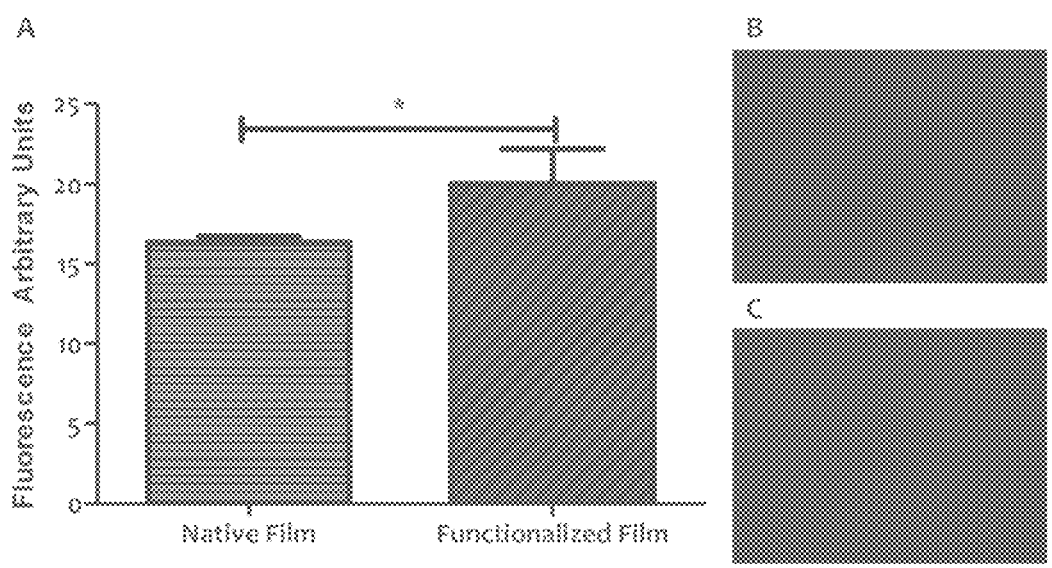
FIG. 14. (A) Fluorescence quantification of the immunochemistry assay against BMP-2 immobilized on implanted films. The data represent mean±SD of five measurements per sample (n=3). * p<0.05 (two-tailed unpaired t-test). (B) Fluorescence image of the native film implanted subcutaneously on rats. (C) Fluorescence image of the film functionalized with BMP-2-binding peptide implanted subcutaneously on rats.

Capture of Endogenous BMP-2 by the BMP-2-Binding Peptide Leads to Tissue Response During the inflammation stage of tissue healing, several cytokines are produced and released. These cytokines influence several cellular processes inherent in tissue healing. It was envisioned that the BMP-2-binding peptide could capture and accumulate the BMP-2 released during this stage, leading to a more pronounced tissue response. Both native and functionalized PCL films were subcutaneously implanted in the back of rats, facing the fascia. Each animal, with a total of three animals per time point, was implanted with both native and functionalized film. At day 3 and day 7 after implantation, samples were harvested and used for immunofluorescence against BMP-2 and for histology. Only the samples from day 7 were used for immunofluorescence against BMP-2. The fluorescence results reported a higher signal in the functionalized films in all three animals when compared with the native films after 7 days of implantation (FIG. 14). From the histological results, the accumulation of BMP-2 in the functionalized films resulted in a more pronounced recruitment of inflammatory cells and in the appearance of blood vessel-like structures at day 3 when compared with the native films (data not shown). After 7 days, further matrix deposition was observed around the functionalized films, with the tissue showing a higher degree of organization when compared with the native films. Overall, these results show that the BMP-2 captured by the peptide led to the recruitment of inflammatory cells and to the appearance of blood vessel-like structures after 3 days, and increased matrix deposition and tissue organization after 7 days.

In this work, a strategy to immobilize hBMP-2 via the interaction with a BMP-2-binding peptide was described. The peptide was covalently immobilized in PCL and its affinity toward the GF confirmed by immunochemistry. These in vitro studies showed that the immobilized hBMP-2 activated the BMP signaling cascade though the Smad-dependent pathway and supported osteogenic differentiation of C2C12. In fact, osteogenic differentiation in response to hBMP-2 immobilized by the peptide was significantly higher when compared with the response to the hBMP-2 that was only adsorbed to the native film. In vivo results showed a higher accumulation of BMP-2 in the implant functionalized with the BMP-2-binding peptide, which led to a higher recruitment of inflammatory cells, vascularization and matrix deposition. These findings highlight the potential of using this peptide sequence in the design of improved medical devices in order to deliver and/or capture hBMP-2 to/from the surrounding tissue. This development would allow a longer retention time of the GF in the biomaterial, which could potentially reduce the amount of GF required in order to successfully repair a damaged tissue.

Example 3

Materials and Methods

Materials
N,N,N',N'-Tetramethyl-O-(1H-benzotriazol-1-yl)uronium hexafluorophosphate (HBTU) was obtained from MultiSynTech. Chloroform and 1-methyl-2-pyrrolidinone (NMP) were purchased from WR Chemicals. NaOH was obtained from Riedel-de Haen. All other reagents or products were purchased from Sigma-Aldrich unless noted otherwise.

Peptide Synthesis and Purification

Peptides were synthetized using Fmoc-solid phase peptide synthesis in a Syro II MultiSynTech automated peptide synthesizer. The VEGF-binding peptide with the sequence KGSWWAPFH (SEQ ID NO:6) was prepared on Fmoc-Rink 4-methylbenzhydrylamine (MBHA) resin (MultiSynTech GmBH, 50 mg scale, substitution 0.52 mmol/g), using 0.26 M of HBTU, 0.52 M of N,N-diisopropylethylamine (DIPEA), 2 M of piperidine and 0.29 M of each amino acid. The N-terminus of the final peptide sequence was acetylated manually in 16% (v/v) acetic anhydride, 30% (v/v) DIPEA and 54% (v/v) NMP for one hour at room temperature. The peptide was cleaved from the resin and the amino acid side groups were deprotected using 95% (v/v) trifluoroacetic acid, 2.5% (v/v) triisopropylsilane and 2.5% (v/v) MILLI-Q® water. The peptide was then collected by precipitation in cold diethyl ether and the organic solvents were removed in a rotatory evaporator. The peptide was redissolved in MILLI-Q® water and lyophilized overnight. The resulting product was purified using standard preparative HPLC methods. MS (ESI): m/z=1156.4 [M+H]+ (calculated 1156.3 for C58H73N15O11) for KGSWWAPFH (SEQ ID NO:6).

Preparation of PCL Films Displaying VEGF-Binding Peptides

A 12.5% (w/v) solution of PCL in chloroform was prepared and homogenized by sonication. When the solution was completely homogeneous, PCL films were prepared by casting in a petri dish, pre-silanized with a PFDTS (1H,1H, 2H,2H-perfluorodecyltrichlorosilane, >97%, ABCR GmbH) anti-sticky layer. Upon solvent evaporation, the polymer was melted and allowed to again solidify. The polymer was then cut into circular films with a diameter of 21 mm in order to fit inside the wells of a 12-well plate. The individual circular films were extensively washed with demi-water and MILLI-Q® water and dried with a N2 stream. The dried films were exposed to oxygen plasma for 5 minutes (at an oxygen pressure of 1.0 bar, a vacuum pressure of 200 mbar and a current of 40 A) and subsequently immersed in a 1 M NaOH solution for one hour with gentle agitation. PCL films were then washed and dried as mentioned above, and incubated with a solution of 50 mM 1:1 NHS/EDC in MES buffer for one hour with agitation. PCL films were again washed and dried as mentioned above and were incubated with 1 mM of the peptide in phosphate buffered saline (PBS) for 4 hours with agitation. Films were then extensively washed with PBS and sterilized by incubating the films overnight in a solution of 10% penicillin/streptomycin (Life Technologies) in PBS prior to cell seeding.

Water Contact Angle Measurements

The wettability of the PCL films was determined by a drop contact angle system (Kruss Contact Angle Measuring System G10). The contact angle was measured and calculated using Drop Analysis software. All reported contact angles are the average of n=5 measurements. MILLI-Q® water was used to measure the contact angle of the films.

VEGF Binding and Immunofluorescence

Samples were incubated with 1 µg/mL of VEGF (PeproTech) in 0.5% (v/v) PBS TWEEN®20 (PBST) for one hour with gentle agitation. The films were then washed three times for 10 minutes with 0.5% (v/v) PBST and then with PBS for a further 10 minutes. Next, the films were blocked for one hour with PBS containing 1% (w/v) bovine serum albumin (BSA) and subsequently washed as described above. Afterwards, the films were incubated with a primary antibody (2 µg/mL; rabbit polyclonal anti-human VEGF, PeproTech) in the blocking solution during one hour with agitation. The films were washed as mentioned above and then incubated with a secondary antibody (8 µg/mL; goat anti-rabbit ALEXA FLUOR® 594, Invitrogen) in PBS containing 1% w/v BSA for one hour with gentle agitation. Before image acquisition, the films were washed three times for 10 minutes with 1 mM PBST, rinsed three times with PBS and dried under a N2 stream. Fluorescence intensity was quantified using ImageJ. For cell experiments, the sterile PCL films were washed three times with PBS and incubated with 0.5 µg of VEGF in 0.5% (v/v) PBST for one hour with gentle agitation. Subsequently, the films were extensively washed with PBST (0.5%) and PBS to remove any traces of the washing buffer prior to cell seeding.

Cell Culture

Human umbilical vein endothelial cells (HUVECs) were seeded at 5,000 cell/cm2 and expanded in Endothelial Growth Medium-2 supplemented with a BulletKit (EGMTM-2 BulletKit™, Lonza). Cells were grown at 37° C. in a humid atmosphere with 5% CO2. The medium was refreshed twice per week and cells were used for further sub-culturing or cryopreservation on reaching near confluence.

Cell Survival

HUVECs at passage 4 were used for experiments. The medium was removed and the cells washed with PBS. Next, the cells were incubated with 0.5% trypsin until they detached. Once detached, fresh medium was added to neutralize the trypsin and the cells were counted. Cell were seeded on films at 25,000 cells/cm2 in Endothelial Basal Medium (EBM-2) supplemented with 2% Fetal Bovine Serum (FBS) and gentamicin/amphotericin-B (GA-1000) and allowed to attach overnight at 37° C. in a 5% CO2 incubator. The medium was changed the following day to a medium without FBS and the cells were incubated for an additional period of 24 hours. After 24 hours, the cells were lysed and the DNA content was quantified by CyQUANT cell proliferation assay (Invitrogen), following the manufacturer's instructions.

Subcutaneous Implantation Mouse Model

All animal experiments were approved by the animal research ethics committee of the Chinese University of Hong Kong. Eight 12-week-old Sprague Dawley male rats were used in this study. The rats were anesthetized by the intraperitoneal injection of 10% ketamine/2% xylazine (Kethalar, 0.3 ml: 0.2 ml), and sedation was maintained by the intramuscular injection of 10% ketamine (Sigma Chemical CO, St. Louis, MO). Subcutaneous implantation of PCL was performed as follows: briefly, once the animals were anesthetized, shaved and washed, two incisions were made and native PCL and PCL functionalized with a VEGF-binding peptide were inserted into the pockets and fixed to the fascia; the skin wound was then closed using sutures. At day 3 and day 7 post implantation, the animals were sacrificed and the samples were harvested. Samples from the subcutaneous rat model were harvested at day 7 post implantation and rinsed with PBS. Harvested samples were fixed with 10% buffered formalin for 10 minutes and further permeabilized with PBST for 15 minutes. Samples were then washed with PBS and blocked with 1% (w/v) BSA for 1 hour in a shaker. Next, the samples were washed three times for 10 minutes with PBST and incubated with a dilution of 1:100 of the primary antibody (mouse polyclonal anti VEGF, sc-2269, Santa Cruz Biotechnology) overnight at 4° C. After primary antibody incubation, samples were washed with PBST and incubated with a dilution of 1:100 of the secondary antibody (goat anti mouse IgG-FITC, sc-2010, Santa Cruz Biotechnology) for one hour at room temperature. Samples were washed with PBST before imaging.

Histology

At day 3 and day 7 post implantation, PCL implants and the surrounding tissues were harvested and rinsed with PBS. Harvested samples were fixed with 10% buffered formalin overnight and embedded in paraffin. Subsequently, 5 µm-thick paraffin sections along the transverse plane were collected. Haematoxylin and eosin (H&E) stained sections were examined under light microscopy (Leica Microsystems, Wetzlar, Germany).

Experiments with Medical Devices

POLY-TAPE® was functionalized with a VEGF-binding peptide with the same protocol used to functionalize PCL films. Both Chondro-Gide and Collagen Meniscus Implant (CMI) were incubated with 50 mM of NHS/EDC for 2 hours. After 2 hours, the devices were washed several times with PBS and incubated with 1 mM solution of VEGF-binding peptide in PBS for a further 2 hours. Incubation with hVEGF, immunofluorescence staining and fluorescence quantification was performed as mentioned above for the PCL films.

In the case of the gradient experiments, a layer of solution containing 1 µg/mL of hVEGF was placed on top of a glass slide. The CMIs were placed on top of the solution, with the inner side in direct contact with the solution. Staining against immobilized hVEGF was performed as described above. For imaging, an automated fluorescence microscope (BD pathway) was used and several pictures were taken along the sample with an overlap of 10% between them. Pictures were mounted as a single picture using the plugin Stitching from ImageJ, and the fluorescence was quantified along the picture also using ImageJ.

Statistical Analysis

The data were analyzed using a Student's paired t-test, a one-way analysis of variance followed by a Tukey's multiple comparison test ($p<0.05$) or a two-way analysis of variance. The values represent the mean and standard deviation of three independent measurements.

Results

Functionalization of PCL with VEGF-Binding Peptides

An extra glycine and lysine were added at the N-termini of the VEGF-binding sequence SWWAPFH (SEQ ID NO:4). Water contact angle measurements were used in order to keep track of the chemical modifications that occurred at the surface of the PCL films (data not shown). Treatment of the native PCL films with oxygen plasma led to a decrease in the water contact angle of $32\pm2°$ ($p<0.0001$) due to the introduction of oxygen-containing groups on the surface. An increase of $18\pm2°$ ($p<0.0001$) was observed after incubating the oxygen plasma activated films with NHS/EDC. Incubation of the amine reactive esters with 1 mM of the VEGF-binding peptide in PBS resulted in an increase of the water contact angle of $7\pm2°$ ($p<0.01$). In contrast, incubation with only PBS did not lead to a significant change in the water contact angle of the films with the amine reactive esters.

Immobilization of VEGF onto PCL Films

Figure 15:
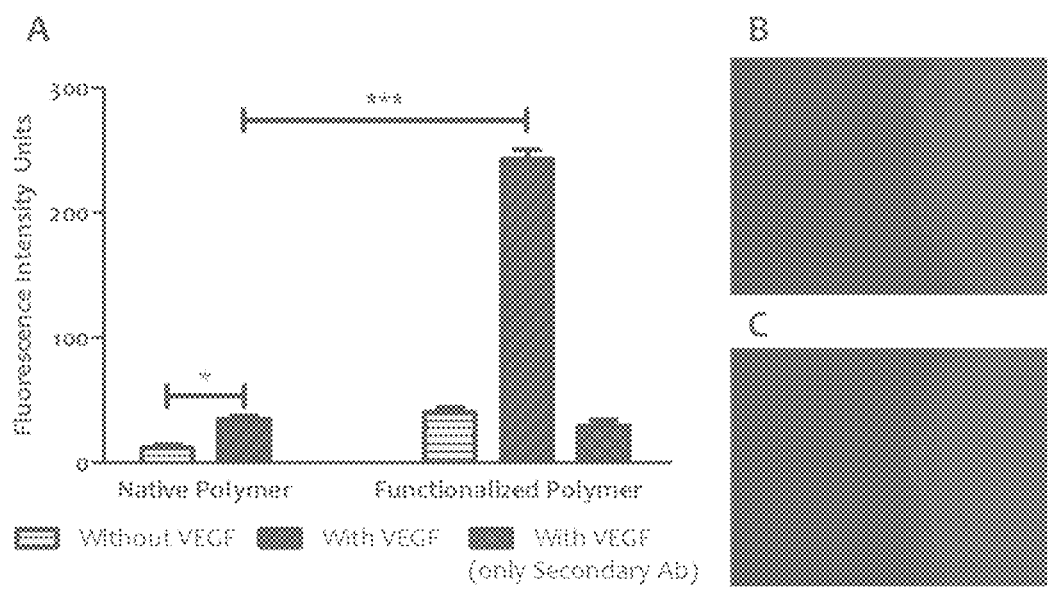
FIG. 15. (A) Fluorescence quantification of the immunochemistry assay against hVEGF immobilized on the films. The data represent mean±SD of three measurements per sample (n=2). *** p<0.0001 (one-way ANOVA) with functionalized films incubated with hVEGF and immunochemistry performed with primary and secondary antibody. (B) Fluorescence image of the functionalized film without (left) vs with (right) hVEGF incubation. (C) Fluorescence image of the native film (left) vs functionalized film (right) with hVEGF incubation. Scale bar: 1000 μm.

An immunostaining against hVEGF was performed in order to confirm the binding of hVEGF to the VEGF-binding peptide covalently immobilized at the PCL surface. A maximum fluorescence intensity was observed in the functionalized films incubated with hVEGF (FIG. 15, Panels A and B). This value was seven-fold higher than the non-functionalized films incubated with hVEGF (FIG. 15, Panels A and C). These results show that the reported fluorescence signal is solely due to the immobilization of VEGF at the surface and not due to the nonspecific interaction of the antibodies with the films. Incubation of the native film with hVEGF also led to an increase in the fluorescence signal when compared with the native films that were not incubated with hVEGF. This can be explained by nonspecific adsorption of hVEGF to the native film. In conclusion, it was shown that the functionalization of PCL films with a VEGF-binding peptide allows the immobilization of this GF on the film.

Immobilized hVEGF Enhances Survival of HUVECs

Figure 16:
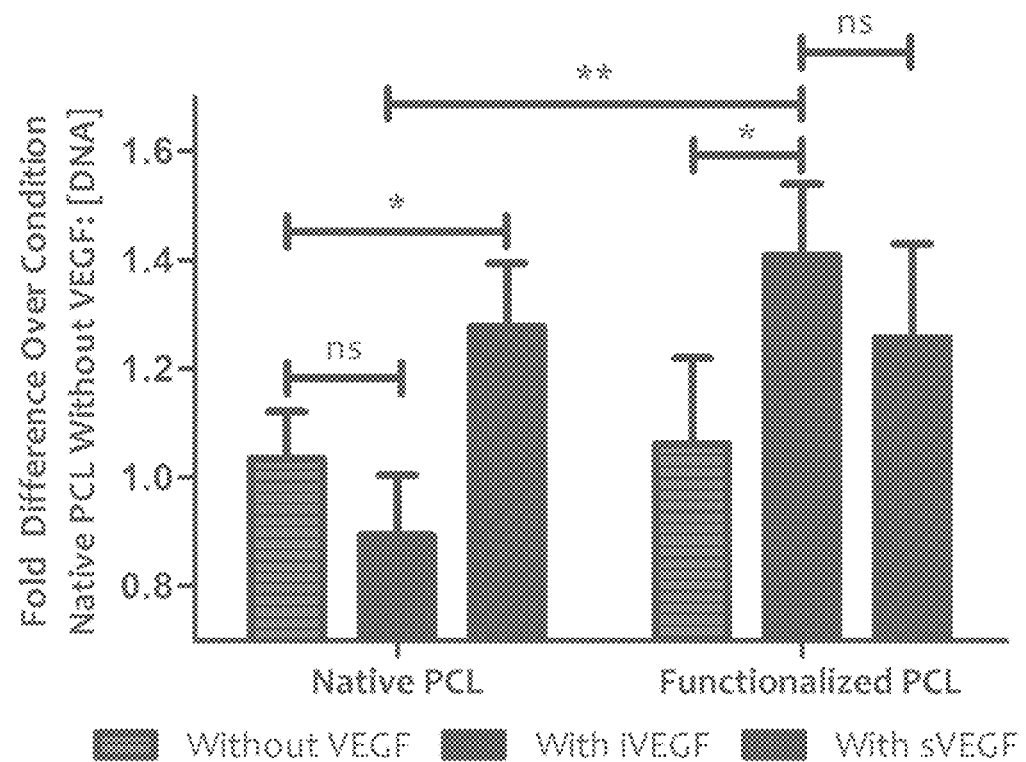
FIG. 16. The effect of the immobilized (ihVEGF) and soluble (shVEGF) VEGF in the survival of HUVECs cultured in native and functionalized films. * p<0.05, ** p<0.01 (two-tailed unpaired t-test). The data represent the mean±SD of two measurements per sample (n=3).

VEGF is known to induce the proliferation and survival of HUVECs (Tammela et al., 2005, Cardiovasc. Res. 65:550-63). Therefore, it was determined whether the immobilized hVEGF was capable of enhancing the survival of HUVECs after a starvation period of 24 hours (FIG. 16). HUVECs were seeded on top of native and functionalized films that were pre-incubated with 0 (without hVEGF) or 1 (with ihVEGF) μg/mL of hVEGF and allowed to attach overnight. The following day, the medium was replaced with EBM-2 without FBS and supplemented with 0 or 20 ng/mL of hVEGF (shVEGF) in the case of the films that were not pre-incubated with the GF prior to cell seeding. The medium of the remaining conditions was changed to basal medium only. After 24 hours, the total amount of DNA was quantified. As expected, treatment of the cells with soluble VEGF during the starvation period led to a significant increase in the amount of DNA when compared with the native films without hVEGF. Interestingly, the results showed that the amount of hVEGF that remained nonspecifically adsorbed to the native film did not lead to an increase in the number of cells after the starvation period. This may be explained by the fact that the surface concentration of the hVEGF is insufficient to trigger a cell response or by a loss of GF bioactivity due to conformational changes during the adsorption process. In contrast, preincubation of the functionalized films with hVEGF enhanced ECs survival, as measured by the total amount of DNA. This result shows that the VEGF captured by the VEGF-binding peptide remained bioactive and induced the survival of HUVECs during the starvation period. There was no statistical significance observed between the results from the functionalized films with immobilized VEGF and the native/functionalized films with soluble VEGF. In summary, the hVEGF captured by the VEGF-binding peptide retains its bioactivity by inducing a cell response in HUVECs.

In Vivo Capture of Endogenous VEGF by the VEGF-Binding Peptide Leads to the Appearance of Blood Vessel-Like Structures Several cytokines, such as interleukin-6 and -8 (IL-6 and -8) and tumor necrosis factor alpha (TNF-α), which are produced during the inflammatory stage, are known to upregulate VEGF expression (Maloney and Gao, 2015, Mediators Inflamm., 2015.21). It was hypothesized that the VEGF-binding peptide could capture and accumulate the VEGF that naturally occurs in the body or/and that is produced in response to inflammatory cytokines, leading to a more pronounced tissue response. Both native and functionalized PCL films were subcutaneously implanted in the backs of rats, facing the fascia. Each animal, with a total of three animals per time point, was implanted with both native and functionalized film. At day 3 and day 7 after implantation, samples were harvested and used for immunofluorescence against VEGF and histology. Only samples from day 7 were used for immunofluorescence against VEGF. A higher intensity signal was found in the functionalized films at day 7 post implantation in all three animals (data not shown), indicating that an increased amount of VEGF was found around the functionalized implant when compared with the native implant.

Histological Results

The accumulation of VEGF in the functionalized films resulted in a higher cellularity—the majority being inflammatory cells—and the appearance of blood vessel-like structures at day 3, when compared with the native films (data not shown). After 7 days, the tissue around the functionalized films showed it to be structurally more organized, with a high degree of vascularization. Overall, these results show that the accumulation of VEGF by the peptide led to the more pronounced recruitment of inflammatory cells and the appearance of blood vessel-like structures after 3 days, eventually leading to a more organized tissue around the functionalized implant after 7 days.

Figure 17:
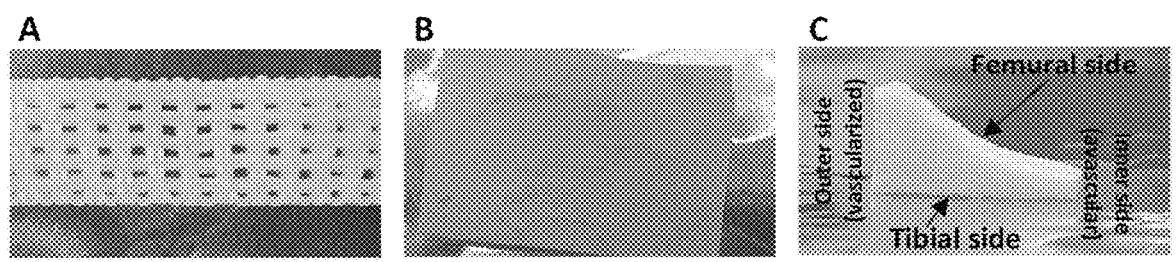
FIG. 17. Picture of the (A) POLY-TAPE® material, (B) Chondro-Gide and (C) CMI.
Figure 18:
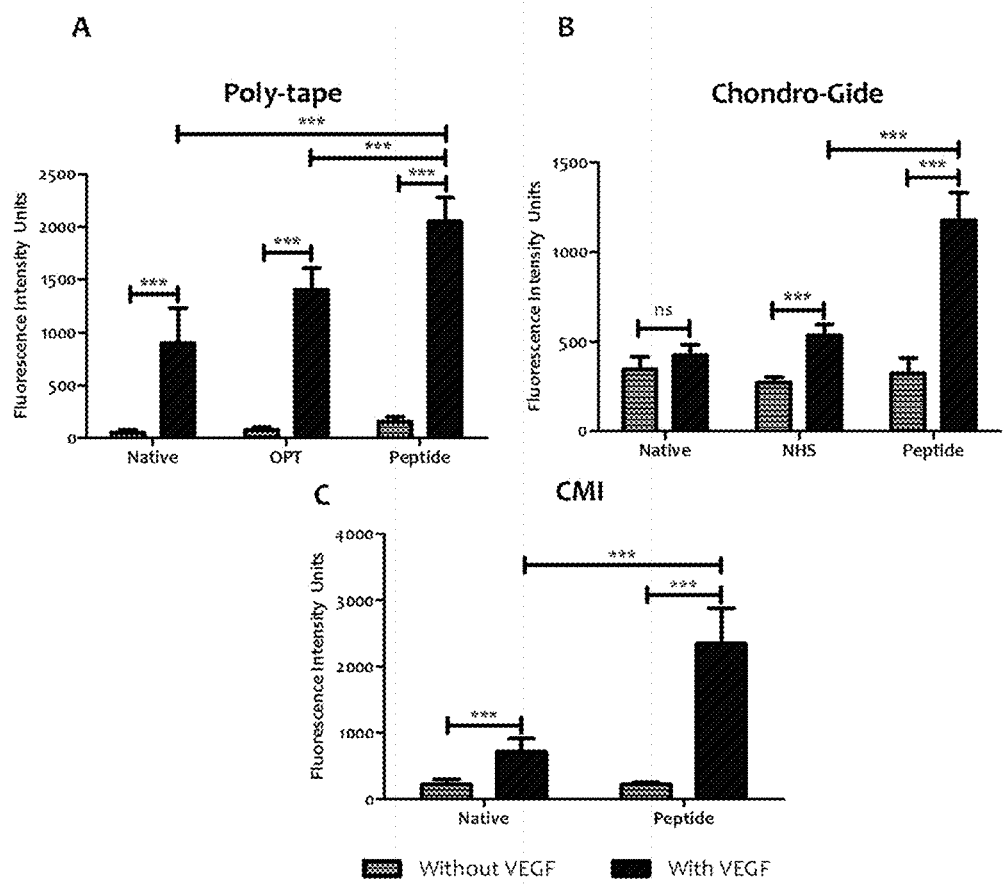
FIG. 18. Fluorescence quantification of the immunostaining against hVEGF on (A) POLY-TAPE®, (B) Chondro-Gide and (C) CMI that were incubated with 0 (without) and 1 μg/mL (with) of hVEGF. *** p<0.001 (two-tailed unpaired t-test). The data represent the mean SD per sample (n=5).

Functionalization of Orthopedic Medical Devices with VEGF-Binding Peptides Allows the Immobilization of VEGF Tissue healing requires cell infiltration from the blood stream to the tissue in order to induce the healing process. Vascularized tissues have increased healing abilities, due to higher exchange rates of nutrients and metabolic waste, and cell infiltration and migration. Tissues such as tendons, ligaments and meniscus are poorly vascularized and consequently have very low healing capacities. Therefore, several medical devices that are currently used in orthopedic surgeries were selected and modified in order to covalently immobilize the VEGF-binding peptide (FIG. 17). Next, the devices with hVEGF were incubated and the fluorescence signal was quantified from the immunostaining against the GF (FIG. 18). The medical devices used were POLY-TAPE® from iMove Medical™, which is a polyester mesh designed for soft tissue ingrowth and neoligament formation, it is composed of a poly(ethyleneterephthalate) fibers, Chondro-Gide from Geistlich Pharma AGTM, a collagen scaffold intended to be used for the treatment of articular cartilage defects, and Collagen Meniscus Implant (CMI) from IvySports Medicine™, which is intended to fill the void resulting from damage to and/or loss of meniscal tissue.

The POLY-TAPE® was oxygen plasma treated (OPT) for 5 minutes and incubated for one hour with 1 M NaOH in order to hydrolyze the esters and expose the carboxylic acids. Next, the POLY-TAPE® was incubated with NHS/EDC for one hour and finally with 1 mM of the VEGF-binding peptide in PBS for 2 hours. Incubation of the native POLY-TAPE® with hVEGF led to a significant increase in the fluorescence signal when compared with the same films without hVEGF incubation, showing that this polyester is prone to protein adsorption. Treatment of the POLY-TAPE® with oxygen plasma increased the surface hydrophilicity and consequently led to further unspecific adsorption of the hVEGF when compared with the native POLY-TAPE® that was also incubated with hVEGF ($p<0.01$). However, the fluorescence signal was maximal when the POLY-TAPE® functionalized with the VEGF-binding peptide was incubated with hVEGF, which was also 2.3 times higher than the native POLY-TAPE® with hVEGF ($p<0.001$) and 1.5 times higher than the POLY-TAPE® with OTP incubated with hVEGF ($p<0.001$). In the case of the Chondro-Gide, the scaffold was incubated with NHS/EDC for 2 hours in order to react with the carboxylic acids of the collagen proteins and subsequently incubated with the VEGF-binding peptide in PBS for a further 2 hours. Incubation of the native Chondro-Gide with hVEGF did not lead to an increase in the fluorescence signal, showing that this scaffold is unsuitable to function as a VEGF delivery system. However, modification of the carboxylic acids of the collagen proteins with NHS/EDC in order to introduce amine reactive esters allowed the immobilization of the hVEGF on the scaffold. This increase in the fluorescence signal may be due to the reaction of the free amines of the hVEGF with the amine reactive esters and/or due to unspecific adsorption of the hVEGF to the scaffold. Notwithstanding, it was when the material was functionalized with the VEGF-binding peptide that the highest fluorescence signal was observed, which was also 2.2 times higher than the value observed for the Chondro-Gide functionalized with NHS/EDC and incubated with hVEGF (p<0.001). The CMI, similarly to the Chondro-Gide, is a collagen-based material and therefore the chemical strategy of immobilizing the VEGF-binding peptide on it was the same used for the Chondro-Gide. In contrast to the Chondro-Gide, incubation of the native CMI with hVEGF led to an increase in the fluorescence signal due to the unspecific adsorption of the GF to the scaffold. However, the fluorescence signal was 3.3 times higher when the CMI functionalized with the VEGF-binding peptide was incubated with hVEGF. Taken together, these results show that medical devices that are currently used in the clinic can be redesigned and improved with the addition of a VEGF-binding peptide, in order to deliver and/or capture hVEGF and consequently to induce angiogenesis and the healing of tissues such as T/L, cartilage and meniscus that have very low healing capacities due to their inherently poor vascular networks.

Engineering hVEGF Immobilization in Functionalized CMIs in Order to Mimic the Meniscus's Vascular Network Distribution In the adult meniscus, vascular penetration is only 10-30% of the width of the medial meniscus and 10-25% of the width of the lateral meniscus. Two distinct zones can be identified in terms of vascularization: an outer, vascularized zone and an inner, avascular zone (Makris et al., 2011, Biomaterials 32:7411-31). Therefore, spatial presentation of hVEGF in functionalized CMIs is required to mimic the vascular network of the meniscus. The outer side of the functionalized CMIs was placed on top of a layer of solution containing 1 µg/mL of hVEGF and contact was allowed to occur for 10 and 60 minutes. The scaffold acted as a sponge, and due to capillary forces the hVEGF solution moved upwards in the direction of the inner side. A gradient of the GF can therefore be achieved depending on the time that the CMI is allowed to contact the hVEGF solution. Next, the scaffolds were stained against hVEGF and the outer, femoral and tibial side of the scaffolds were imaged (data not shown). In the cases of the tibial and femoral sides, the images were taken from the inner to the outer side of the scaffold. The lateral outer side of the CMI, which was in direct contact with the layer of hVEGF solution, had a homogeneous distribution of the GF from the tibial to the femoral side. When the CMI was in contact with the hVEGF solution for 10 minutes, there was a higher concentration of hVEGF in the core of that side, while the amount was lower in the border areas. However, when the CMI was allowed to be in contact with the hVEGF for a longer period, there was no difference in fluorescence between the core and the border areas. In both cases, the slope deviation from zero was not statistically significant. Regarding the femoral and the tibial sides of the CMI, an hVEGF gradient was achieved from the inner to the outer side when the CMI was in contact with the hVEGF solution for 10 minutes. The inner side of the CMI, which corresponded to the avascular side of the meniscus, and the side that was furthest away from the hVEGF solution, showed a lower fluorescence intensity. The fluorescence increased in the direction toward the outer side, which corresponded to the vascularized side of the meniscus, and which was in direct contact with the hVEGF solution. Both the femoral (p<0.0001) and the tibial (p=0.0003) side of the CMI that were in contact for 10 minutes with the hVEGF solution showed results that were statistically significantly different from zero. When the CMI was allowed to be in contact with the hVEGF solution for a longer period, the concentration gradient vanished. In the case of the femoral side, the hVEGF became homogenously distributed from the inner to the outer side, with a slope not statistically significantly different from zero. In contrast, the tibial side had a higher amount of hVEGF at the inner side. In summary, these results show that the distribution of hVEGF in CMI devices that were functionalized with a VEGF-binding peptide was able to be controlled in order to achieve gradients of hVEGF and consequently to supply different areas of the meniscus with varying amounts of GF according to the natural vascular network distribution within this tissue.

In this work, the immobilization and delivery of VEGF was investigated in various biomaterials via interaction with a VEGF-binding peptide. In vitro studies showed that the bioactivity of the immobilized VEGF was not lost and that it induced the survivability of cells. In vivo studies showed that implants functionalized with the VEGF-binding peptide captured the endogenous GF, leading to its accumulation around the implant. This accumulation of VEGF resulted in the higher recruitment of inflammatory cells and in neovascularization at day 3, which ultimately led to a higher organization of the tissue around the functionalized implant at day 7. It was also shown that medical devices that are currently used in standard orthopedic surgeries can be modified with the VEGF-binding peptide, turning them into a VEGF capturing device. Once implanted in the patient, the functionalized medical devices would capture endogenous VEGF and consequently trigger vascularization and enhance the healing of avascular tissues.

Example 4

Materials and Methods

Materials

N,N,N',N'-Tetramethyl-O-(1H-benzotriazol-1-yl)uronium hexafluorophosphate (HBTU) was obtained from MultiSynTech. Chloroform and 1-methyl-2-pyrrolidinone (NMP) were purchased from VWR Chemicals. NaOH was obtained from Riedel-de Haen. All other reagents or products were purchased from Sigma-Aldrich unless noted otherwise.

Peptide Synthesis and Purification

The TGF-β1-binding peptide was synthetized by standard Fmoc-solid phase peptide synthesis in a Syro II MultiSynTech automated peptide synthesizer. The TGF-β1-binding peptide KGLPLGNSH (SEQ NO:3) was prepared on Fmoc-Rink 4-methylbenzhydrylamine (MBHA) resin (MultiSynTech GmBH, 50 mg scale, substitution 0.52 mmol/g), using 0.26 M of HBTU 0.52 M of N,N-Diisopropylethylamine (DIPEA), 2 M of piperidine and 0.29 M of each amino acid. The N-terminus of the final peptide sequence was manually acetylated in 16% acetic anhydride, 30% DIPEA and 54% NMP for one hour at room temperature. The peptide was cleaved from the resin and the amino acid side groups were deprotected using 95% trifluoroacetic acid, 2.5% triisopropylsilane and 2.5% MILLI-Q® water. The peptide was then collected by precipitation in cold diethyl ether and the organic solvents were removed in a rotatory evaporator. The peptide was redissolved in MILLI-Q® water and lyophilized overnight. The resulting product was purified using standard preparative HPLC methods. MS (ESI): m/z=964.1 [M+H]+ (calculated 963.1 for C42H70N14O12) for KGLPLGNSH (SEQ ID NO:3). A higher concentration of peptide and/or a longer incubation did not result more peptide being added to the tape (based on the percentage of nitrogen atoms detected in XPS measurements).

Preparation of PCL Films Displaying TGF-β1-Binding Peptides

A 12.5% (w/v) solution of PCL in chloroform was prepared and homogenized by sonication. When the solution was completely homogenized, PCL films were prepared by casting in a petri dish pre-silanized with a PFDTS (1H,1H, 2H,2H-Perfluorodecyltrichlorosilane, >97%, ABCR GmbH) anti-sticky layer. Upon solvent evaporation, the polymer was melted and allowed to again solidify. The polymer was then cut into circular films with a diameter of 21 mm in order to fit inside the wells of a 12-well plate. The individual circular films were extensively washed with demi-water and MILLI-Q® water and dried with a N2 stream. The dried films were exposed to oxygen plasma for 5 minutes (at an oxygen pressure of 1.0 bar, a vacuum pressure of 200 mbar and a current of 40 A) and subsequently immersed in a 1 M NaOH solution for one hour with gentle agitation. PCL films were then washed and dried as mentioned above and incubated with a solution of 50 mM 1:1 NHS/EDC in MES buffer for one hour with agitation. PCL films were again washed and dried as mentioned above and incubated with 1 mM of the peptide in phosphate buffered saline (PBS) for 4 hours with agitation. Films were then extensively washed with PBS and sterilized by incubating the films overnight in a solution of 10% penicillin/streptomycin (Life Technologies) in PBS prior to cell seeding.

Generation of TGF-β1-Binding Peptide Gradients on PCL Films

Pellets of PCL were placed inside a mold of 6 cm in length and 1 cm in width and heated to 100° C. for 5 minutes using a hot press. After cooling, the solid PCL sample was cut into two halves. Individual PCL films of 3 cm in length and 1 cm in width were extensively washed with demi-water and MILLI-Q® water and dried with a N2 stream. The dried films were exposed to oxygen plasma for 5 minutes (at an oxygen pressure of 1.0 bar, a vacuum pressure of 200 mbar and a current of 40 A) and subsequently immersed in a 1 M NaOH solution for one hour with gentle agitation. PCL films were then washed and dried as mentioned above, and incubated with a solution of 50 mM 1:1 NHS/EDC in MES buffer for one hour with agitation. PCL films were then washed and dried as described above. Gradients of TGF-β1-binding peptides were generated by dipping the PCL films in a solution of the TGF-β1-binding peptide in PBS at a controlled speed using a motorized dip coater. Films were then extensively washed with PBS and stored for further experiments.

XPS Measurements

XPS spectra were measured using a Quantera scanning X-ray multiprobe instrument (Physical Electronics), equipped with a monochromatic Al Kα X-ray source operated at 1486.6 eV and 55 W. Spectra were referenced to the main aliphatic C is peak set at 284.8 eV. The X-ray beam size was 200 μm and the data were collected from surface areas of 100 μm×300 m with a pass energy of 224 eV and a step energy of 0.8 eV for survey scans, at a detector input angle of 45°. Measurements were collected after three scanning cycles. Charge neutralization was achieved by low-energy electrons and low-energy argon ions.

TGF-β1 Binding and Immunofluorescence

The PCL films were incubated with 1 μg/mL of hTGF-β1 (PeproTech) in 0.5% (v/v) phosphate buffered saline TWEEN®20 (PBST) for one hour with gentle agitation. The films were then washed six times for 10 minutes with 0.5% (v/v) PBST and then with PBS alone for a further 10 minutes. Next, the films were blocked for one hour with PBS containing 1% (w/v) BSA. Afterwards, the films were incubated with a 5 μg/mL solution of the primary antibody (mouse monoclonal anti-human TGF-β1, R&D systems) in the blocking solution for one hour with agitation. The films were washed three times as mentioned above and then incubated with a 4 μg/mL solution of the secondary antibody (goat anti-mouse Alexa Fluor 546, Invitrogen) in PBS containing 1% (w/v) BSA for one hour with gentle agitation. Prior to fluorescence microscopy, the films were washed three times for 10 minutes with 0.5% (v/v) PBST and rinsed three times with PBS.

Fluorescence Imaging and Quantification

The TGF-β1 gradient was visualized using an automated fluorescence microscope (BD Pathway). Several pictures were taken along the sample, with each picture having a 10% overlap with the next. After imaging, all pictures were mounted in a single picture that covered the complete length of the sample using the Stitching plugin from ImageJ. ImageJ was also used for quantification of fluorescence across the gradient. The values of fluorescence per pixel were then converted to fluorescence per centimeter.

Statistical Analysis

The data were analyzed using a Student's paired t-test, a one-way analysis of variance followed by a Tukey's multiple comparison test ($p<0.05$) or a two-way analysis of variance. The values represent the mean and standard deviation of three independent measurements.

Results

Figure 19:
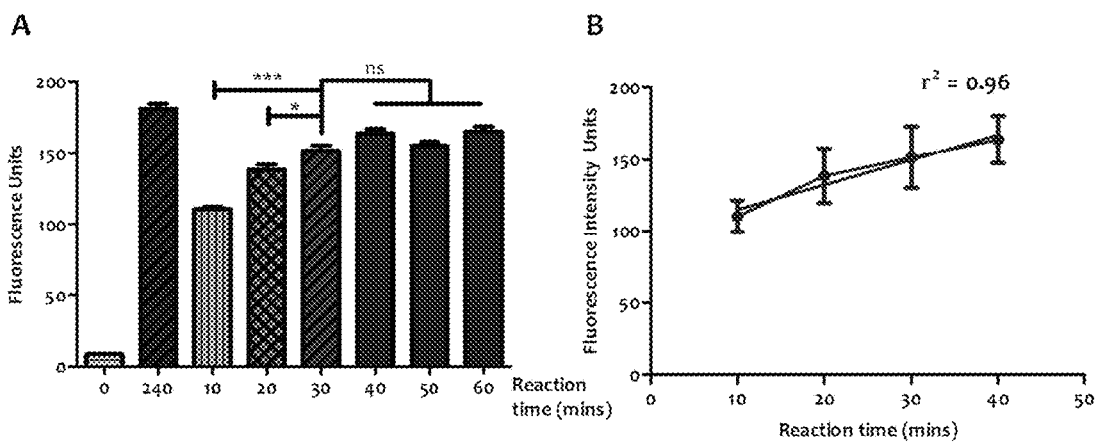
FIG. 19. (A) Fluorescence quantification of the antibody staining assay against hTGF-β1, which was immobilized on the TGF-β1-binding peptide functionalized PCL films, for different reaction times. (B) Fluorescence intensity plotted vs reaction time. The data represent mean±SD of six measurements per sample (n=5). * p<0.05 *** p<0.0001 (one-way ANOVA).

Amount of Immobilized hTGF-β1 is Dependent on the Reaction Time Between the PCL Films and the TGF-β1-Binding Peptide Testing was performed as to whether the reaction time between the NHS groups at the surface of the PCL films and the TGF-β1-binding peptide would lead to differing surface concentrations of the peptide and consequently to varying amounts of immobilized hTGF-β1. PCL films were chemically modified until the NHS/EDC step, as mentioned in chapter 3, and were then incubated without (negative control) or with the TGF-β1-binding peptide for 10, 20, 30, 40, 50, 60 and 240 (positive control) minutes. Next, the films were incubated with hTGF-β1, the antibody stained against the GF, imaged and the fluorescence was quantified (FIG. 19). Increasing the reaction time between the PCL films and the NHS groups at the surface and the TGF-β1-binding peptide led to an increase in the amount of immobilized hTGF-β1. The data show that the amount of immobilized hTGF-β1 increased linearly with the reaction time until 40 minutes. After 40 minutes, further increasing the reaction time did not lead to a significant increase in the fluorescence intensity. There was also no statistically significant difference observed between the results from the 30 minutes and higher reaction times; therefore, 30 minutes was selected as the optimal reaction time in order to achieve a gradient of the TGF-β1-binding peptide on the PCL film.

Characterization of TGF-β1-Binding Peptide Gradients on PCL Films

Figure 20:
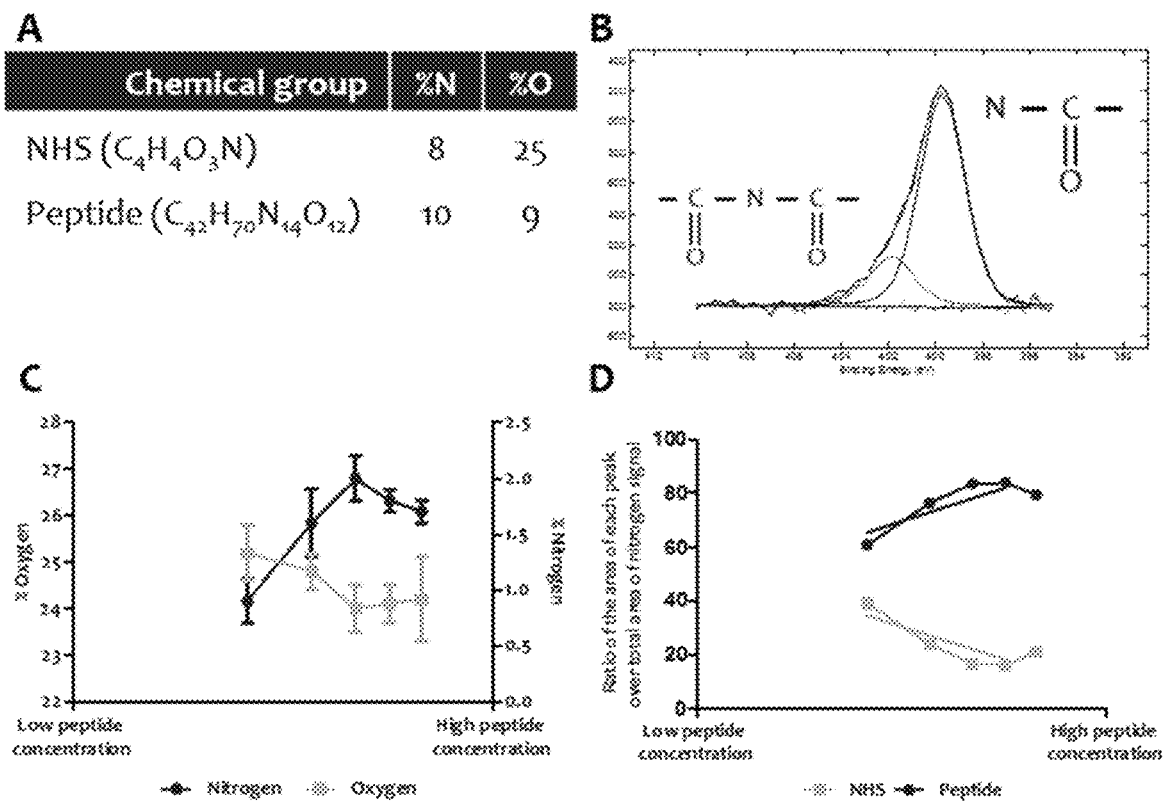
FIG. 20. (A) The nitrogen and oxygen composition of the NHS group and the TGF-β1-binding peptide. (B) Characteristic XPS spectra of nitrogen, where two peaks are visible: at 399 eV, corresponding to the TGF-β1-binding peptide, and at 402 eV, corresponding to the NHS group. (C) Atomic composition of oxygen and nitrogen along the film. (D) The ratio of the peak areas at 399 and 402 eV divided by the total area of the nitrogen XPS spectra for the five areas of the gradient measured. The linear regression excludes the final point.

An automated dip coater machine was used to generate gradients of the TGF-β1-binding peptide on PCL films. The films were held vertically using a grip, immersed into the TGF-β1-binding peptide solution and pulled out at controlled speeds. The longer a certain region of the film was allowed to react with the TGF-β1-binding peptide solution, the higher the surface concentration of the peptide. A speed of 0.1 cm/minutes was used to generate the gradients, and the gradients were subsequently validated using XPS. Five different regions of the film were scanned and five areas per region were measured. When the NHS groups at the surface of the film were replaced by the TGF-β1-binding peptide, an increase in nitrogen content and a decrease in oxygen content was observed by XPS analysis (FIG. 20, Panel A). When moving from the regions of the film that were in contact with the peptide solution for short periods to regions that were allowed to react for longer, an increase in the nitrogen and a decrease in the oxygen content was observed, as expected (FIG. 20, Panel C). It appears, however, that a plateau was reached for the final three regions measured. From the nitrogen spectra, two different peaks were observed: a peak at 399 eV that corresponded to the bonds present in the peptide chain and a peak at 402 eV corresponding to the NHS groups (FIG. 20, Panel B). The area of a given peak divided by the sum of the area of all peaks of the corresponding spectra gave the ratio of the type of bond present. The data show that the area of the peak from the peptide increased when moving from regions of the PCL film with short reaction times to regions with longer reaction times, while the area from the NHS group simultaneously decreased. In summary, these results show that by using an automated dip coater and by controlling the time that a given area of the PCL film is allowed to react with the peptide solution, it is possible to generate gradients of the TGF-β1-binding peptide on PCL films.

TGF-β1-Binding Peptide Gradients Lead to Gradients of hTGF-β1

Figure 21:
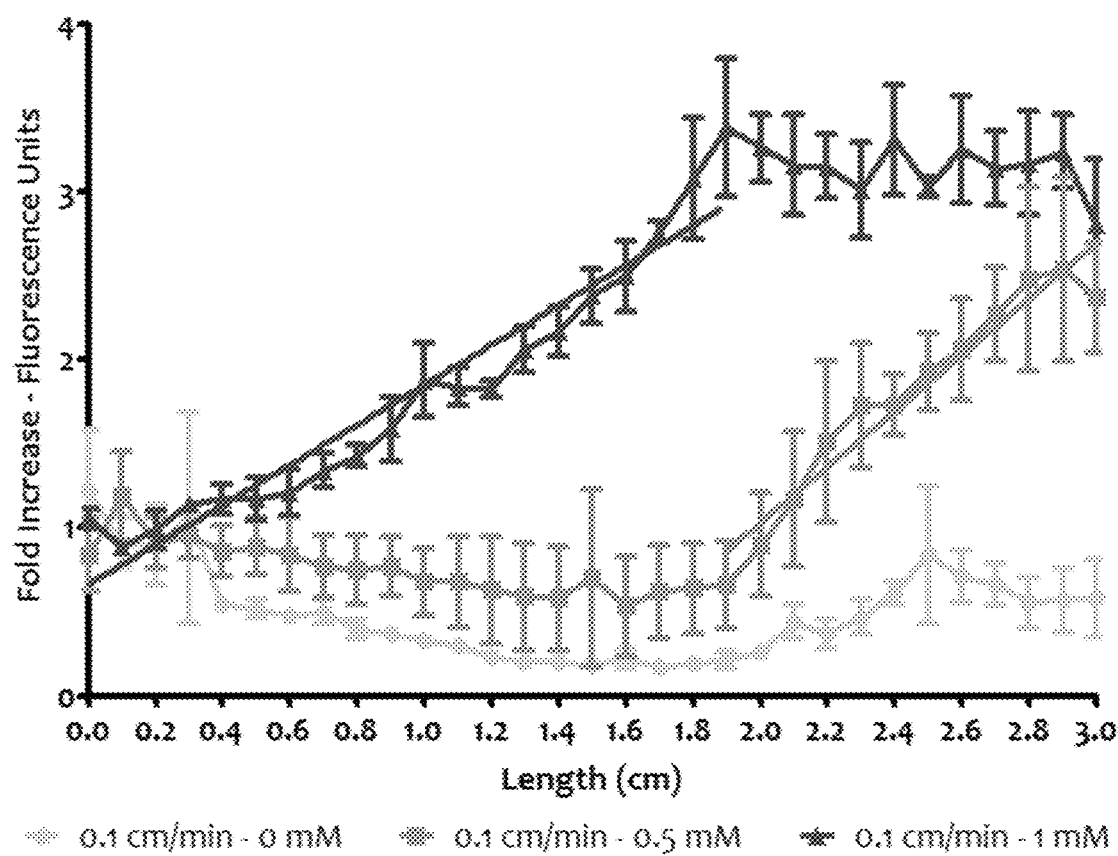
FIG. 21. Profiles of the immobilized TGF-β1 on TGF-β1-binding peptide gradient generated using different concentrations of the peptide at the speed of 0.1 cm/minute, as a function of the length of the PCL films. Fluorescence was calculated using ImageJ.
Figure 22:
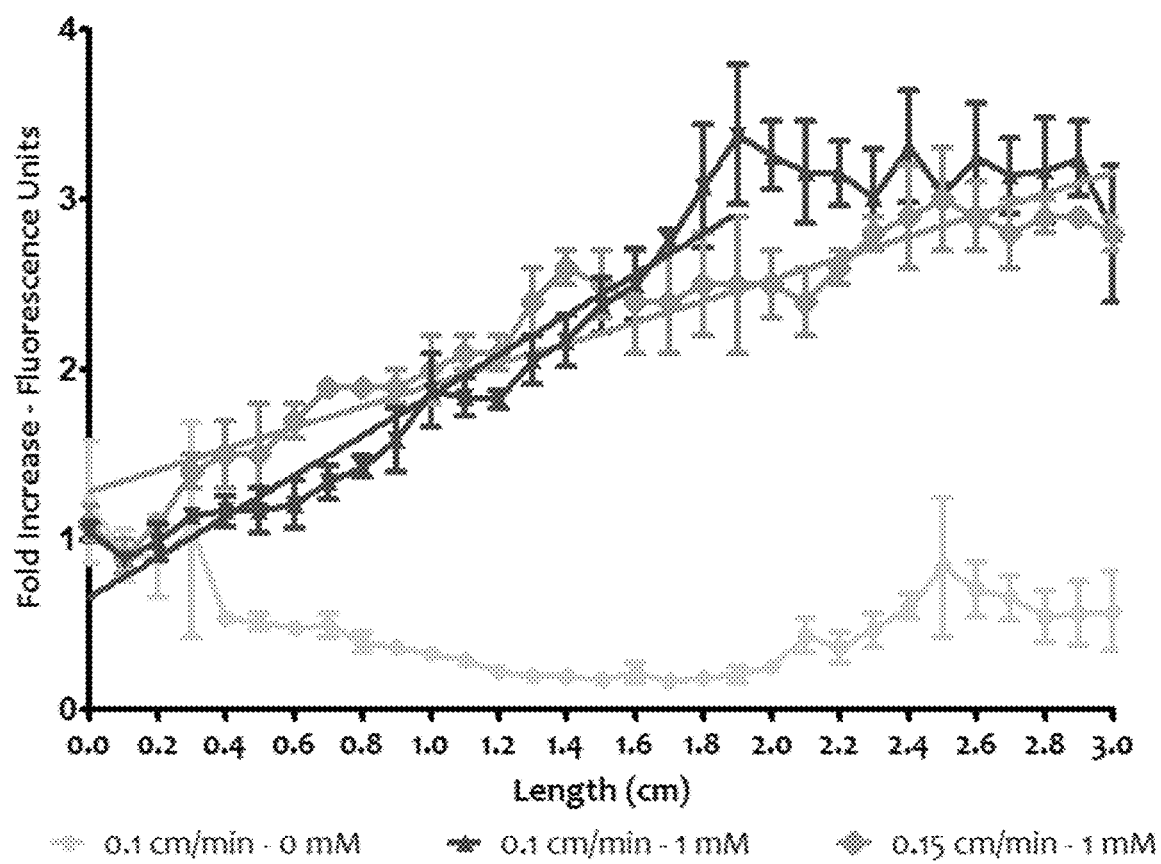
FIG. 22. Profiles of the immobilized TGF-β1 on TGF-β1-binding peptide gradients generated using 1 mM of TGF-β1-binding peptide at different pulling out speeds, as a function of the length of the PCL films. Fluorescence was calculated using ImageJ.

Next, the binding capacity of hTGF-β1 to the gradients of the TGF-β1-binding peptide was investigated via incubation with a solution of the GF. PCL films with TGF-β1-binding peptide gradients were incubated with 1 μg/mL of hTGF-β1 for one hour and then stained with the antibody against the GF. Images were recorded along the sample and mounted in one single picture that covered the entire length of the PCL film. Fluorescence intensity per pixel was calculated using ImageJ. First, it was assessed as to whether the concentration of the peptide used to generate the gradient would influence the profile of captured hTGF-β1. In the negative control, PCL films with NHS groups dipped into PBS, no fluorescence signal was observed (FIG. 21). In contrast, an increasing profile of fluorescence intensity was observed when the TGF-β1-binding peptide gradients were incubated with hTGF-β1, clearly showing that gradients of hTGF-β1 were achieved. The concentration of TGF-β1-binding peptide used to generate the gradient influenced the profile of immobilized hTGF-β1 (FIG. 21). When the films were pulled out of a solution of 1 mM of TGF-β1-binding peptide at the speed of 0.1 cm/minute, a linear increase in the fluorescence signal was observed from 0 to 1.9 cm ($r2=0.93$). From 1.9 until 3.0 cm, a plateau of fluorescence was reached. The slope for this linear region was 1.2±0.1 fluorescence units/cm (FU/cm). Using a lower concentration, 0.5 mM of TGF-β1-binding peptide, but with the same pulling out speed, allowed a different profile of immobilized hTGF-β1 to be observed (FIG. 21), with a linear region only observed from 1.9 to 3.0 cm ($r2=0.94$) with a slope of 1.7±0.1 FU/cm. The pulling out speed also influenced the gradient of the TGF-β1-binding peptide and consequently the profile of immobilized TGF-β1. When a speed of 0.15 cm/minute was used, using 1 mM of peptide, a linear behavior in the fluorescence response was observed across the entire film ($r2=0.9$) with a slope of 0.63±0.0 FU/cm (FIG. 22). The data show that the gradients of TGF-β1-binding peptide generated using an automated dip coater led to a gradient of immobilized hTGF-β1. Parameters such as the concentration of TGF-β1-binding peptide or the pulling out speed used affected the gradient of the TGF-β1-binding peptide on the PCL film, ultimately influencing the profile of the immobilized hTGF-β1.

In this work, a strategy was demonstrated to spatially control the presentation of hTGF-β1 in biomaterials. This was accomplished by generating gradients of TGF-β1-binding peptide on PCL films by using an automated dip coater. The profile of the TGF-β1-binding peptide gradient can be adjusted by altering parameters such as the peptide concentration or dipping out speed, ultimately leading to the precise control over the presentation of immobilized hTGF-β1. The technique demonstrated here can be used in the design of biomaterials with bioactive molecule gradients, such as GFs, peptides or other molecules, allowing the precise spatial control of the bioactive molecule, in order to better mimic the microenvironment sensed by cells and tissues.

Example 5

Functionalization of POLY-TAPE® with BMP-2 Binding Peptide Captures Endogenous BMP-2 and Accelerates Bone Healing in Rat Anterior Cruciate Ligament (ACL) Reconstruction Model Materials and Methods Animal Operation The surgical procedures were approved by the Animal Research Ethics Committee under the support of the University Laboratory Animal Services Centre. Male SD rats at 12 weeks old will be used. Under general anesthesia, the rat will be operated unilaterally in a randomly selected limb. The flexor digitorum longus tendon graft (20 mm in length and 1 mm in diameter) is harvested from a longitudinal medial incision. Meanwhile, the intact ACL is excised and the successful excision will be confirmed by a positive Lachman test. Tibial and femoral tunnels, both with 1.1 mm diameter and 6 mm in length, are created with drill guide from the footprint of the original ACL to the medial side of tibia and the lateral femoral condyle respectively, with an angle of ~55° to the articular surface. After rinsing the debris with saline, the graft is inserted and routed through the bone tunnels, and fixed with or without POLY-TAPE® (according to different groups) on both tunnel exits with suture tied over the neighboring periosteum. The fixation of graft at femoral end is performed under a 4N tensioning with the knee fully extended. Soft tissue is closed in layers. The animals are allowed for free cage activity after operation.

Functionalization of the POLY-TAPER with BMP-2 Binding Peptides

The POLY-TAPE® (iMove Medical, comprising polyethyleneterephthalate) was exposed to oxygen plasma for 5 minutes (at an oxygen pressure of 1.0 bar, a vacuum pressure of 200 mbar and a current of 40 A) and subsequently immersed in a 1 M NaOH solution for one hour with gentle agitation. POLY-TAPE® was then washed with demi-water and MILLI-Q® water and dried with nitrogen, and incubated with a solution of 50 mM 1:1 N-hydroxysuccinimide/1-ethyl-3-(3-dimethylaminopropyl)carbodiimide hydrochloride (NHS/EDC) in 2-(N-morpholino)ethanesulfonic acid (MES) buffer for one hour with agitation. POLY-TAPE® was washed and dried again as mentioned above and incubated with 1 mM of the peptide in phosphate buffered saline (PBS) for 4 hours with agitation. The sequence of the peptide was the same as in a previous example KGYPVHPST (SEQ ID NO:9).

XPS Measurements

XPS (X-ray photoelectron spectroscopy) spectra were measured using a Quantera scanning X-ray multiprobe instrument (Physical Electronics), equipped with a monochromatic Al Kα X-ray source operated at 1486.6 eV and 55 W. Spectra were referenced to the main aliphatic C 1 s peak set at 284.8 eV. The X-ray beam size was 200 μm and the data were collected from surface areas of 100 μm×300 μm with a pass energy of 224 eV and a step energy of 0.8 eV for survey scans, at a detector input angle of 45°. Measurements were collected after three scanning cycles. Charge neutralization was achieved by low-energy electrons and low-energy argon ions.

vivaCT Analysis

A cone-beam vivaCT system (VivaCT40, Scanco Medical AG, Bassersdorf, Switzerland) will be used to assess the bone mass and density of newly-formed mineralized tissue inside the bone tunnels. After thawing the sample, the region covering the entry and exit of bone tunnel will be scanned with vertical displacement of 30 μm for about 220 and 350 consecutive sections, respectively, for the femoral and tibial tunnels. The vivaCT sections will be 3-dimensionally (3D) reconstructed and rotated to align the bone tunnel vertically using the built-in software. ROI is defined as the bone tunnel. Bone mineral density (BMD) as defined by vivaCT (unit: mg HA/ccm) be calculated for ROI covering the tunnels. To measure the bone tunnel diameter, the tunnel wall will be traced and then the centroid will be calculated using image analysis software (Image Pro Plus 6.02). The minimum tunnel diameter of four equally-spaced sections at the different parts of the tunnel will be measured with reference to the centroid and averaged.

Histology

At week 2 and week 6 post-injury, the animals will be euthanized with intraperitoneal injection of overdose pentobarbital. The whole knee including the patellar tendon will then be trimmed out and fixed in buffered formalin for 24 hours, decalcified in 9% formic acid for 4 weeks, embedded in paraffin, and then sectioned in horizontal plane. After deparaffination, the sections will be stained with hematoxylin and eosin for the purpose of identifying the histological changes of healing ACL.

Results

Functionalization of POLY-TAPE®

Figure 23:
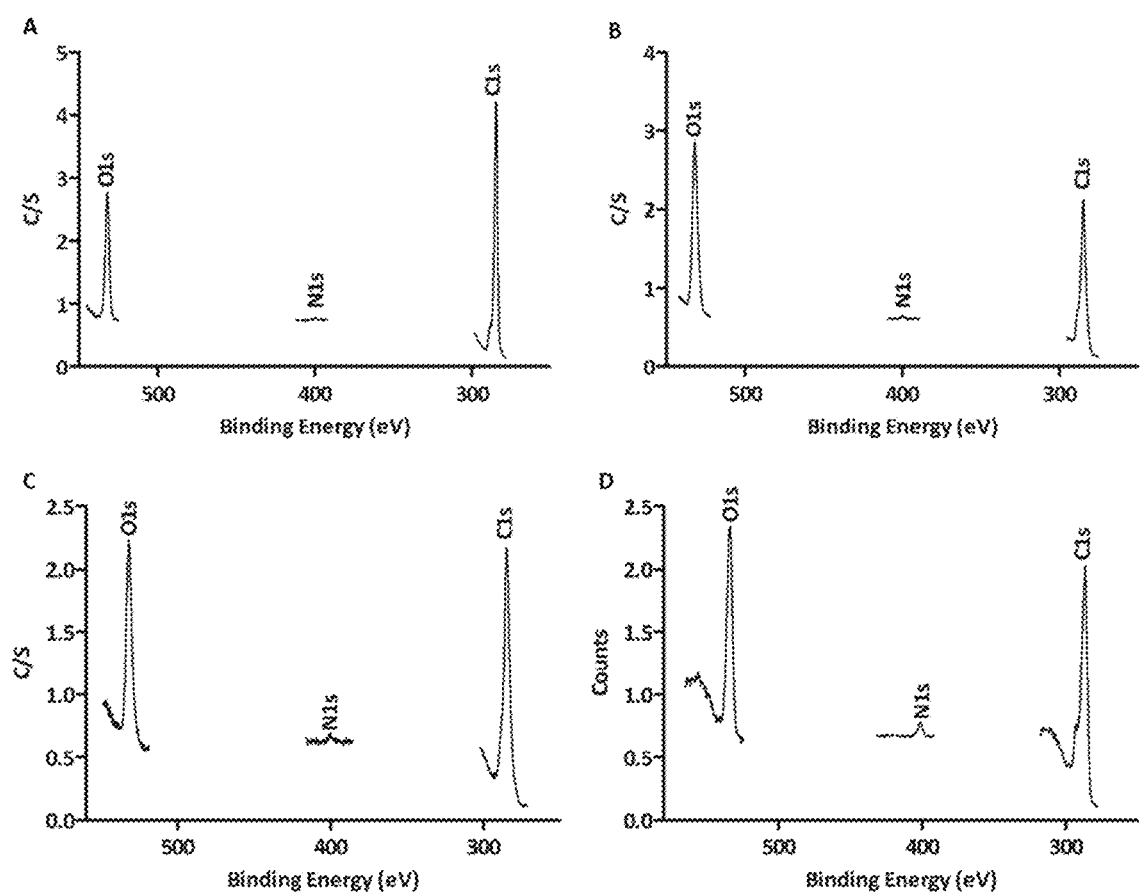
FIG. 23. Element spectrums of carbon, oxygen and nitrogen for the POLY-TAPE® after each chemical modification: (A) represents the POLY-TAPE® without any chemical modification; (B) is the POLY-TAPE® exposed for 5 minutes to oxygen plasma; (C) indicates the POLY-TAPE® with amine reactive esters after 1 hour incubation with NHS/EDC; (D) is the POLY-TAPE® with reactive amine esters incubated during 4 hours with a 1 mM of peptide in PBS.

Our XPS measurements show that the POLY-TAPE® is mainly composed of carbon and oxygen, which is typical of poly-esters (Table 1 and FIG. 23). After OPT the content of oxygen increased by 11.8±0.6% (p<0.0001), due to the introduction of oxygen groups, such as hydroxyl and carboxylic groups. After NHS/EDC treatment nitrogen was observed for the first time at the surface of the POLY-TAPE® due to the NHS groups. After peptide incubation, there was an increase of 1.0±0.3% (p<0.05) in the content of nitrogen. This increase was expected because the peptide molecule is composed of 17.8% nitrogen while the NHS groups are 12.5% nitrogen.

Surgical Procedure

Figure 24:
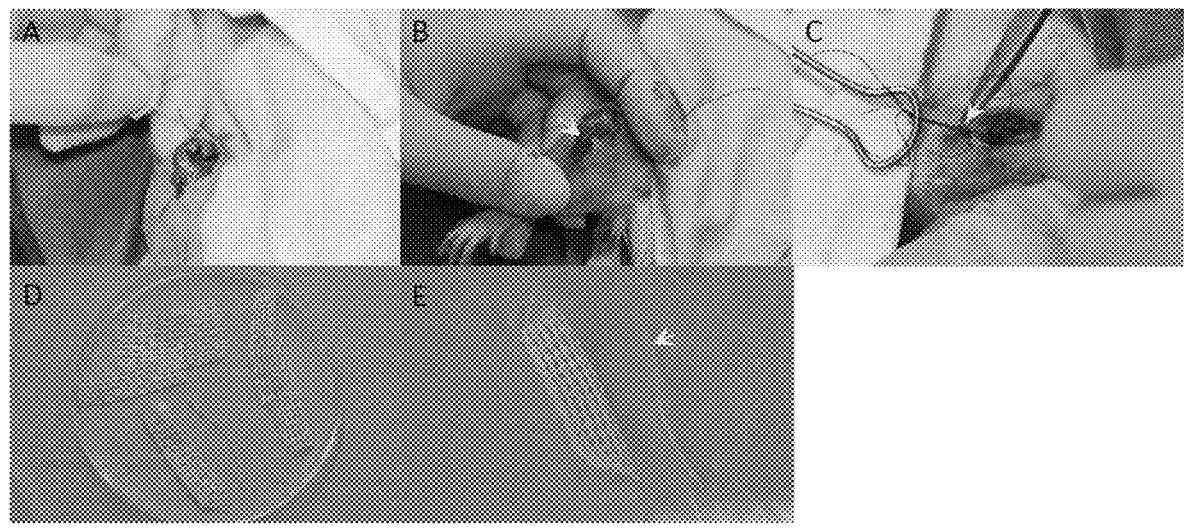
FIG. 24. Surgical procedure during the rat ACL reconstruction. (A) Graft and POLY-TAPE® pass through bone tunnels with loop. (B) Graft and POLY-TAPE® are fixed at the tibial tunnel with suture. (C) Graft and POLY-TAPE® are fixed at the femoral tunnel with suture under tension. (D) POLY-TAPE®. (E) POLY-TAPE® is tied with graft. Blue arrow indicates the graft while the yellow arrow indicates the POLY-TAPE®.
Figure 25:
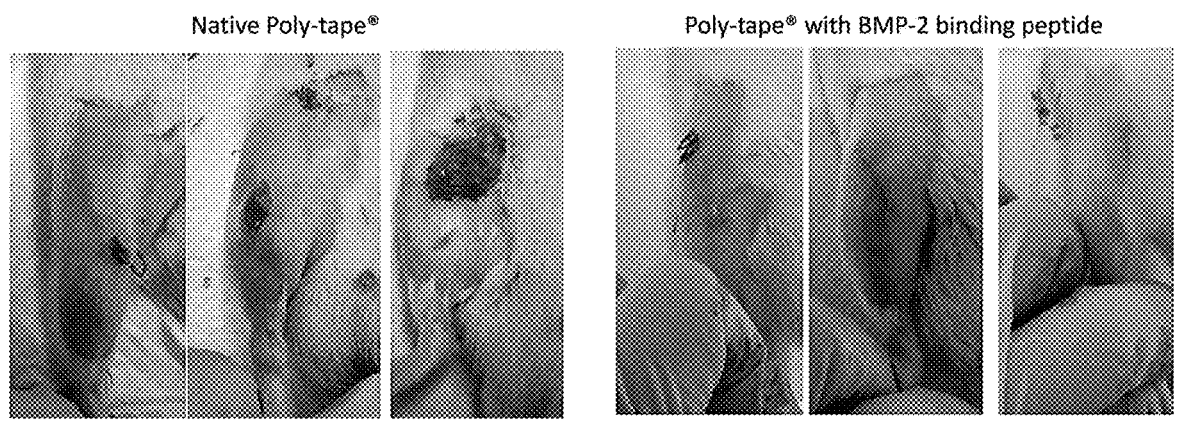
FIG. 25. Knee morphology at two weeks after surgery for native POLY-TAPE® and POLY-TAPE® displaying BMP-2 binding peptides.

During the ACL reconstruction, the POLY-TAPE® was sutured together with graft and both passed through the bone tunnels (FIG. 24, Panel A). Both the graft and the POLY-TAPE® were fixed at the tibial tunnel (FIG. 24, Panel B) and then at the femoral tunnel under tension (FIG. 24, Panel C). Knee swelling was observed at 2 weeks post-surgery in the knees that underwent ACL reconstruction as compared with intact knees, however there was no significant difference between groups (FIG. 25). Additionally, no difference between groups in weight changes after 2 and 6 weeks of ACL reconstruction was observed (Table 2).

Bone Formation

Figure 26:
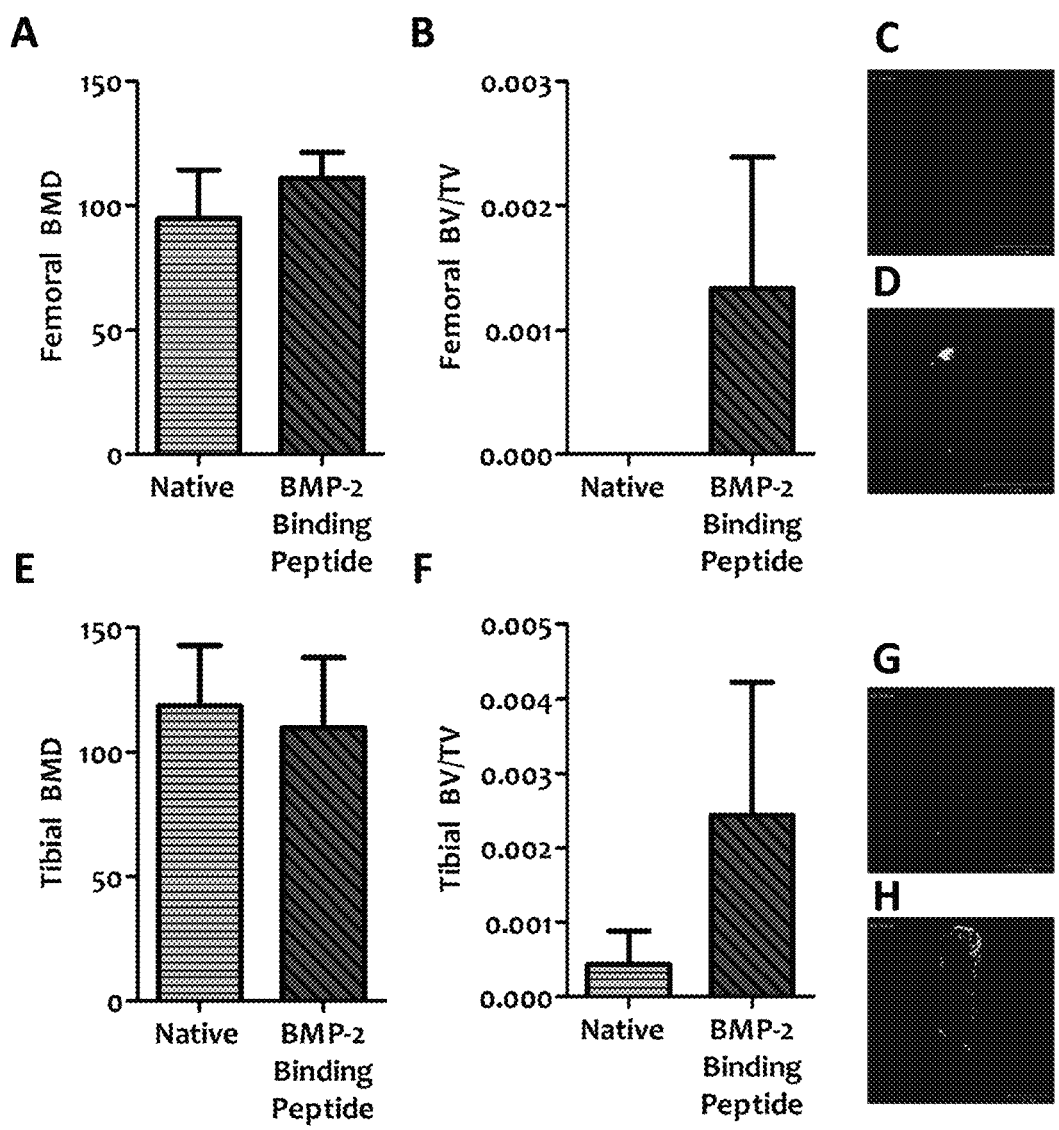
FIG. 26. μCT quantification after two weeks of (A) BMD inside the femoral tunnel. (B) BV/TV inside the femoral tunnel. (C) μCT picture of the femoral tunnel with native POLY-TAPE®. (D) μCT picture of the femoral tunnel with functionalized POLY-TAPE®. (E) BMD inside the tibial tunnel. (F) BV/TV inside the tibial tunnel. (G) μCT picture of the tibial tunnel with native POLY-TAPE®. (H) μCT picture of the tibial tunnel with functionalized POLY-TAPE®.
Figure 27:
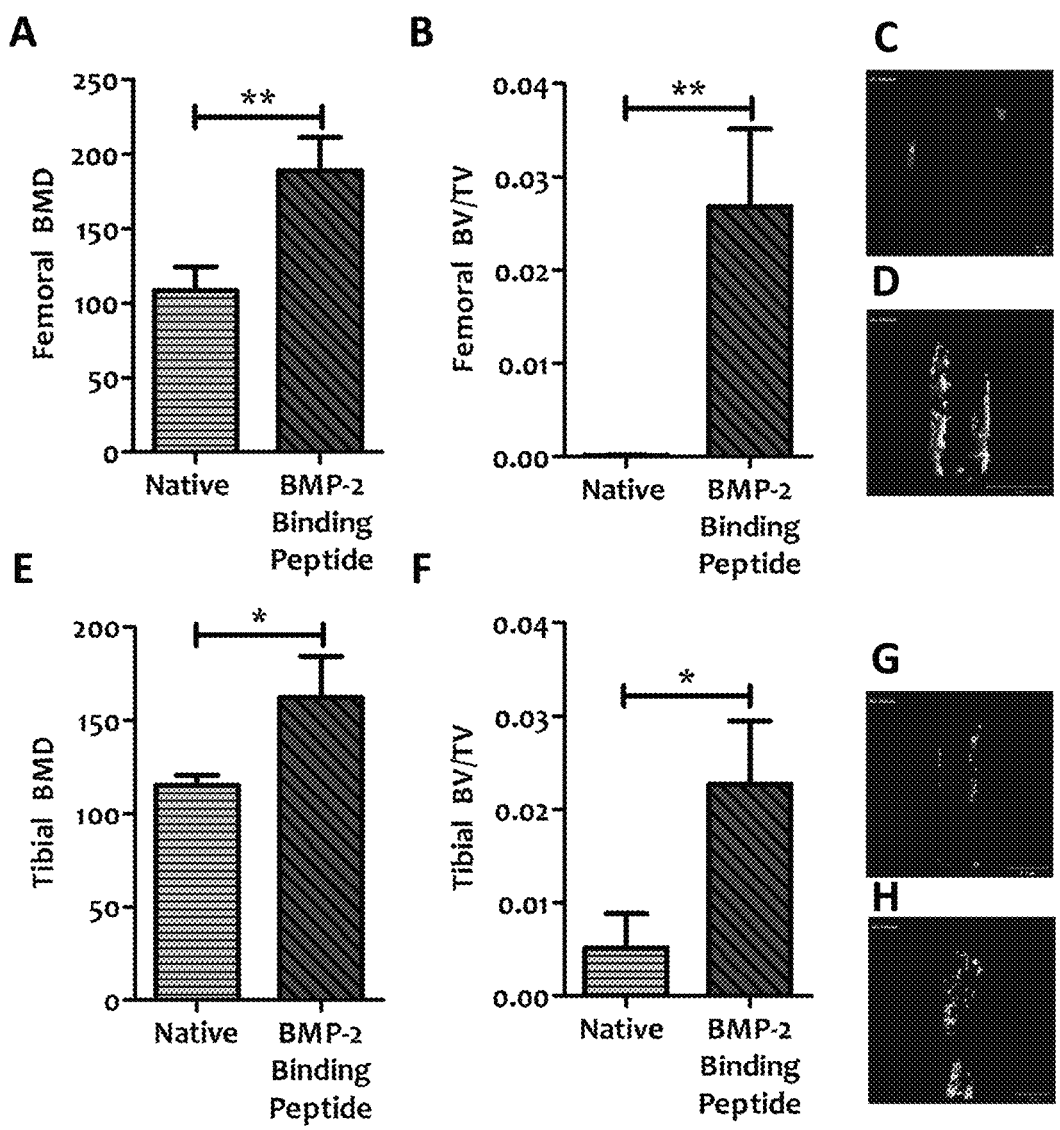
FIG. 27. μCT quantification after six weeks of (A) BMD inside the femoral tunnel. (B) BV/TV inside the femoral tunnel. (C) μCT picture of the femoral tunnel with native POLY-TAPE®. (D) μCT picture of the femoral tunnel with functionalized POLY-TAPE®. (E) BMD inside the tibial tunnel. (F) BV/TV inside the tibial tunnel. (G) μCT picture of the tibial tunnel with native POLY-TAPE®. (H) μCT picture of the tibial tunnel with functionalized POLY-TAPE®.

Two weeks after ACL reconstruction, improved BV/TV was observed in the POLY-TAPE® functionalized with BMp-2 binding peptides as compared with the control group, however no statistical differences were observed in BMD and BV/TV (FIG. 26).

Six weeks after ACL reconstruction, it was observed significant improvement in BMD and BV/TV in both the femoral and tibial tunnel for the group treated with the POLY-TAPE® functionalized with BMP-2 binding peptides.

Histology

Figure 28:
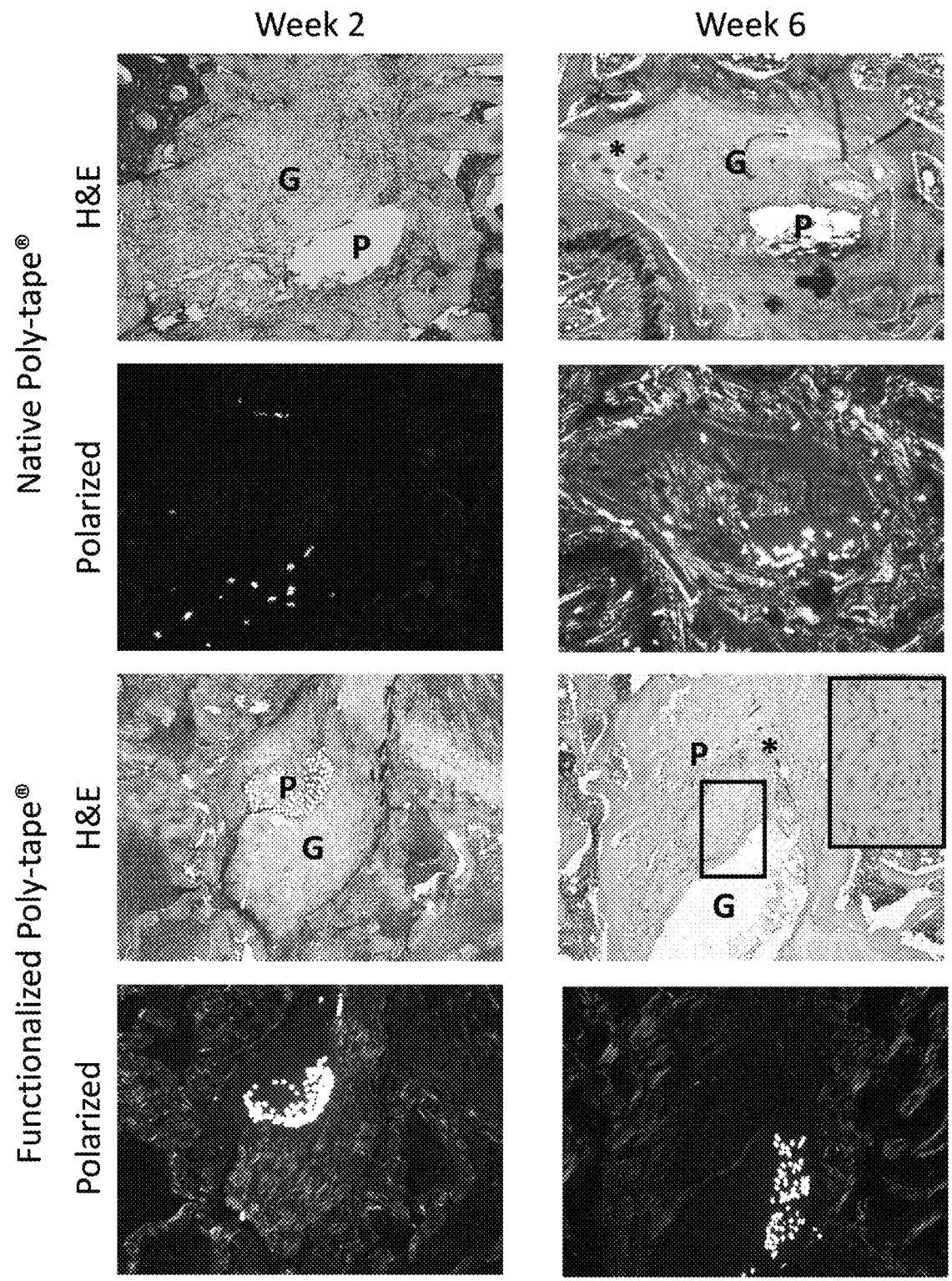
FIG. 28. Images of the H&E staining and polarized light at 2 and 6 weeks post-surgery inside the femoral tunnel for native POLY-TAPE® and POLY-TAPE® functionalized with the BMP-2 binding peptide. "G" identifies the graft, "P" identifies the POLY-TAPE®, "*" identifies mineralized regions and the red box identifies chondrocyte like cells.
Figure 29:
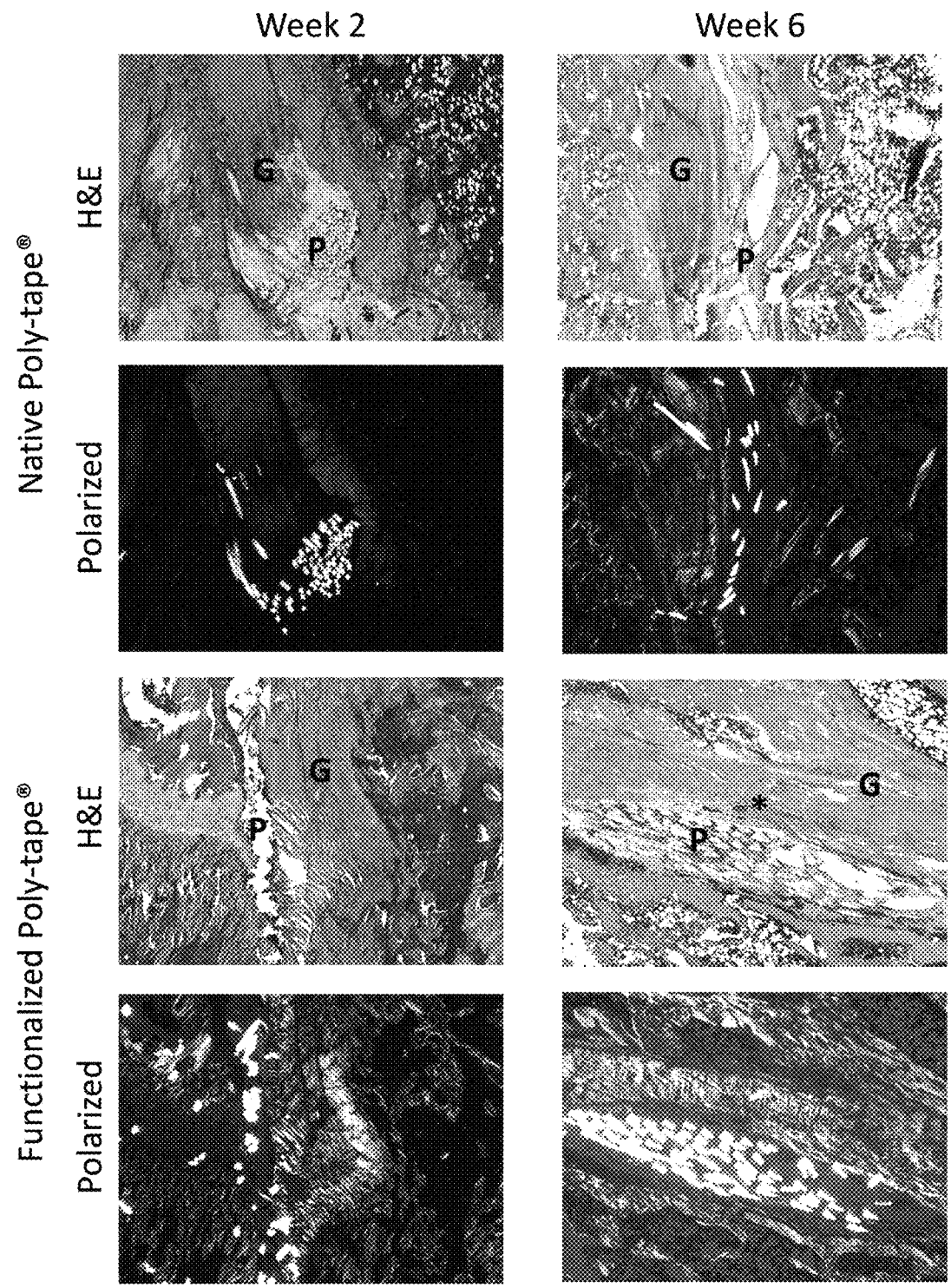
FIG. 29. Images of the H&E staining and polarized light at 2 and 6 weeks post-surgery inside the tibial tunnel for native POLY-TAPE® and POLY-TAPE® functionalized with the BMP-2 binding peptide. "G" identifies the graft, "P" identifies the POLY-TAPE®, identifies mineralized regions and the red box identifies chondrocyte like cells.

From the H&E staining, new bone formation was observed in both groups at week 6 (FIGS. 28 and 29). However in the group of the POLY-TAPE® functionalized with the BMP-2 binding peptide, the new bone formed was found organized around the functionalized POLY-TAPE®. In contrast, in the group with native POLY-TAPE® the new bone formed was found to randomly dispersed in the tunnels.

Figure 30:
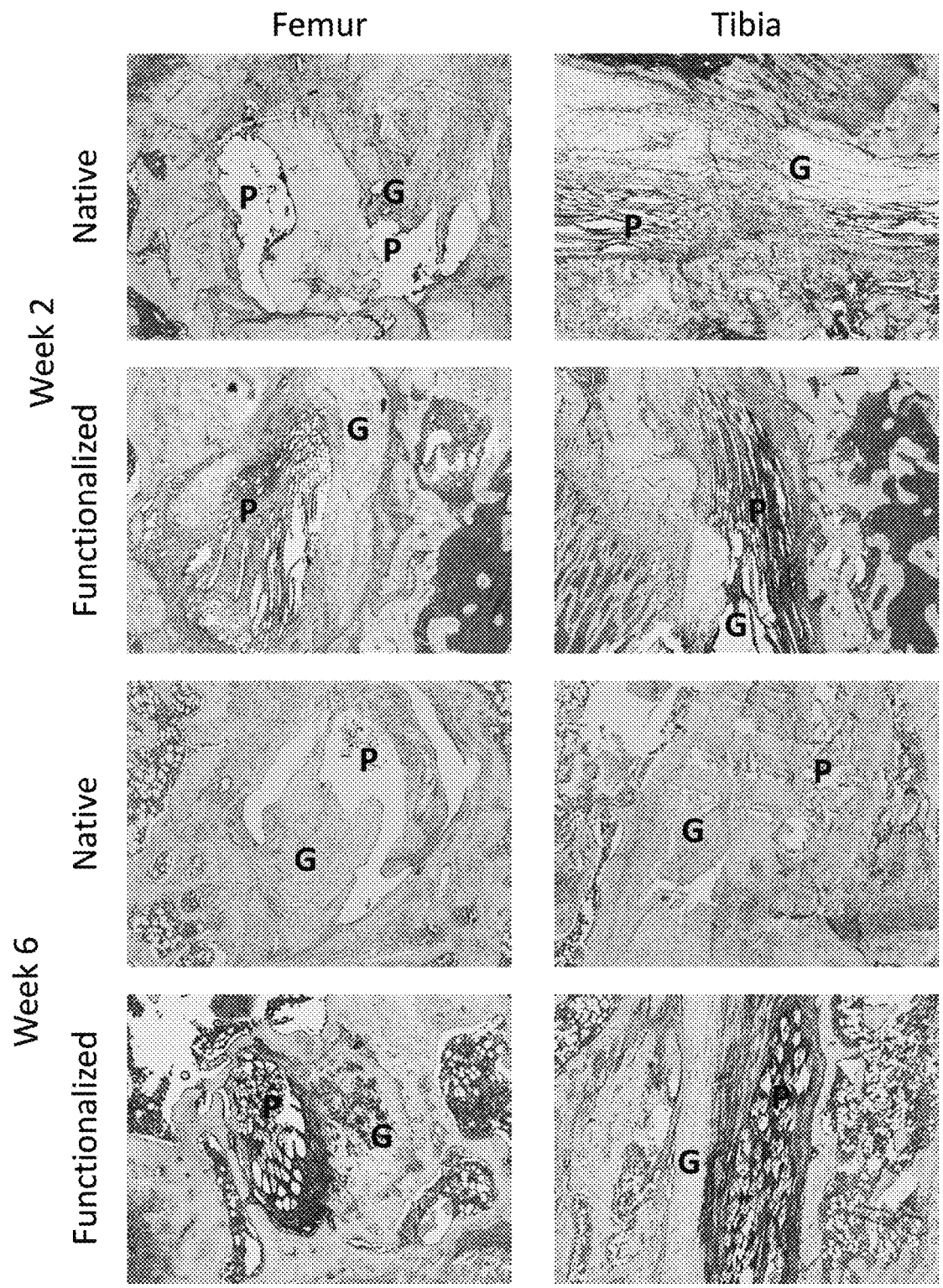
FIG. 30. Images of the immunohistochemistry against BMP-2 inside the femoral and tibial tunnel at weeks 2 and 6 post reconstruction with native POLY-TAPE® and POLY-TAPE® functionalized with BMP-2 binding peptides. "G" identifies the graft and "P" identifies the POLY-TAPE®.

To confirm that the accelerated bone formation in the POLY-TAPE® functionalized with BMP-2 binding peptide was due to the capture of endogenous BMP-2, the histology sections were stained against BMP-2 (FIG. 30). The presence of BMP-2 was much higher at week 2 and week 6 for the group treated with POLY-TAPE® functionalized with the BMP-2 binding peptide. The results also show that the BMP-2 is mostly found around the POLY-TAPE® and not the graft.

Conclusions

This example shows that presentation of BMP-2 binding peptides at the surface of biomaterials can capture endogenous BMP-2 and therefore enhance bone formation inside the femoral and tibial tunnels in a rat ACL reconstruction model.

Example 6

Functionalization of FIBER-TAPE® (Arthrex) with VEGF Binding Peptide to Enhance Vascularization of the Graft in a Rabbit Anterior Cruciate Ligament Model Materials and Methods Animal Operation All rabbits underwent a bilateral ACL reconstruction. Procedures on live rabbits (except sacrifice, which is detailed below) involved sedating the rabbits with ketamine and xylazine (35 and 5 mg/kg respectively, administered intra-muscularly). Rabbits were intubated and anesthesia was maintained using 1.5-3% isoflurane for no longer than 30 minutes. Analgesics were administered preoperatively (buprenorphine SR, 0.18 mg/kg, subcutaneous injection). Additionally, prophylactic antibiotics were administered 5 minutes prior to skin incision (cefazolin 22 mg/kg). Each animal had a semiteninosus graft harvested through a skin incision, with the fascia incised dorsally to the MCL and the tendon located deep to the medial vastus muscle. Tendon grafts were excised proximally at the tendon-muscle transition zone to ensure sufficient length (approximately 40 mm). Muscle were removed from the graft. Subsequently, 26 rabbit ACLs were debrided and replaced with semitendinosus tendon autograft (n=6), tendon with an internal FIBER-TAPE® splint (n=6), tendon with FIBER-TAPE® splint and covalently bound scrambled VEGF peptides (n=7), and tendon with VEGF functionalized FIBER-TAPE® (n=7). After surgery, each rabbit was monitored daily for signs of postoperative discomfort, infection, weight loss, or loss of contracture fixation. Any postoperative discomfort will be managed with intramuscular analgesics as needed (discomfort noted as loss of appetite, bruxism, or failure to groom). All animals will have free unrestrained ambulation and access to nutrition and water post operatively. Rabbits were sacrificed at 4 weeks and healing was evaluated using qPCR, histology, and micro ct (uct). The mayo clinic iacuc approves all procedures. FIBER-TAPE® comprises polypropyleen and poly (ethyleneterephthalate) fibers.

Functionalization of the FIBER-TAPER with BMP-2 Binding Peptides

The FIBER-TAPE® (Arthrex) was exposed to oxygen plasma for 5 minutes (at an oxygen pressure of 1.0 bar, a vacuum pressure of 200 mbar and a current of 40 A) and subsequently immersed in a 1 M NaOH solution for one hour with gentle agitation. FIBER-TAPE® was then washed with demi-water and MILLI-Q® water and dried with nitrogen, and incubated with a solution of 50 mM 1:1 N-hydroxysuccinimide/1-ethyl-3-(3-dimethylaminopropyl) carbodiimide hydrochloride (NHS/EDC) in 2-(N-morpholino)ethanesulfonic acid (MES) buffer for one hour with agitation. POLY-TAPE® was washed and dried again as mentioned above and incubated with 1 mM of the peptide in phosphate buffered saline (PBS) for 4 hours with agitation. The sequence of the peptide was KGSWWAPFH (SEQ ID NO:6). A higher concentration of peptide and/or a longer incubation did not result more peptide being added to the tape (based on the percentage of nitrogen atoms detected in XPS measurements).

XPS Measurements

XPS (X-ray photoelectron spectroscopy) spectra were measured using a Quantera scanning X-ray multiprobe instrument (Physical Electronics), equipped with a monochromatic Al Kα X-ray source operated at 1486.6 eV and 55 W. Spectra were referenced to the main aliphatic C 1 s peak set at 284.8 eV. The X-ray beam size was 200 μm and the data were collected from surface areas of 100 μm×300 μm with a pass energy of 224 eV and a step energy of 0.8 eV for survey scans, at a detector input angle of 45°. Measurements were collected after three scanning cycles. Charge neutralization was achieved by low-energy electrons and low-energy argon ions. The results of the XPS analysis are indicated in table 3.

Results

Figure 31:
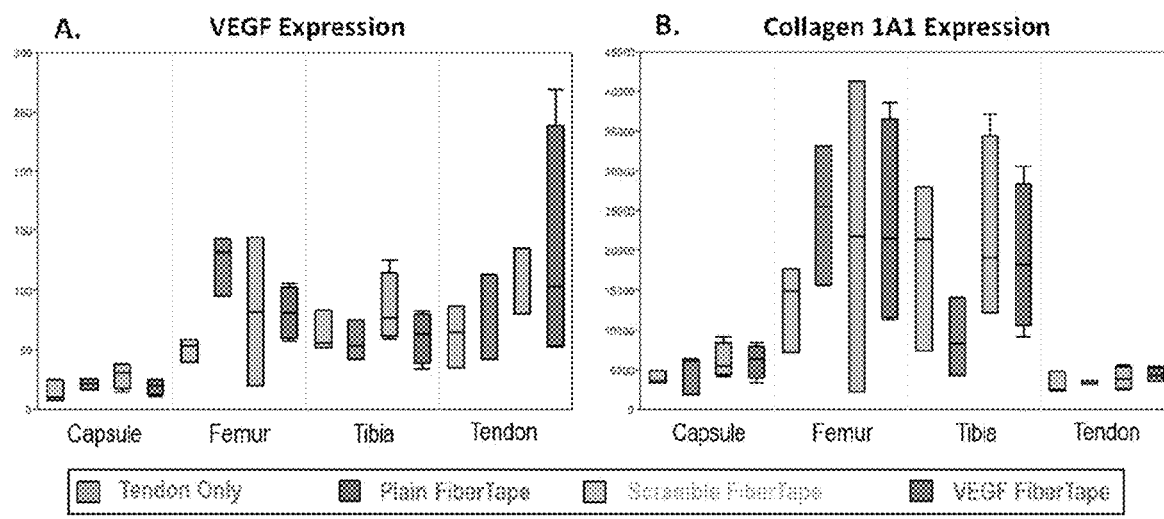
FIG. 31. A) qPCR VGEF expression in capsule, femur, tibia, and semitendonosus tendon graft. VGEF levels demonstrate a trend toward greater expression in the tendon augmented by VEGF-functionalized FIBER-TAPE®. B) Collagen 1 A1 expression in the four tissues demonstrates significantly increased expression in the femur and tibia, consistent with the bony nature of the locations as well as bine tunnel healing.
Figure 32:
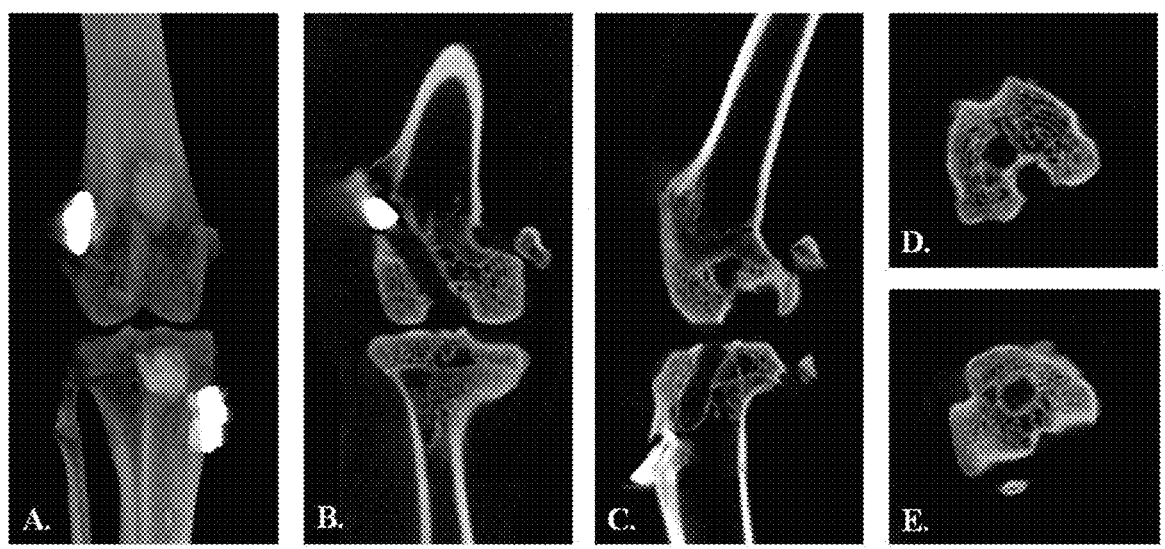
FIG. 32. A) 3D micro CT of VEGF-functionalized ACL reconstruction in a rabbit model with evident circumferential bony healing of tunnels in coronal (B) and saggital (C) views as well as axial slices of the femur (D) and tibia (E) at 4 weeks post-operatively.

All rabbits successfully underwent ACL reconstruction. Following 4 weeks of tendon healing, ACLs reconstructed with VEGF-functionalized FIBER-TAPE® trended toward increased VEGF expression (mean GAPDH-normalized expression=132.4) compared to tendon only (mean=62.4) and tendon and plain FIBER-TAPE® controls (mean=66.2) (p=0.38, FIG. 31, Panel A, and FIG. 31, Panel B). uCT demonstrated bony ingrowth surrounding the femoral and tibial tunnels in VEGF-functionalized rabbits, with associated increases in bone tunnel COL1A1 expression on qPCR (FIG. 32). Fellowship-trained veterinarians necropsied four VEGF rabbits noting no adverse systemic effects.

Conclusions

The use of VEGF-binding peptides has the potential to significantly improve bone-tendon healing and tendon revascularization. Considering that ACL rupture is a common injury with high re-rupture rates and known relationship to osteoarthritis, biologically enhanced methods have the potential to revolutionize ligament reconstruction for both return to sport and chondroprotection.

TABLE 1

XPS results of carbon, oxygen, nitrogen and other elements for the POLY-TAPE ® during the chemical functionalization procedure and theoretical calculations with respective chemical formulas (excluding hydrogen) for POLY-TAPE ®, NHS group and the peptide molecule. "Native POLY-TAPE ®" represents the POLY-TAPE ® without any chemical modification; "POLY-TAPE ® after OPT" is the native POLY-TAPE ® exposed for 5 minutes to oxygen plasma; "POLY-TAPE ® Cov-NHS" indicates the POLY-TAPE ® with amine reactive esters after 1 hour incubation with NHS/EDC; "POLY-TAPE ® with Peptide" is the POLY-TAPE ® with reactive amine esters incubated during 4 hours with a 1 mM of peptide in PBS. The data represent the mean ± SD of four measurements per sample.

| Element | Carbon | Oxygen | Nitrogen | Other elements |
|---|---|---|---|---|
| Native POLY-TAPE ® | 78.9 ± 1.2 | 20.7 ± 1.2 | — | 0.4 ± 0.2 |
| POLY-TAPE ® after OPT | 67.7 ± 0.5 | 32.5 ± 0.4 | — | 0.4 ± 0.2 |
| POLY-TAPE ® Cov-NHS | 73.3 ± 0.9 | 25.6 ± 1.1 | 1.2 ± 0.3 | — |
| POLY-TAPE ® with Peptide | 72.4 ± 2.5 | 25.4 ± 2.0 | 2.2 ± 0.5 | — |
| Calculated for -NHS group ($C_4NO_3$) | 50.0 | 37.5 | 12.5 | — |
| Calculated for peptide ($C_{47}H_{71}N_{13}O_{13}$) | 64.4 | 17.8 | 17.8 | — |

TABLE 2

Weight and weight changes of knees of the animals that underwent ACL reconstruction with native POLY-TAPE ® and POLY-TAPE ® with BMP-2 binding peptides.

| Group | Weight (g) (before ACLR) | Weight (g) (2 weeks post ACLR) | Percent changes (%) (2 weeks) | Weight (g) (6 weeks post ACLR) | Percent changes (%) (6 weeks) |
|---|---|---|---|---|---|
| Native POLY-TAPE ® | 383.7 ± 15.0 | 387.7 ± 41.4 | −1.7 ± 8.6 | 375.8 ± 19.9 | 0.86 ± 4.2 |
| POLY-TAPE ® with BMP-2 binding peptide | 388.1 ± 23.0 | 396.7 ± 23.2 | −0.6 ± 0.3 | 434.0 ± 14.0 | 15.5 ± 9.5 |

TABLE 3

XPS results of carbon, oxygen, nitrogen and other elements for the FIBER-TAPE ® during the chemical functionalization procedure and theoretical calculations with respective chemical formulas (excluding hydrogen) for FIBER-TAPE ®, NHS group and the peptide molecule. Native FIBER-TAPE ® represents the FIBER-TAPE ® without any chemical modification; "FIBER-TAPE ® after OPT" is the native FIBER-TAPE ® exposed for 5 minutes to oxygen plasma; "FIBER-TAPE ® Cov-NHS" indicates the FIBER-TAPE ® with amine reactive esters after 1 hour incubation with NHS/EDC; "FIBER-TAPE ® with Peptide" is the FIBER-TAPE ® with reactive amine esters incubated during 4 hours with a 1 mM of peptide in PBS. The data represent the mean ± SD of four measurements per sample.

| Element | Carbon | Oxygen | Nitrogen | Other elements |
|---|---|---|---|---|
| Native FIBER-TAPE ® | 88.1 ± 0.6 | 11.8 ± 0.5 | — | 0.1 ± 0.1 |
| FIBER-TAPE ® after OPT | 80.8 ± 5.3 | 17.9 ± 4.8 | — | 1.3 ± 0.6 |
| FIBER-TAPE ® Cov-NHS | 75.8 ± 1.8 | 22.7 ± 1.9 | 1.5 ± 0.1 | 0.1 ± 0.1 |
| FIBER-TAPE ® with Peptide | 71.0 ± 1.2 70.25 5 72.42 5 | 23.2 ± 0.9 | 5.6 ± 0.4 | 0.2 ± 0.1 |
| Calculated for -NHS group (C4NO3) | 50.0 | 37.5 | 12.5 | — |
| Calculated for peptide (C58H73N15O11) | 69.0 | 13.1 | 17.9 | — |

The invention claimed is:

1. A biopolymer that is functionalized with a peptide, wherein the biopolymer is a synthetic polyester, wherein the peptide comprises KGLPLGNSH (SEQ ID NO:3), wherein the number of amino acid residues in the peptide is up to 50; and
wherein the peptide is coupled to a carbonyl group of the non-functionalized biopolymer through binding of an N-terminal amino group of the peptide, or through binding of an amino group in a side chain of the N-terminal lysine of the peptide.

2. The biopolymer of claim 1, wherein the peptide is present on the biopolymer in a concentration-gradient.

3. The biopolymer of claim 1, wherein the biopolymer is selected from the group consisting of polylactic acid, poly-L-lactic acid, polyglycolic acid, polyglycolic lactic acid, poly(caprolactone), polyalkyleneoxide-polyalkylene-terephthalate block copolymer, polyesters, polyethylene terephthalate (PET), polybutylene A terephthalate (PBT), polytrimethylenecaprolactone (PTMC) and/or combinations thereof.

4. The biopolymer of claim 1, wherein the polyester is poly(caprolactone).

5. The biopolymer of claim 1, wherein the peptide is coupled to the carbonyl group of the non-functionalized biopolymer through binding of an amino group in a side chain of the N-terminal lysine of the peptide.

6. A device comprising the biopolymer of claim 1.

7. A method of treating an injured tendon and/or ligament, the method comprising:
utilizing the biopolymer of claim 1 in the treatment of an injured tendon and/or ligament.

8. A biopolymer, the biopolymer comprising a synthetic polyester coupled to a peptide produced by a method for coupling amino groups of peptides to carbonyl groups of the polyester, wherein the peptide comprises KGLPLGNSH (SEQ ID NO:3) and wherein the number of amino acid residues in the peptide is up to 50, the method comprising:
(a) reacting the polyester with oxygen plasma;
(b) treating the reacted polyester with alkaline, and
(c) coupling the peptide through an N-terminal amino group or an amino group in a side chain of the N-terminal lysine to a carbonyl group of the treated polyester using a cross-linker.

9. The biopolymer of claim 8, wherein the polyester comprises polylactic acid, poly-L-lactic acid, polyglycolic acid, polyglycolic lactic acid, poly(caprolactone), polyalkyleneoxide-polyalkylene-terephthalate block copolymer, polyethylene terephthalate (PET), polybutylene terephthalate (PBT), or polytrimethylenecaprolactone (PTMC).

10. The biopolymer of claim 9, wherein the polyester is poly(caprolactone).

11. The biopolymer of claim 8, wherein the peptide is coupled to the carbonyl group of the non-functionalized biopolymer through binding of an amino group in a side chain of the N-terminal lysine of the peptide.

12. The biopolymer of claim 8, wherein the cross-linker is a carbodiimide.

13. The biopolymer of claim 8, wherein the cross-linker is 1-ethyl-3-(3-dimethylaminopropyl)carbodiimide (EDC) and/or N-hydroxysuccinimide (NHS).

14. The biopolymer of claim 8, wherein the biopolymer is comprised within a device.

* * * * *

SEQUENCE LISTING

<160> NUMBER OF SEQ ID NOS: 47

<210> SEQ ID NO 1
<211> LENGTH: 7
<212> TYPE: PRT
<213> ORGANISM: Artificial Sequence
<220> FEATURE:
<223> OTHER INFORMATION: TGFB-binding peptide

<400> SEQUENCE: 1

Leu Pro Leu Gly Asn Ser His
1               5

<210> SEQ ID NO 2
<211> LENGTH: 8
<212> TYPE: PRT
<213> ORGANISM: Artificial Sequence
<220> FEATURE:
<223> OTHER INFORMATION: TGFB-binding peptide

<400> SEQUENCE: 2

Gly Leu Pro Leu Gly Asn Ser His
1               5

```
<210> SEQ ID NO 3
<211> LENGTH: 9
<212> TYPE: PRT
<213> ORGANISM: Artificial Sequence
<220> FEATURE:
<223> OTHER INFORMATION: TGFB-binding peptide

<400> SEQUENCE: 3

Lys Gly Leu Pro Leu Gly Asn Ser His
1               5

<210> SEQ ID NO 4
<211> LENGTH: 7
<212> TYPE: PRT
<213> ORGANISM: Artificial Sequence
<220> FEATURE:
<223> OTHER INFORMATION: VEGF-binding peptide

<400> SEQUENCE: 4

Ser Trp Trp Ala Pro Phe His
1               5

<210> SEQ ID NO 5
<211> LENGTH: 8
<212> TYPE: PRT
<213> ORGANISM: Artificial Sequence
<220> FEATURE:
<223> OTHER INFORMATION: VEGF-binding peptide

<400> SEQUENCE: 5

Gly Ser Trp Trp Ala Pro Phe His
1               5

<210> SEQ ID NO 6
<211> LENGTH: 9
<212> TYPE: PRT
<213> ORGANISM: Artificial Sequence
<220> FEATURE:
<223> OTHER INFORMATION: VEGF-binding peptide

<400> SEQUENCE: 6

Lys Gly Ser Trp Trp Ala Pro Phe His
1               5

<210> SEQ ID NO 7
<211> LENGTH: 7
<212> TYPE: PRT
<213> ORGANISM: Artificial Sequence
<220> FEATURE:
<223> OTHER INFORMATION: BMP-binding peptide

<400> SEQUENCE: 7

Tyr Pro Val His Pro Ser Thr
1               5

<210> SEQ ID NO 8
<211> LENGTH: 8
<212> TYPE: PRT
<213> ORGANISM: Artificial Sequence
<220> FEATURE:
<223> OTHER INFORMATION: BMP-binding peptide

<400> SEQUENCE: 8

Gly Tyr Pro Val His Pro Ser Thr
1               5

<210> SEQ ID NO 9
```

```
<211> LENGTH: 9
<212> TYPE: PRT
<213> ORGANISM: Artificial Sequence
<220> FEATURE:
<223> OTHER INFORMATION: BMP-binding peptide

<400> SEQUENCE: 9

Lys Gly Tyr Pro Val His Pro Ser Thr
1               5

<210> SEQ ID NO 10
<211> LENGTH: 10
<212> TYPE: PRT
<213> ORGANISM: Artificial Sequence
<220> FEATURE:
<223> OTHER INFORMATION: TGFB1-binding peptide

<400> SEQUENCE: 10

Lys Gly Gly Leu Pro Leu Gly Asn Ser His
1               5                   10

<210> SEQ ID NO 11
<211> LENGTH: 11
<212> TYPE: PRT
<213> ORGANISM: Artificial Sequence
<220> FEATURE:
<223> OTHER INFORMATION: TGFB1-binding peptide

<400> SEQUENCE: 11

Lys Gly Gly Gly Leu Pro Leu Gly Asn Ser His
1               5                   10

<210> SEQ ID NO 12
<211> LENGTH: 12
<212> TYPE: PRT
<213> ORGANISM: Artificial Sequence
<220> FEATURE:
<223> OTHER INFORMATION: TGFB1-binding peptide

<400> SEQUENCE: 12

Lys Gly Gly Gly Gly Leu Pro Leu Gly Asn Ser His
1               5                   10

<210> SEQ ID NO 13
<211> LENGTH: 10
<212> TYPE: PRT
<213> ORGANISM: Artificial Sequence
<220> FEATURE:
<223> OTHER INFORMATION: BMP2-binding peptide

<400> SEQUENCE: 13

Lys Gly Gly Tyr Pro Val His Pro Ser Thr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: BMP2-binding peptide

<400> SEQUENCE: 14

Lys Gly Gly Gly Tyr Pro Val His Pro Ser Thr
1               5                   10

<210> SEQ ID NO 15
<211> LENGTH: 12
```

```
<212> TYPE: PRT
<213> ORGANISM: Artificial Sequence
<220> FEATURE:
<223> OTHER INFORMATION: BMP2-binding peptide

<400> SEQUENCE: 15

Lys Gly Gly Gly Gly Tyr Pro Val His Pro Ser Thr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: VEGF-binding peptide

<400> SEQUENCE: 16

Lys Gly Gly Ser Trp Trp Ala Pro Phe His
1               5                   10

<210> SEQ ID NO 17
<211> LENGTH: 11
<212> TYPE: PRT
<213> ORGANISM: Artificial Sequence
<220> FEATURE:
<223> OTHER INFORMATION: VEGF-binding peptide

<400> SEQUENCE: 17

Lys Gly Gly Gly Ser Trp Trp Ala Pro Phe His
1               5                   10

<210> SEQ ID NO 18
<211> LENGTH: 12
<212> TYPE: PRT
<213> ORGANISM: Artificial Sequence
<220> FEATURE:
<223> OTHER INFORMATION: VEGF-binding peptide

<400> SEQUENCE: 18

Lys Gly Gly Gly Gly Ser Trp Trp Ala Pro Phe His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 19

Lys Val Pro Pro Ala Asn Thr
1               5

<210> SEQ ID NO 20
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 20

Lys Gln Ala Leu Thr Gln Thr
1               5

<210> SEQ ID NO 21
<211> LENGTH: 7
<212> TYPE: PRT
```

```
<213> ORGANISM: Artificial Sequence
<220> FEATURE:
<223> OTHER INFORMATION: growth factor binding peptide

<400> SEQUENCE: 21

Trp Pro Ala Leu Phe Thr His
1               5

<210> SEQ ID NO 22
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 22

Pro Gly Pro Thr Val Gln Gly
1               5

<210> SEQ ID NO 23
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 23

Leu His Tyr Pro Phe Met Thr
1               5

<210> SEQ ID NO 24
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 24

Gln Gln Thr Gln Ala Gln His
1               5

<210> SEQ ID NO 25
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 25

Pro Ile Gln Pro Asp Glu Arg
1               5

<210> SEQ ID NO 26
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 26

Pro Phe Asp Pro Pro Val Arg
1               5

<210> SEQ ID NO 27
<211> LENGTH: 7
<212> TYPE: PRT
<213> ORGANISM: Artificial Sequence
```

```
<220> FEATURE:
<223> OTHER INFORMATION: growth factor binding peptide

<400> SEQUENCE: 27

Asp Val Ser Pro Ala Tyr His
1               5

<210> SEQ ID NO 28
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 28

Leu Arg Asn Tyr Ser His Ser
1               5

<210> SEQ ID NO 29
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 29

Val Tyr Arg His Leu Pro Thr
1               5

<210> SEQ ID NO 30
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 30

Arg Val Ser Thr Trp Asp Thr
1               5

<210> SEQ ID NO 31
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 31

Pro Ala Pro Arg Trp Ile His
1               5

<210> SEQ ID NO 32
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 32

Arg Thr Thr Ser Pro Thr Ala
1               5

<210> SEQ ID NO 33
<211> LENGTH: 7
<212> TYPE: PRT
<213> ORGANISM: Artificial Sequence
<220> FEATURE:
```

```
<223> OTHER INFORMATION: growth factor binding peptide

<400> SEQUENCE: 33

Gly Lys Tyr Pro Pro Thr Ser
1               5

<210> SEQ ID NO 34
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 34

Ala Trp Lys Ser Val Thr Ala
1               5

<210> SEQ ID NO 35
<211> LENGTH: 7
<212> TYPE: PRT
<213> ORGANISM: Artificial Sequence
<220> FEATURE:
<223> OTHER INFORMATION: growth factor binding peptide

<400> SEQUENCE: 35

Leu Pro Ser Pro Ile Gln Lys
1               5

<210> SEQ ID NO 36
<211> LENGTH: 9
<212> TYPE: PRT
<213> ORGANISM: Artificial Sequence
<220> FEATURE:
<223> OTHER INFORMATION: control peptide

<400> SEQUENCE: 36

Lys Gly His Asn Leu Gly Leu Pro Ser
1               5

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
gtcacccacc gaccaagaaa cc                                              22

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
aagtccaggc tgtccaggga tg                                              22

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
```

-continued

```
gccaacgtcc acaccaaatt                                              20

<210> SEQ ID NO 40
<211> LENGTH: 21
<212> TYPE: DNA
<213> ORGANISM: Artificial Sequence
<220> FEATURE:
<223> OTHER INFORMATION: primer

<400> SEQUENCE: 40
aacacgcaag gctgtgagac t                                            21

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
atccggtggt ccttcttgtg                                              20

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
tgggcaagct ctggagactt c                                            21

<210> SEQ ID NO 43
<211> LENGTH: 19
<212> TYPE: DNA
<213> ORGANISM: Artificial Sequence
<220> FEATURE:
<223> OTHER INFORMATION: primer

<400> SEQUENCE: 43
aggcagcgtg atccttacc                                               19

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
ggcctctcca gtctcattct c                                            21

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
acaaagtcac atggttcaca                                              20

<210> SEQ ID NO 46
<211> LENGTH: 20
<212> TYPE: DNA
```

```
<213> ORGANISM: Artificial Sequence
<220> FEATURE:
<223> OTHER INFORMATION: primer

<400> SEQUENCE: 46
gacttgtctt tcagcaagga                                                 20

<210> SEQ ID NO 47
<211> LENGTH: 9
<212> TYPE: PRT
<213> ORGANISM: Artificial Sequence
<220> FEATURE:
<223> OTHER INFORMATION: control peptide

<400> SEQUENCE: 47

Lys Gly Thr Pro Val His Tyr Pro Ser
1               5
```